US005863783A

United States Patent [19]
Van Heuvel et al.

[11] Patent Number: 5,863,783
[45] Date of Patent: Jan. 26, 1999

[54] CLONING AND EXPRESSION OF DNA MOLECULES ENCODING ARABINAN-DEGRADING ENZYMES OF FUNGAL ORIGIN

[75] Inventors: Margaretha Van Heuvel, Leiden; Janna Gardina Bakhuis, Delft, both of Netherlands; Yves Coutel, Ennevelin, France; Abraham Harder, Berkel en Rodenrijs, Netherlands; Leendert Hendrick De Graaff, Oosterbeek, Netherlands; Michel Johannes Anthonie Flipphi, Wageningen, Netherlands; Peter Van Der Veen, Wageningen, Netherlands; Jacob Visser, Wageningen, Netherlands; Peter Michael Andreoli, Bellegem-Kortrijk, Netherlands

[73] Assignee: Gist-brocades, N.V., Netherlands

[21] Appl. No.: 952,853

[22] PCT Filed: Mar. 27, 1991

[86] PCT No.: PCT/NL92/00056

§ 371 Date: Nov. 25, 1992

§ 102(e) Date: Nov. 25, 1992

[87] PCT Pub. No.: WO92/17592

PCT Pub. Date: Oct. 18, 1992

[30] Foreign Application Priority Data

Mar. 27, 1991 [EP] European Pat. Off. ........... 91200720.0

[51] Int. Cl.⁶ ............... C12N 9/24; C12N 15/56; C12N 15/74; C12N 15/80
[52] U.S. Cl. ............... 435/200; 435/69.1; 435/72; 435/252.3; 435/252.31; 435/172.3; 435/254.11; 435/254.21; 435/254.3; 435/254.6; 435/320.1; 536/23.2; 935/14; 935/28; 935/68; 935/69
[58] Field of Search ................... 435/69.1, 200, 435/252.3, 320.1, 254.3, 72, 252.31, 254.21, 254.6, 172.3; 536/23.2

[56] References Cited

U.S. PATENT DOCUMENTS

| | | | |
|---|---|---|---|
| 4,703,008 | 10/1987 | Lin | 435/240.2 |
| 4,757,006 | 7/1988 | Toole, Jr. et al. | 435/69.6 |
| 4,760,025 | 7/1988 | Estell et al. | 435/222 |
| 5,013,652 | 5/1991 | Strausberg et al. | 435/69.2 |
| 5,075,227 | 12/1991 | Hagen | 435/172.3 |
| 5,108,918 | 4/1992 | Groenen et al. | 435/172.3 |
| 5,143,844 | 9/1992 | Abrahmsén et al. | 435/257.3 |
| 5,188,958 | 2/1993 | Moloney et al. | 435/240.4 |
| 5,246,849 | 9/1993 | Bryan et al. | 435/222 |
| 5,324,653 | 6/1994 | Van Eekelen et al. | 435/221 |
| 5,336,611 | 8/1994 | Van Eekelen et al. | 435/221 |
| 5,340,735 | 8/1994 | Christianson et al. | 435/221 |
| 5,340,738 | 8/1994 | Lambeir et al. | 435/234 |
| 5,384,257 | 1/1995 | Lambeir et al. | 435/324 |
| 5,397,705 | 3/1995 | Zukowski et al. | 435/222 |
| 5,482,849 | 1/1996 | Branner et al. | 435/222 |

FOREIGN PATENT DOCUMENTS

| | | | |
|---|---|---|---|
| 0311469 | 4/1989 | European Pat. Off. | 435/252.3 |
| 332281 | 9/1989 | European Pat. Off. | |
| 124812 | 3/1977 | Germany . | |
| 8504627 | 10/1985 | WIPO | 435/252.3 |
| WO 90/06343 | 6/1990 | WIPO . | |

OTHER PUBLICATIONS

Whitaker et al., "Pectic substances, peptic enzymes and haze formation in fruit juices" *Enzyme Microb. Technol.* (1984)6:341–349.

(List continued on next page.)

*Primary Examiner*—Robert A. Wax
*Assistant Examiner*—W. Moore
*Attorney, Agent, or Firm*—Morrison & Foester LLP

[57] ABSTRACT

The present invention provides the cloning and expression of purified and isolated DNA molecules, obtainable from fungi, which encode enzymes having arabinan-degrading activity. The present invention also provides DNA constructs containing these DNA molecules and methods for their enhanced expression in selected microbial host cells. The present invention further provides methods for the use of the thus-produced arabinan-degrading enzymes.

53 Claims, 30 Drawing Sheets

OTHER PUBLICATIONS

Kaji, A., "L–Arabinosidases" *Adv. Carbohydrate Chem. Biochem.* (1984) 42:383–394.

Brillouet et al., "Production, purification, and properties of an α–L–arabinofuranosidase from *Dichomitus squalens*" *Carbohydrate Res.* (1985) 144:113–126.

Rombouts et al., "The arabinanases of *Aspergillus niger*–purification and characterisation of two α–L–arabinofuranosidases and an endo–1,5–α–L–arabinanase" *Carbohydrate Polymers* (1988) 9:25–47.

van der Veen et al., "Induction, purification and characterisation of arabinases produced by *Aspergillus niger*" *Arch. Microbiol.* (1991) 157:23–28.

Gunata et al., "Purification and some properties of an α–L–arabinofuranosidase from *Aspergillus niger*. Action on grape monoterpenyl arabinofuranosylglucosides" *J. Agric. Food Chem.* (1990) 38:772–776.

Schwarz et al., "Xylan degradation by the thermophile clostridium stercorarium: cloning and expression of xylanase, β–D–xylosidase, and αL–arabinofuranosidase genes in *Escherichia coli*" *Biochem. Biophys. Res. Commun.* (1990) 170(1):368–374.

Whitehead et al., "The genes for three xylan–degrading activities from *Bacteriodes ovatus* are clustered in a 3.8–kilobase region" *J. Bacteriol.* (1990) 172(5):2408–24112.

Karimi et al., "Comparative study of some microbial arabinan–degrading enzymes" *J. Indust. Microbiol.* (1989) 4(3):173–180.

Lee et al., "Purification and characterization of an α–L–arabinofuranosidase from *Clostriduim acetobutylicum* ATCC 824" *Can. J. Microbiol.* (1987) 33:1011–1016.

Jaye, M., et al., Nucleic Acids Research, vol. 11, No. 8, "Isolation of a human anti–haemophiliac factor IX cDNA clone using a unique 52–base synthetic oligonucleotide probe deduced from the amino acid sequence of bovine factor IX", pp. 2325–2335, 1983.

Ullrich. A., et al., The EMBO Journal, vol. 3, No. 2, "Isolation of the human insulin–like growth factor I gene using a single synthetic DNA probe", pp. 361–364, 1984.

Lehtovaara, P. M., et al., Protein Engineering, vol. 2, "A new method for random mutagenesis of complete genes: enzymatic generation of mutant libraries in vitro", pp. 63–68., 1988.

Landt, C., et al., Gene, vol. 96, "A general method for rapid site–directed mutagenesis using the polymerase chain reaction", pp. 125–128, 1990.

Kuipers, O. P., et al., Nucleic Acids Research, vol. 19, "Improved site–directed mutagenesis using PCR", p. 4556, 1991.

Zhou, Y., et al., Nucleic Acids Research, vol. 19, "Random mutagenesis of gene–sized DNA molecules by use of PCR with Taq DNA polymerase", p. 6052, 1991.

Zoller, M. J., Current Opinion in Biotechnology, vol. 2, "New molecular biology methods for protein engineering", pp. 526–531, 1991.

Caldwell, R. C., et al., PCR Methods and Applications, vol. 2, "Randomization of genes by PCR mutagenesis", pp. 28–33, 1992.

Sood, A. K., et al., 1981, Proceedings of the National Academy & Sciences, U.S.A., 78(1): 616–620.

Cullen, D., et al., 1987, *Bio/Technology,* 5: 369–376.

Matsuda, G., et al., 1981, *FEBS Letters,* 126(1): 111–113.

Karimi, S., and Ward, O. P., 1989, *Journal of Industrial Microbiology,* 4(3): 173–180.

Poutanen, K., 1988, *Journal of Biotechnology,* 7(4):271–282.

Kelly, M. A., et al., 1987, *Biochemical Journal,* 245(3):843–849.

Tagawa, K., and Kaji, A., 1988, *Methods in Enzymology,* 160: 707–712.

Waibel, R., et al., 1980, *Journal of Chromatography,* 197(1): 86–91.

Frohman, M. A., et al., 1988, *Proceedings of The National Academy of Sciences, U.S.A.,* 85: 8998–9002.

Moos, M. Jr., et al., 1988, *The Journal of Biological Chemistry,* 263(13): 6005–6008.

Amino acid sequence of the N-terminus of A. niger exo B enzyme and nucleotide sequence of the oligonucleotide mixture AB1719 derived from amino acid 4 (Asp) to 11 (Thr) of this sequence.

```
      1                 5                   10                  15
    Gly-Pro-Xaa-Asp-Ile-Tyr-Glu-Ala-Gly-Asp-Thr-Pro-Xaa-Val-Ala-Ala
```

(Formula 1)

```
AB1719:  5'  IGTATCICCIGCTTCATAAATATC  3'
                 G       C   G G G G
```

FIG. 2

Amino acid sequence of the N-terminus of a 15 kDa CNBr fragment of the exo B protein and nucleotide sequence of the oligonucleotide mixture AB2306 derived from amino acid 6 (Ile) to 13 (Asp) of this sequence.

```
                1                   5                      10                      15
        Xaa-Lys-Glu-Xaa-Ala-Ile-Ile-Leu-Gly-Ile-Gly-Gly-Asp-Xaa-Xaa-Asn-Gly-Ala
```

(Formula 3)

AB2306:  5' TCICCICCAATICCIAGAATAAT 3'
                   G         G
                   G

FIG. 3

```
    (i) SEQUENCE CHARACTERISTICS:
        (A) LENGTH: 2753 base pairs
        (B) TYPE: nucleic acid
        (C) STRANDEDNESS: double
        (D) TOPOLOGY: linear
   (ii) MOLECULE TYPE: DNA (genomic)
  (iii) HYPOTHETICAL: NO
   (iv) ANTI-SENSE: NO
   (vi) ORIGINAL SOURCE:
        (A) ORGANISM: Aspergillus niger
   (ix) FEATURE:
        (A) NAME/KEY: CDS
        (B) LOCATION: 161..1660
        (C) IDENTIFICATION METHOD: experimental
        (D) OTHER INFORMATION: /codon_start= 161
            /product= "alpha-L-arabinofuranosidase B"
            /evidence= EXPERIMENTAL
            /gene- "exoB"
   (ix) FEATURE:
        (A) NAME/KEY: sig_peptide
        (B) LOCATION: 161..214
   (ix) FEATURE:
        (A) NAME/KEY: mat_peptide
        (B) LOCATION: 215..1660
```

(Formula 4)

| | | | | | |
|---|---|---|---|---|---|
| GAGCTCGATC | TTGCATTTCA | TGCATAGGCA | CTGACTGCAG | TAAAGAATAT | AAATAAGCCT | 60 |
| CCCTTCGCAC | CCTAGTAGCA | TGATTTCTTT | CTCCAAGCGG | CCTATCTCAC | TGTCTCCTCT | 120 |
| CCTAGCCCAG | AACTTACTGA | GCAGGCAGTA | ATCCTCCACC | ATGTTCTCCC | GCCGAAACCT | 180 |
| CGTCGCCCTA | GGGCTGGCAG | CCACCGTCAG | CGCCGGCCCC | TGTGACATCT | ACGAAGCCGG | 240 |
| CGACACGCCC | TGCGTAGCCG | CGCACAGCAC | CACCCGCGCC | CTATACAGCT | CCTTCAGCGG | 300 |
| CGCCCTCTAC | CAGCTCCAAC | GTGGCTCCGA | CGACACCACC | ACCACCATCT | CCCCGCTCAC | 360 |
| AGCCGGCGGC | GTCGCCGACG | CCTCCGCCCA | AGACACCTTC | TGTGCCAACA | CCACCTGCTT | 420 |
| GATCACCATC | ATCTACGACC | AATCCGGCAA | CGGCAACCAC | CTGACCCAAG | CACCCCCGGG | 480 |
| AGGCTTCGAC | GGCCCCGACG | TCGACGGCTA | CGACAACCTC | GCCAGCGCCA | TCGGCGCCCC | 540 |
| CGTCACCCTC | AATGGCCAAA | AGGCCTACGG | CGTGTTCATG | TCCCCCGGCA | CGGGCTACCG | 600 |
| TAACAACGAA | GCCACCGGCA | CCGCCACCGG | CGACGAACCC | GAAGGCATGT | ACGCCGTCCT | 660 |
| GGACGGCACG | CACTACAACG | ACGCCTGCTG | CTTCGACTAC | GGCAACGCCG | AGACCAGCAG | 720 |
| CACCGACACT | GGCGCCGGCC | ACATGGAGGC | CATCTACCTC | GGGAACAGCA | CCACCTGGGG | 780 |
| CTACGGCGCC | GGTGACGGGC | CCTGGATCAT | GGTCGATATG | GAGAACAACC | TCTTCTCCGG | 840 |

FIG. 5A

```
TGCTGATGAG GGATATAACT CCGGAGATCC CTCGATCAGC TACAGCTTTG TCACTGCCGC    900
GGTCAAGGGC GGGGCTGATA AGTGGGCTAT TCGCGGTGGT AATGCTGCCT CTGGGTCCCT    960
CTCTACTTAC TACAGCGGCG CTCGCCCGGA TTACTCCGGC TATAACCCCA TGAGCAAGGA   1020
GGGCGCTATC ATCCTGGGTA TCGGCGGTGA CAACAGCAAC GGCGCCCAGG GTACCTTCTA   1080
CGAGGGTGTC ATGACCTCCG GCTACCCGTC GGACGATGTC GAGAACTCCG TCCAGGAGAA   1140
CATCGTGGCT GCGAAATACG TCTCCGGCTC GCTGGTCAGC GGCCCGTCGT TCACCTCCGG   1200
AGAGGTGGTC TCGCTGCGTG TCACTACCCC CGGTTACACG ACGCGGTATA TTGCGCACAC   1260
TGACACCACT GTGAACACGC AGGTCGTGGA CGACGATAGT TCCACCACGC TGAAGGAGGA   1320
GGCTAGCTGG ACCGTGGTGA CAGGTCTGGC TAATAGTCAG TGCTTCTCGT TCGAGTCGGT   1380
TGATACCCCT GGTAGCTATA TCCGGCATTA CAACTTTGAG TTGCTGCTTA ATGCCAACGA   1440
TGGCACGAAG CAGTTCCATG AGGATGCTAC TTTCTGTCCT CAGGCGCCGT TGAATGGAGA   1500
AGGTACTTCG TTGAGATCGT GGAGTTATCC GACCAGGTAT TTCAGGCATT ATGAGAATGT   1560
CCTGTATGCT GCTAGTAATG GTGGTGTGCA GACGTTTGAT TCCAAGACGT CGTTTAATAA   1620
TGATGTTAGC TTTGAGATTG AGACGGCGTT TGCTTCGTAA GGGGGGAATT GGGGGTTGTT   1680
TGGTGGTTTG GGTGTGGGGT TGTATCTGCC TGTGTTGGCG GGGAGAGTGG TTTGTAAATA   1740
GGTCATTTTT GGTATATAGC ATACGAATAC TATACGATAG TATACATGAT AGTGGTTGTT   1800
TCATGTAATC GAGAAATTAT TCAAGGCTTG CAATACAATA TCTTATTACT GTATCTCGTG   1860
GAGCATTCAC AGACTGAACG GCTGCACAAT GATTCTTATG CGGTGATATT GACTGTGATT   1920
AGATGATATA TTCAGGTGTG CTATTTTTCT TGTATTTATG CTTCATGCGA ATATATGTAT   1980
TTCACGACAG ACAGAGAGGT TAAACAAAGC ATACTAACGA GCGATTCAGA TATGGCATGT   2040
ATGAATAAGA CAAAAGTACT GCGACACTCA AGACCAACAC AAACCAGTAT ACTTCATAAC   2100
AATATATGCT AGGCAGTACC TCCGATTCTA CGATGAGCTT TACCAGAAAA TGGATTTCTT   2160
TGTCCCTCGT CATTCTCAAT TTTTGGGCCT TCCACGGCTG CGGCAACCTG TTGAGCAAGA   2220
CGTGTTCTCT CGTACGGATG GACGTTGATC TTCTTCTCGA GCAGGTCCAA TTGCTCTTTC   2280
TCCAAATGGC GGACTCTGAC CTCACCGGAG GAATCACTCG GCAAGCATAT CTGGTAAGTC   2340
GCTGAAAATT TCTTCTCGAA ACTGGCGTAG CTTGGTGGCC ACTGCGGGAA GCGTCGGAAG   2400
TATTTGCCTG TCCAGACGGT CAATATGAAT GAGTCGGATA CTTCAATGCC CGCCTGCCTT   2460
CTACGGTCGA AGAAATGCTG GCCGATGCTT CTCACGGAGG CATAGTTTAT AACAGGCTTG   2520
ATGGGGTTTT GTATGTCGAG GAGACCTAAT TCAAAGTGCA TAGATAGGCT CCTGAGATTG   2580
TGAAAACCGG TTGCTAGTTT GTCGAAGACG TCGTTGGGCT GTTGTGTGGT TATAGTTCAG   2640
TTCATGGGAT GTACTAAGAG GATTCTTTGG CTTACCCATT GATCGTTCTC TCTCTTGACT   2700
CCCACCTGCA GTGACTTCAG TTTGGGACAG CTAACATCGA GGTGGCTGAG CTC          2753
```

FIG. 5B (i) SEQUENCE CHARACTERISTICS:
    (A) LENGTH: 499 amino acids
    (B) TYPE: amino acid
    (D) TOPOLOGY: linear (ii) MOLECULE TYPE: protein (Formula 5)

```
Met Phe Ser Arg Arg Asn Leu Val Ala Leu Gly Leu Ala Ala Thr Val
-18         -15             -10                 -5

Ser Ala Gly Pro Cys Asp Ile Tyr Glu Ala Gly Asp Thr Pro Cys Val
    -1  +1          5                   10

Ala Ala His Ser Thr Thr Arg Ala Leu Tyr Ser Ser Phe Ser Gly Ala
15              20                  25                      30

Leu Tyr Gln Leu Gln Arg Gly Ser Asp Thr Thr Thr Ile Ser
            35                  40                  45

Pro Leu Thr Ala Gly Gly Val Ala Asp Ala Ser Ala Gln Asp Thr Phe
            50                  55                  60

Cys Ala Asn Thr Thr Cys Leu Ile Thr Ile Ile Tyr Asp Gln Ser Gly
        65                  70                  75

Asn Gly Asn His Leu Thr Gln Ala Pro Pro Gly Gly Phe Asp Gly Pro
    80                  85                  90

Asp Val Asp Gly Tyr Asp Asn Leu Ala Ser Ala Ile Gly Ala Pro Val
95              100                 105                     110

Thr Leu Asn Gly Gln Lys Ala Tyr Gly Val Phe Met Ser Pro Gly Thr
                115                 120                 125

Gly Tyr Arg Asn Asn Glu Ala Thr Gly Thr Ala Thr Gly Asp Glu Pro
            130                 135                 140

Glu Gly Met Tyr Ala Val Leu Asp Gly Thr His Tyr Asn Asp Ala Cys
        145                 150                 155

Cys Phe Asp Tyr Gly Asn Ala Glu Thr Ser Ser Thr Asp Thr Gly Ala
        160                 165                 170

Gly His Met Glu Ala Ile Tyr Leu Gly Asn Ser Thr Thr Trp Gly Tyr
175                 180                 185                 190

Gly Ala Gly Asp Gly Pro Trp Ile Met Val Asp Met Glu Asn Asn Leu
            195                 200                 205

Phe Ser Gly Ala Asp Glu Gly Tyr Asn Ser Gly Asp Pro Ser Ile Ser
            210                 215                 220
```

FIG. 6A

```
Tyr Ser Phe Val Thr Ala Ala Val Lys Gly Gly Ala Asp Lys Trp Ala
    225                     230             235
Ile Arg Gly Gly Asn Ala Ala Ser Gly Ser Leu Ser Thr Tyr Tyr Ser
    240             245                 250
Gly Ala Arg Pro Asp Tyr Ser Gly Tyr Asn Pro Met Ser Lys Glu Gly
255             260             265                     270
Ala Ile Ile Leu Gly Ile Gly Gly Asp Asn Ser Asn Gly Ala Gln Gly
            275             280                     285
Thr Phe Tyr Glu Gly Val Met Thr Ser Gly Tyr Pro Ser Asp Asp Val
        290             295             300
Glu Asn Ser Val Gln Glu Asn Ile Val Ala Ala Lys Tyr Val Ser Gly
        305             310             315
Ser Leu Val Ser Gly Pro Ser Phe Thr Ser Gly Glu Val Val Ser Leu
    320             325             330
Arg Val Thr Thr Pro Gly Tyr Thr Thr Arg Tyr Ile Ala His Thr Asp
335             340             345             350
Thr Thr Val Asn Thr Gln Val Val Asp Asp Asp Ser Ser Thr Thr Leu
            355             360             365
Lys Glu Glu Ala Ser Trp Thr Val Val Thr Gly Leu Ala Asn Ser Gln
            370             375             380
Cys Phe Ser Phe Glu Ser Val Asp Thr Pro Gly Ser Tyr Ile Arg His
        385             390             395
Tyr Asn Phe Glu Leu Leu Leu Asn Ala Asn Asp Gly Thr Lys Gln Phe
    400             405             410
His Glu Asp Ala Thr Phe Cys Pro Gln Ala Pro Leu Asn Gly Glu Gly
415             420             425             430
Thr Ser Leu Arg Ser Trp Ser Tyr Pro Thr Arg Tyr Phe Arg His Tyr
            435             440             445
Glu Asn Val Leu Tyr Ala Ala Ser Asn Gly Gly Val Gln Thr Phe Asp
            450             455             460
Ser Lys Thr Ser Phe Asn Asn Asp Val Ser Phe Glu Ile Glu Thr Ala
        465             470             475
Phe Ala Ser
        480
```

FIG. 6B

```
    (i) SEQUENCE CHARACTERISTICS:
        (A) LENGTH: 3958 base pairs
        (B) TYPE: nucleic acid
        (C) STRANDEDNESS: double
        (D) TOPOLOGY: linear
   (ii) MOLECULE TYPE: DNA (genomic)
  (iii) HYPOTHETICAL: NO
   (iv) ANTI-SENSE: NO
   (vi) ORIGINAL SOURCE:
        (A) ORGANISM: Aspergillus niger
   (ix) FEATURE:
        (A) NAME/KEY: exon
        (B) LOCATION: 1247..1390
   (ix) FEATURE:
        (A) NAME/KEY: intron
        (B) LOCATION: 1391..1442
   (ix) FEATURE:
        (A) NAME/KEY: exon
        (B) LOCATION: 1443..1957
   (ix) FEATURE:
        (A) NAME/KEY: intron
        (B) LOCATION: 1958..2005
   (ix) FEATURE:
        (A) NAME/KEY: exon
        (B) LOCATION: 2006..2089
   (ix) FEATURE:
        (A) NAME/KEY: intron
        (B) LOCATION: 2090..2137
   (ix) FEATURE:
        (A) NAME/KEY: exon
        (B) LOCATION: 2138..2214
   (ix) FEATURE:
        (A) NAME/KEY: intron
        (B) LOCATION: 2215..2262
   (ix) FEATURE:
        (A) NAME/KEY: exon
        (B) LOCATION: 2263..2295
   (ix) FEATURE:
        (A) NAME/KEY: intron
        (B) LOCATION: 2296..2346
   (ix) FEATURE:
        (A) NAME/KEY: exon
        (B) LOCATION: 2347..2498

(ix) FEATURE:
        (A) NAME/KEY: intron
        (B) LOCATION: 2499..2548
   (ix) FEATURE:
        (A) NAME/KEY: exon
        (B) LOCATION: 2549..3037
   (ix) FEATURE:
        (A) NAME/KEY: intron
        (B) LOCATION: 3038..3092
   (ix) FEATURE:
        (A) NAME/KEY: exon
        (B) LOCATION: 3093..3485
```

FIG. 14A (ix) FEATURE
    (A) NAME/KEY: CDS
    (B) LOCATION: join(1247..1390, 1443..1957,
        2006..2089, 2138..2214, 2263..2295,
        2347..2498, 2549..3037, 3093..3485)
    (C) IDENTIFICATION METHOD: experimental
    (D) OTHER INFORMATION: /codon_start= 1247
        /product= "alpha-L-arabinofuranosidase A"
        /evidence= EXPERIMENTAL
        /gene= "exoA"
(ix) FEATURE:
    (A) NAME/KEY: sig_peptide
    (B) LOCATION: 1247..1321
(ix) FEATURE:
    (A) NAME/KEY: mat_peptide
    (B) LOCATION: 1322..3485

(Formula 20)

```
AAGGGACTGA CTGAACTCAG TGAGATGTGC CGCGAAGTAA CTAAGCGCTG TGCCTGCAGT    60
GAGGCGTGAT GGAACACTGC ATCCGATCTC CAAGACCCCG ATATGAACCT TAATGACAAT   120
GGTCTAAGTT TTTTTGTCAT CTCGCATAGC ACGGTAGGCG ACTAAGTTGA AGGATAAAGA   180
GAGCAGGATT AGGATGGCTC GAGATCAAAT TGAAAGTAAT AGAGTAACAG GGGAAAACTC   240
TAACAGTTGG CTATGACGAA GGTGGCAGCG ACTTCCCGGA GAGAGATTAA GCCGGGTAGA   300
ACCAAGGGAC GGCTGTGGCT GGATCAGGAA CCCAAATCTA TTCCAGTATC GGAGGATACT   360
CAGGGGTCCC GCCGGGGTTT TCCCTTGATC GGAGAACATC AACCACATCA AAATGCGGAG   420
TAACGATGAG GGGGAAGTGC ACGGCCGACG TCAGAGTTTC GCTTGGGTGG ATCTGCAATG   480
TTTAGGCGGC CGACTAGACC GACAGTCCAG CACCTGCCCT GGGAGTTCAA GACAGTGGTT   540
TGACCATCTT TTGAGAAGAC TGAAATTCCC GTAGATTCCA TCAAGATTAT TCATGTATCA   600
CTAGCGACTC AGCACTGGGT AAGCTGCACC CACGGATTTT CTCAGCTATC TGAATGTATC   660
AGAGACAAAG ATCTTCGTGG ATGGAGCCCA TCAACCGAGC TTTAATGCGC CAAACCTACT   720
GTATGACTGA ATAATGGATG GATCGGCATG TCGTACGATC GGGTAAGGGT CCTAAAAATG   780
GAGGGCCGGG GAATTCTGGG GTTAGCCGTC GGGATTATTT CGGTACGACA AACTCACTGT   840
TCACTTTGAT CTCGGCGTGG TTGCGGCTAA AAAGATGACC TTGAAGGTGG AGCGAACAAC   900
TGGAGGTGCT CGGAGGGACG CGGAGAAGAG AGGATCCAAG ACATCGGGGC AGGGAAGTCC   960
ATGCCGCGTG CAGTCACGCT TTTCCTCCCT CTGCTCTCTT CTCCTCCACA TTCCACATTC  1020
CACCTCCACA CTCCTCCACT CTTCCTCTGG CACCTTCCTC TTCCTCGATT TCTTGGCTTC  1080
```

FIG. 14B

```
TCGGTTGATT GTCTTCGACC TCGTTGCGAT GACCCCACCG CATTTTCTGC TGCCTTGGCC   1140
TGTCTGATGC CCCGGTTAAT TTCACGAAAG TCCGGTCATA AAAGGCGTTG TATCCTCCCT   1200
TTGCAACAAT GACACCAGGC TCAGCTTCCT CCAGACAGCC GGCAACATGG TGGCCTTTTC   1260
AGCTCTTTCG GGCGTCAGCG CCGTTTCTTT ACTACTATCC CTCGTTCAAA ATGCACACGG   1320
AATCTCCTTG AAGGTCTCCA CCCAGGGTGG CAACTCATCC AGCCCCATCC TATATGGCTT   1380
CATGTTTGAG GTAGGCCGCA GACTAAGCAG TAAAAGACAA TTGGTTCTCT GACGGTGATT   1440
AGGATATCAA TCACTCAGGA GATGGAGGAA TTTATGGGCA AATGCTGCAG AACCCTGGCC   1500
TTCAGGGAAC GGCGCCTAAT CTGACTGCCT GGGCGGCTGT CGGTGACGCT ACCATCGCCA   1560
TTGATGGCGA CAGTCCATTG ACCTCTGCCA TCCCCAGCAC CATCAAGCTT AATATTGCGG   1620
ACGATGCTAC CGGTGCGGTG GGTCTCACCA ATGAGGGATA TTGGGGCATC CCAGTCGATG   1680
GCAGCGAATT CCATAGTTCC TTCTGGATAA AGGGAGATTA CTCCGGCGAC ATCACCGTCC   1740
GACTGGTTGG AAACTACACC GGCACGGAGT ACGGCTCTAC CACTATCACC CATACGTCCA   1800
CAGCAGACAA CTTCACCCAA GCCTCCGTCA AGTTCCCCAC CACCAAGGCT CCAGATGGCA   1860
ACGTTTTGTA CGAGCTCACA GTTGATGGAA GCGTGGCTGC TGGCTCGTCT TTGAACTTCG   1920
GCTACTTGAC GCTTTTTGGC GAAACCTATA AGTCAAGGTT TGCTTCCCTA TACTCCGAAG   1980
AGTGAATTAG GGCTAATTG TGTAGGGAAA ATGGCCTGAA GCCCCAGCTT GCCAATGTGT   2040
TGGATGATAT GAAAGGATCC TTCCTGAGAT TTCCCGGCGG TAACAACCTG TAAGTCTCAG   2100
CTCGCCCGGT AAGTGTATAG AAGCTCATCA GAGGTAGTGA GGGAAACAGC GCAGAAAACC   2160
GCTGGAAGTG GAACGAGACA ATCGGCGATC TTTGTGATCG TCCCGGACGT GAAGGTATGT   2220
CTCATTATTA GGATTGAAGC ATTCATCCCT GACGGTATAT AGGCACTTGG ACTTACTATA   2280
ACACCGACGG ACTGGGTAAG TAAAGGGCTA TATACAAGTA CCTAGATACT GTACTAACGC   2340
TTGTAGGCCT TCACGAATAC TTTTACTGGT GTGAGGATTT GGGGCTCGTA CCGGTGCTCG   2400
GTGTCTGGGA TGGGTTCGCT CTGGAGTCGG GTGGCAACAC CCCCCTCACG GGCGACGCAC   2460
TGACCCCTTA TATCGACGAT GTCTTGAACG AGCTCGAGGT ATGTTGAGCG GCATATCAAA   2520
TTGATAGCTG AAGCTAACCC ATTGGCAGTA CATCTTGGGT GATACGAGCA CGACCTATGG   2580
AGCGTGGCGC GCGGCAAACG GACAGGAGGA GCCGTGGAAC CTTACCATGG TCGAGATTGG   2640
CAATGAGGAC ATGCTGGGAG GCGGATGCGA GTCCTACGCG GAACGTTTCA CTGCCTTCTA   2700
```

FIG. 14C

```
TGATGCGATT CATGCTGCTT ATCCGGACCT TATCCTGATT GCCAGCACCA GCGAGGCGGA    2760
TTGCTTGCCC GAGTCAATGC CCGAGGGTAG CTGGGTCGAC TACCACGACT ACAGCACGCC    2820
TGATGGACTG GTGGGCCAGT TCAACTACTT CGACAATTTA AACCGCTCGG TACCATACTT    2880
CATCGGCGAG TACTCGCGCT GGGAGATTGA CTGGCCCAAC ATGAAGGGAT CGGTCGCTGA    2940
AGCCGTCTTC ATGATCGGGT TCGAGAGGAA CAGCGACGTG GTGAAGATGG CGGCGTATGC    3000
GCCTTTGCTC CAGCTAATCA ACTCGACTCA GTGGACGGTA AGTCACGACT GAGCAGCGGG    3060
GTTTCAGGTA TGAATGAGCT AACGAGTGGT AGCCGGACCT GATCGGATAC ACGCAGTCAC    3120
CCGGTGACAT TTTCCTGTCG ACCAGCTACT ACGTGCAGGA GATGTTCTCG CGCAACCGGG    3180
GTGATACAAT TAAGGAGGTG ACGTCGGACA GCGACTTCGG ACCGTTGTAC TGGGTTGCGT    3240
CGAGCGCCGG GGACTCGTAC TACGTGAAGC TGGCCAACTA TGGCTCCGAG ACGCAAGACC    3300
TCACGGTGAG CATCCCAGGA ACGAGCACAG GCAAGTTGAC GGTGCTGGCG GACAGTGATC    3360
CGGATGCGTA TAACTCGGAC ACCCAGACGC TGGTCACGCC GAGTGAATCG ACGGTGCAGG    3420
CGAGCAATGG CACTTTTACC TTTAGTTTGC CGGCATGGGC GGTGGCTGTC CTGGCGGCGA    3480
ACTAGCGTTG ATTGGGGCGA GCTCGTATGG GCGGCAAGTC GAATATTATC TGCAGGTGTG    3540
GTGTCATGTA CTGCAGTATT TCTGATTAAC GATAGAGAGA TAGATCCATG CTATATACCT    3600
GCTTGTATAT CCAAGGCATT TATCCAATGA TAGGCAACGC CACCACACGT GGCTATGCAC    3660
ATACTAGTCA GGAGGTAGTA GAGTGACTGA CTGCTATGTA GCGGTCGGCC GGGGATAGCA    3720
GTTGAATGAC CCCAATTAAC AGAACCGCCT GACTCTCCAA CGTGTACCTC TAGGTTATTT    3780
TATATTTCTT GTTAAAGCCC CCCAGAAACA CAACCGAAGA ATCAATGGAT GCGATGAAAA    3840
CAAGGCACTG GTAAGCGAAG GAGGGAAAAA CAAGCGGATT GGTTGGTTGT GGCCCGATGC    3900
AAACGGGCGG CCTCTCCACT CGAATTGGAC AGAAGCGAAG GCCGTGCGCC GAGACGGG     3958
```

FIG. 14D (i) SEQUENCE CHARACTERISTICS:
    (A) LENGTH: 628 amino acids
    (B) TYPE: amino acid
    (D) TOPOLOGY: linear
(ii) MOLECULE TYPE: protein (Formula 21)

```
Met Val Ala Phe Ser Ala Leu Ser Gly Val Ser Ala Val Ser Leu Leu
-24         -20                 -15                 -10

Leu Ser Leu Val Gln Asn Ala His Gly Ile Ser Leu Lys Val Ser Thr
            -5              -1  +1              5

Gln Gly Gly Asn Ser Ser Pro Ile Leu Tyr Gly Phe Met Phe Glu
    10              15                  20

Asp Ile Asn His Ser Gly Asp Gly Ile Tyr Gly Gln Met Leu Gln
25              30                  35                      40

Asn Pro Gly Leu Gln Gly Thr Ala Pro Asn Leu Thr Ala Trp Ala Ala
                45              50                  55

Val Gly Asp Ala Thr Ile Ala Ile Asp Gly Asp Ser Pro Leu Thr Ser
            60                  65                  70

Ala Ile Pro Ser Thr Ile Lys Leu Asn Ile Ala Asp Asp Ala Thr Gly
        75              80                  85

Ala Val Gly Leu Thr Asn Glu Gly Tyr Trp Gly Ile Pro Val Asp Gly
    90              95                  100

Ser Glu Phe His Ser Ser Phe Trp Ile Lys Gly Asp Tyr Ser Gly Asp
105             110             115                     120

Ile Thr Val Arg Leu Val Gly Asn Tyr Thr Gly Thr Glu Tyr Gly Ser
                125             130             135

Thr Thr Ile Thr His Thr Ser Thr Ala Asp Asn Phe Thr Gln Ala Ser
            140             145                 150

Val Lys Phe Pro Thr Thr Lys Ala Pro Asp Gly Asn Val Leu Tyr Glu
        155             160                 165

Leu Thr Val Asp Gly Ser Val Ala Ala Gly Ser Ser Leu Asn Phe Gly
    170             175                 180

Tyr Leu Thr Leu Phe Gly Glu Thr Tyr Lys Ser Arg Glu Asn Gly Leu
185                 190             195                     200

Lys Pro Gln Leu Ala Asn Val Leu Asp Met Lys Gly Ser Phe Leu
                205             210                 215

Arg Phe Pro Gly Gly Asn Asn Leu Glu Gly Asn Ser Ala Glu Asn Arg
            220             225                 230
```

FIG. 15A

```
Trp Lys Trp Asn Glu Thr Ile Gly Asp Leu Cys Asp Arg Pro Gly Arg
        235                 240                 245
Glu Gly Thr Trp Thr Tyr Tyr Asn Thr Asp Gly Leu Gly Leu His Glu
    250                 255                 260
Tyr Phe Tyr Trp Cys Glu Asp Leu Gly Leu Val Pro Val Leu Gly Val
265                 270                 275                 280
Trp Asp Gly Phe Ala Leu Glu Ser Gly Gly Asn Thr Pro Leu Thr Gly
                285                 290                 295
Asp Ala Leu Thr Pro Tyr Ile Asp Asp Val Leu Asn Glu Leu Glu Tyr
            300                 305                 310
Ile Leu Gly Asp Thr Ser Thr Thr Tyr Gly Ala Trp Arg Ala Ala Asn
            315                 320                 325
Gly Gln Glu Glu Pro Trp Asn Leu Thr Met Val Glu Ile Gly Asn Glu
        330                 335                 340
Asp Met Leu Gly Gly Gly Cys Glu Ser Tyr Ala Glu Arg Phe Thr Ala
345                 350                 355                 360
Phe Tyr Asp Ala Ile His Ala Ala Tyr Pro Asp Leu Ile Leu Ile Ala
                365                 370                 375
Ser Thr Ser Glu Ala Asp Cys Leu Pro Glu Ser Met Pro Glu Gly Ser
            380                 385                 390
Trp Val Asp Tyr His Asp Tyr Ser Thr Pro Asp Gly Leu Val Gly Gln
        395                 400                 405
Phe Asn Tyr Phe Asp Asn Leu Asn Arg Ser Val Pro Tyr Phe Ile Gly
        410                 415                 420
Glu Tyr Ser Arg Trp Glu Ile Asp Trp Pro Asn Met Lys Gly Ser Val
425                 430                 435                 440
Ala Glu Ala Val Phe Met Ile Gly Phe Glu Arg Asn Ser Asp Val Val
                445                 450                 455
Lys Met Ala Ala Tyr Ala Pro Leu Leu Gln Leu Ile Asn Ser Thr Gln
            460                 465                 470
Trp Thr Pro Asp Leu Ile Gly Tyr Thr Gln Ser Pro Gly Asp Ile Phe
        475                 480                 485
Leu Ser Thr Ser Tyr Tyr Val Gln Glu Met Phe Ser Arg Asn Arg Gly
        490                 495                 500
Asp Thr Ile Lys Glu Val Thr Ser Asp Ser Asp Phe Gly Pro Leu Tyr
505                 510                 515                 520
```

FIG. 15B

```
Trp Val Ala Ser Ser Ala Gly Asp Ser Tyr Tyr Val Lys Leu Ala Asn
            525             530             535

Tyr Gly Ser Glu Thr Gln Asp Leu Thr Val Ser Ile Pro Gly Thr Ser
            540             545             550

Thr Gly Lys Leu Thr Val Leu Ala Asp Ser Asp Pro Asp Ala Tyr Asn
            555             560             565

Ser Asp Thr Gln Thr Leu Val Thr Pro Ser Glu Ser Thr Val Gln Ala
    570             575             580

Ser Asn Gly Thr Phe Thr Phe Ser Leu Pro Ala Trp Ala Val Ala Val
585             590             595                         600

Leu Ala Ala Asn
            604
```

FIG. 15C

```
(i)    SEQUENCE CHARACTERISTICS:
       (A)  LENGTH: 3147 base pairs
       (B)  TYPE: nucleic acid
       (C)  STRANDEDNESS: double
       (D)  TOPOLOGY: linear
(ii)   MOLECULE TYPE: DNA (genomic)
(iii)  HYPOTHETICAL: NO
(iv)   ANTI-SENSE: NO
(vi)   ORIGINAL SOURCE:
       (A)  ORGANISM: Aspergillus niger
(ix)   FEATURE:
       (A)  NAME/KEY: exon
       (B)  LOCATION: 1178..1444
(ix)   FEATURE:
       (A)  NAME/KEY: intron
       (B)  LOCATION: 1445..1494
(ix)   FEATURE:
       (A)  NAME/KEY: exon
       (B)  LOCATION: 1495..1971
(ix)   FEATURE:
       (A)  NAME/KEY: intron
       (B)  LOCATION: 1972..2030
(ix)   FEATURE:
       (A)  NAME/KEY: exon
       (B)  LOCATION: 2031..2116
(ix)   FEATURE:
       (A)  NAME/KEY: intron
       (B)  LOCATION: 2117..2167
(ix)   FEATURE:
       (A)  NAME/KEY: exon
       (B)  LOCATION: 2168..2378
(ix)   FEATURE:
       (A)  NAME/KEY: CDS
       (B)  LOCATION: join(1178..1444, 1495..1971,
            2031..2116, 2168..2378)
       (C)  IDENTIFICATION METHOD: experimental
       (D)  OTHER INFORMATION: /codon_start= 1178
            /product= "endo 1,5-alpha-arabinanase"
            /evidence= EXPERIMENTAL
            /gene- "abnA"
(ix)   FEATURE:
       (A)  NAME/KEY: sig_peptide
       (B)  LOCATION: 1178..1234
(ix)   FEATURE:
       (A)  NAME/KEY: mat_peptide
       (B)  LOCATION: 1235..2378
```

(Formula 22)

FIG. 19A

```
AAGCTTGGTC GTGTCCGCGG TAGTACTACC TCCGTAGAGA CTCTCTCTGG ATCTTCTCAA    60
AAGGGGGTTT CGTGTTCTGG TACAGACTCT TCTAGTTCTC GCTTACGGCT CCACCCATTG   120
CTGAAGAACC CCACTCCTGC TGTTTCCCAT TTATGTTCCG GTCTAACGAT GGCTTCTCCA   180
CCAAGAAATG GAAGTGTGCT CTCCTCTCAA AACTCTCCAA TTCTGGTTTG ATCGATGTGA   240
GCTTACCAAG AAAGAGCGAA GACTTCCATC TTGTACTTAC GGACCCGATT AGCTATGCTT   300
CCTACACGTT NAANGACGAT NGACATATNN TGCTACCTGT TACTTGTCAG ATGGTCTCTC   360
TAACGCTGGC GGNATGTGGA CCAGATTCTC TTCAAAGTTA TGCCAAGATT CGCATGGGCC   420
AATCCTGAAA AGCGAAAAGC GCAAGGAGGC GCAGCTGAGA CAGAATCCCC TTTCTGCGAG   480
TCACATCTCG AGTCCCTTAA GGCCACCGTC GAGTGGTGGG CGATAAACTC CGCATATCTG   540
CCACCTGAAA AATATCGGTC AATACATCTA TGGCCTAATG AGACCAGTGG TCAGAATACG   600
CCTAAGGCCG GAAACTACTC CCGCAAATTG CTGCGACGAA GACGAGGGGG GCGTAGTCAT   660
AAATTTGCGT GTCGTGTGCC TATGATAATT TCTTGGGGTC CGAAGAGCAC GCTAGGGATG   720
TCAGAACAAC TAATGTTGCA GGATTGGTCT CCATCTCATC CCTGTCACTG ACATCATATT   780
ACTTCCTAGT ATATCATGTT CACCATTGTA TAGAGAGACG CGCCCATCGC AACGCACGTG   840
TTGGTGAGCA CCTCCACTAA AAGTGTCACT GTTGTCTACA CACCACTCGT TTCACGCTGA   900
TGTGCCGAAT CATACTACAT GCATCGGCCA TCGGCTTATA CCACCAGGTG CCTCCGGAAT   960
TTTGCTGTTT CAAAATGTTC TTTGTAACTC CCTGAAACGA CCAAAGTATC ACGGAGGTAG  1020
CTCCGGACAG GCGGAAAACA CAACCACTTT GTCCACGAAT CGACACAGTA GTCTTCCGGT  1080
GGGTTTAGTT GTCGCTTCAT GATAGTATAT ATAGTAATAG TAGATCTGGA TGCTTGGGAT  1140
AAGTCATCCA GTGGTGACAG CGCCTACCTA AATCGTCATG TATCAACTCC TATCAGTTGC  1200
CTCGGTTCCT CTGCTGGCCA GCCTCGTGCA TGGCTATGCT GACCCCGGAG CATGCTCGGG  1260
TGTTTGTACC ACCCATGACC CCGGTTTGAT CCGGAGAGAG TCGGACGGTA CATACTTCCT  1320
CTTCTCTACA GGAAACAAAA TCTCCTACGT CTCTGCATCA TCCATCGAAG GACCATGGAC  1380
CAGCGTTGGG TCTATGCTGC CGGATGGATC GTCCATCGAC CTCGATGGCA ACGATGATCT  1440
TTGGGTAACT ATGTCCCACT GCAAACATGA TTGGCCTGTC TGACACTAGC CCAGGCCCCG  1500
GATGTCTCCT ATGTAGATGG TCTCTATTAT GTATACTACG CTGTGTCGAC CTTTGGATCC  1560
CAAGATTCCG CCATCGGACT TGCAACGTCC GAGACGATGG AATATGGCTC TTGGACGGAT  1620
CATGGCTCCA CTGGCATTGC GTCTTCCTCA GCCAAGATTT ATAATGCGAT CGACCCCAAC  1680
```

FIG. 19B

```
CTGATCTACG CCGATGGCAC CTACTACATC AACTTTGGGT CGTTCTGGGA TGACATTTAC   1740
CAAGTCCCGA TGAAGTCGAC CCCAACGGCA GCTGCCTCTT CCTCCTACAA TCTTGCGTAT   1800
GACCCGTCGG GTACCCATGC GGAGGAGGGT TCCTATATGT TTCAGTACGG TGACTACTAC   1860
TACCTCTTTT ACTCGGCAGG TATCTGCTGT GGATACGATA CATCCATGCC CGCTTCCGGA   1920
GAGGAGTATC ATATCAAGGT CTGCCGTTCG ACTTCGCCCA CGGGTGATTT CGTAAGTATA   1980
TCCGACATTT AGAGAAAATA CTAAGTAGGG AAAGCTAACC TGGTGCTAAG GTTGACTCCG   2040
ACGGTACGGC GTGCACGGAT GGCGGGGGCA CGATGGTGCT CGAAAGCCAT GGAGAAGTCT   2100
ATGGCCCTGG CGGACAGTAA GTGATTCTGC AGCTGCCCCA CCGATATTTA TGCTTATCAT   2160
GTTTTAGGGG TGTGTATGAC GATCCCAACC TTGGTCCGGT TCTTTACTAC CACTACATGA   2220
ACACCACGAT TGGATACGCG GATTCTGACG CGCAGTTTGG GTGGAACACG ATCGACTTCT   2280
CTGACGGATG GACCGGTTGT ATAAGCATCT TGGTTGGCGA TGGAAATGGT GCTGCCTACG   2340
AGAGGGTCTA CAAGTTGTAT ATAGGATTGC GGCTATGAAC TCGGCCGAGA TATAGTTAGT   2400
TAGTAACTAC ATAGTGGAAT CGTTAGTCAC TAATGCAGCC CGCATGAGTG CTCTGCCTGA   2460
GGCTTCAGTA CTGTCCCTCA ATTTCTGTTT CTGTTTTTAG TTTAAGCTCT GCAGCTGCTC   2520
CCCACCCATT CATCCACTCA TTTGGTGAAG ACATTCATTC TTCCCTTCAA CCACTCTATT   2580
AGAGCATTTC CATCTTCTCA CACTGATCAT CGTAATGCAG ATTCAAGATC AGTTTGGATT   2640
GAGATCCCTA CTGCATGCAC TGTGTGCGTG ACAGAAGCTG GAACTGGTAC TCGCTCGATC   2700
CGTGCAGCGC GAGTCAGTCA CATCCGCCCT GCGCTTCAGA CTAGCCTGCC AATAGTGACT   2760
ATCACAAGGG CCGTACTAAG ATCGAATAAC AGCTTTCCTA ACAACATCGC GTTAACGTGT   2820
TACTTTCCTC CAGCTTACAT TTTGCTATTG AAGCCATATA CGATCCCTTC GATGCGCTCG   2880
GTTTAACTTC TGCCACGATC ACCCGTTCAT CGAAGATTCT GGGAGTCTGT CGGTCTTCAT   2940
GCCAGCAAAG ATCGACTCAA ATACACACAG TCAGCAACAT CTGTTGCTTG TTACGGATGG   3000
TGCCTATTAT AATGCATGAA TAGGGGACCA AGCAATTCTC CGCTGTCGGC GATGTTGAAT   3060
TAAGGAGGGA TAATATTTGA TCGAATGACA AAGGGAAGAA TTGTGCGACA CGAGGGAACC   3120
TTATACTTGT CTACGGCCTA GCAGCAA                                      3147
```

FIG. 19C (i) SEQUENCE CHARACTERISTICS:
    (A) LENGTH: 346 amino acids
    (B) TYPE: amino acid
    (C) STRANDEDNESS: single
    (D) TOPOLOGY: linear
(ii) MOLECULE TYPE: protein (Formula 23)

```
Met Tyr Gln Leu Leu Ser Val Ala Ser Val Pro Leu Leu Ala Ser Leu
-19          -15              -10                  -5

Val His Gly Tyr Ala Asp Pro Gly Ala Cys Ser Gly Val Cys Thr Thr
    -1  +1              5                   10

His Asp Pro Gly Leu Ile Arg Arg Glu Ser Asp Gly Thr Tyr Phe Leu
    15              20                  25

Phe Ser Thr Gly Asn Lys Ile Ser Tyr Val Ser Ala Ser Ser Ile Glu
30              35              40                  45

Gly Pro Trp Thr Ser Val Gly Ser Met Leu Pro Asp Gly Ser Ser Ile
            50              55              60

Asp Leu Asp Gly Asn Asp Asp Leu Trp Ala Pro Asp Val Ser Tyr Val
            65              70                  75

Asp Gly Leu Tyr Tyr Val Tyr Tyr Ala Val Ser Thr Phe Gly Ser Gln
        80              85              90

Asp Ser Ala Ile Gly Leu Ala Thr Ser Glu Thr Met Glu Tyr Gly Ser
    95              100             105

Trp Thr Asp His Gly Ser Thr Gly Ile Ala Ser Ser Ser Ala Lys Ile
110             115             120             125

Tyr Asn Ala Ile Asp Pro Asn Leu Ile Tyr Ala Asp Gly Thr Tyr Tyr
            130             135             140

Ile Asn Phe Gly Ser Phe Trp Asp Asp Ile Tyr Gln Val Pro Met Lys
            145             150             155

Ser Thr Pro Thr Ala Ala Ala Ser Ser Ser Tyr Asn Leu Ala Tyr Asp
        160             165             170

Pro Ser Gly Thr His Ala Glu Glu Gly Ser Tyr Met Phe Gln Tyr Gly
    175             180             185

Asp Tyr Tyr Tyr Leu Phe Tyr Ser Ala Gly Ile Cys Cys Gly Tyr Asp
190             195             200             205

Thr Ser Met Pro Ala Ser Gly Glu Glu Tyr His Ile Lys Val Cys Arg
            210             215             220
```

FIG. 20A

```
Ser Thr Ser Pro Thr Gly Asp Phe Val Asp Ser Asp Gly Thr Ala Cys
            225                 230                 235
Thr Asp Gly Gly Gly Thr Met Val Leu Glu Ser His Gly Glu Val Tyr
        240                 245                 250
Gly Pro Gly Gly Gln Gly Val Tyr Asp Asp Pro Asn Leu Gly Pro Val
        255                 260                 265
Leu Tyr Tyr His Tyr Met Asn Thr Thr Ile Gly Tyr Ala Asp Ser Asp
270                 275                 280                 285
Ala Gln Phe Gly Trp Asn Thr Ile Asp Phe Ser Asp Gly Trp Thr Gly
            290                 295                 300
Cys Ile Ser Ile Leu Val Gly Asp Gly Asn Gly Ala Ala Tyr Glu Arg
            305                 310                 315
Val Tyr Lys Leu Tyr Ile Gly Leu Arg Leu
        320                 325
```

CLONING AND EXPRESSION OF DNA MOLECULES ENCODING ARABINAN-DEGRADING ENZYMES OF FUNGAL ORIGIN

The present invention relates to the field of molecular biology. In particular, the present invention relates to the cloning and expression of genes encoding enzymes of fungal origin.

BACKGROUND OF THE INVENTION

The composition of the plant cell wall is complex and variable. Polysaccharides are mainly found in the form of long chains of cellulose (the main structural component of the plant cell wall), hemicellulose (comprising various β-xylan chains) and pectic substances (consisting of galacturonans and rhamnogalacturonans; arabinans; and galactans and arabinogalactans). From the standpoint of the food industry, the pectic substances, arabinans in particular, have become one of the most important constituents of plant cell walls (Whitaker, J. R. (1984) Enzyme Microb. Technol., 6, 341).

Arabinans consist of a main chain of α-L-arabinose subunits linked α-(1→5) to one another. Side chains are linked α-(1→3) or sometimes α-(1→2) to the main α-(1→5)-L-arabinan backbone. In apple, for example, one third of the total arabinose is present in the side chains. The molecular weight of arabinan is normally about 15 kDa.

Enzymes capable of degrading arabinans are becoming increasingly important to the food industry. In juice production, for example, the demand to increase yields in order to reduce production costs has necessitated the modification of traditional processes. The utilization of enzymatic pre-treatments of the fruit pulp before pressing with specific enzymatic products drastically improves the juice yield by solubilizing the cell wall polysaccharides.

However, a persistent turbidity commonly referred to as "arabinan haze" has been a source of problems in the production of concentrated juices. The arabinan haze is more often present in concentrated juice than in non-concentrated juice. This may indicate that water activity has an influence on the solubility of arabinan. Furthermore, it has been found that this haze is soluble between 60° and 80° C.

It has also been found that while branched arabinan is soluble in concentrated chilled apple and pear juices, the linear, debranched α-(1→5)-L-arabinan is much less soluble. This debranched α-(1→5)-L-arabinan is formed from the L-arabinan by the action of an arabinan-degrading enzyme present in the commercial pectic enzyme preparations from *Aspergillus niger*, commonly used to increase juice yield after pulp treatment but before pressing.

On the other hand, debranched arabinans are considered desirable for certain other applications. WO 90/06343 discloses the debranching of sugar beet araban by the action of an α-L-arabinofuranosidase, free of endo arabinanase activity, which is isolated from a culture filtrate of *Aspergillus niger* or from a commercial pectinase mixture using ion-exchange and gel filtration chromatography procedures. The debranched araban may be used as a fat substitute in foods.

Arabinan-degrading enzymes are known to be produced by a variety of plants and microorganisms, among these, fungi such as those of the genera Aspergillus, Corticium, Rhodotorula (Kaji, A. (1984) Adv. Carbohydr. Chem. Biochem., 42, 383), Dichotomitus (Brillouet et al. (1985) Carbohydrate Research, 144, 113), Ascomycetes and Basidomycetes (Sydow, G. (1977) DDR Patent Application No. 124,812).

In particular, the filamentous fungus *Aspergillus niger* is known to produce three different arabinan-degrading enzymes: an α-L-arabinanase having a molecular weight of approximately 35 kDa and two α-L-arabinofuranosidases having molecular weights of approximately 118 and 60 kDa, respectively, (Rombouts et al. (1988) Carbohydrate Polymers, 9, 25). [N. B. van der Veen et al. ((1991) Arch. Microbial., 157, 23) reports molecular weights of 43, 83 and 67 kDa for these same three enzymes, respectively.]

The 35 kDa arabinanase (also known as ABN A) has endo activity and exclusively cleaves 1→5 linkages. The activity of this enzyme decreases as the 1,5-α-L-arabinan sequences become shorter and the concentration of arabinose dimers and trimers increased (Rombouts et al., supra). [N. B. van der Veen et al. (1991) reported a molecular weight of 43 kDa.]

The 118 kDa α-L-arabinofuranosidase (also known as arabinofuranosidase A, ABF A or EXO A) exclusively cleaves 1→5 linkages with exo-type activity as shown by the accumulation of arabinose monomers. This enzyme displays the highest activity on low molecular weight substrates (Rombouts et al., supra). [N. B. van der Veen et al. (1991) reported a molecular weight of 83 kDa.]

The 60 kDa α-L-arabinofuranosidase (also known as arabinofuranosidase B, ABF B or EXO B), also having exo-type activity, predominantly cleaves 1→3 and 1→2 α-L-arabinans, yet also demonstrates the ability to cleave 1→5 α-L-arabinans. Again, only arabinose monomers are detected after degradation of an α-L-arabinan-containing substrate (Rombouts et al., supra). [N. B. van der Veen et al. (1991) reported a molecular weight of 67 kDa.]

The *A. niger* ABF B enzyme has also demonstrated the ability to cleave the 1→6 linkage between a terminal arabinofuranosyl unit and the intermediate glucose of monoterpenyl α-L-arabinofuranosylglucosides (Gunata et al. (1989) European Patent Application No. 332.281; Gunata et al. (1990) J. Agric. Food Chem., 38, 772).

Enzymes having an activity similar to that of the *A. niger* ABF B enzyme have been identified in other fungi such as *Dichotomitus squalens* (Brillouet et al., supra), *Corticium rolfsii* and *Rhodotorula flava* (Kaji, A., supra).

A possible solution to the problem of haze formation in juices may be to use an enzyme formulation having an improved balance between the endo arabinanase (ABN A) and the ABF A and ABF B enzymes, or alternatively, enzymes having similar activities, i.e. one or more arabinofuranosidases obtained from another microorganism which is capable of cleaving 1→3 and 1→2 α-L-arabinans, as well as 1→5 α-L-arabinans. However, normal fermentation of *A. niger* fails to yield sufficient levels of the desired arabinofuranosidases. Moreover, it would be advantageous to be able to attenuate the amount of ABF A, ABF B and ABN A activities for optimal results in specific applications.

The ability of the ABF B enzyme to cleave the terminal 1→6 linkage of monoterpenyl α-L-arabinofuranosylglucosides may be used to assist in the release of aroma components from various fruit juices and thus, the enhancement of their flavors (Gunata, Z. et al. (1989 and 1990), supra). However, it would be preferable to use a purified ABF B or ABF B-like enzyme for this purpose since the presence of other enzymatic activity may degrade other important components of the juice and, in so doing, have a detrimental effect on the ultimate quality of the juice.

In nature, microbial arabinan-degrading enzymes are always produced together with other enzymes having polysaccharide-degrading activities, such as pectinases, xylanases, acetyl xylan esterases, acetyl esterases, galactanases and cellulases. As mentioned above, for some applications, these enzyme activities are not needed or are unwanted. Moreover, due to relatively low expression levels in the wild-type strains, the arabinan-degrading enzymes have proven to be somewhat difficult to isolate both from each other and from other enzymes produced by A. niger.

It is known that fermentation conditions may be varied to favor the production of an enzyme of interest. It is also known that the cloning of the gene encoding the desired enzyme and overexpressing it in its natural host, or in another compatible expression host will specifically enhance the production of the enzyme of interest. This latter method is particularly useful if the enzyme of interest is to be obtained in increased amounts, or in a form which is free of other, undesired enzymatic activity.

Clearly, it would be useful to increase arabinan-degrading activity via recombinant DNA techniques. However, until now, the genes encoding the A. niger arabinan-degrading enzymes have not been available. Accordingly, it would be of great importance to obtain genes encoding arabinan-degrading enzymes of fungal origin which may be brought to expression in its native host or, alternatively, in other microbial hosts wherein high expression levels of one or more arabinan-degrading enzymes may be achieved.

The expression of recombinant bacterial α-L-arabinofuranosidase has been previously described by Schwarz et al. ((1990) Biochem. Biophys. Res. Commun., 170, 368). The gene encoding a bacterial arabinofuranosidase was isolated from *Clostridium stercorarium* and brought to expression in an *E. coli* host.

A gene encoding an arabinosidase was cloned from the anaerobic bacterium *Bacteriodes ovatus* and brought to expression in *E. coli*, as disclosed by Whitehead & Hespell ((1990) J. Bacteriol., 172, 2408).

However, *E. coli* expression hosts are, in some instances, considered to be unsafe for the production of proteins by recombinant DNA methods due to their production of unacceptable by-products such as toxins. Furthermore, in *E. coli* expression, large amounts of heterologous protein tend to accumulate inside the cell. Subsequent purification of the desired protein from the bulk of *E. coli* intracellular proteins can sometimes be difficult.

Moreover, since bacterial genes contain no introns, one is confronted with few problems in cloning and expressing such genes in prokaryotic hosts. On the other hand, the expression of eukaryotic genes is not always so straightforward. It is well known that genes isolated from eukaryotic strains may contain introns. This inherently introduces complications in the cloning and expression of these genes, should a prokaryotic host be preferred.

Furthermore, certain differences exist between the physical characteristics of arabinan-degrading enzymes of fungal origin and those from bacteria. In general, fungal enzymes have a pH optimum in the range from ≦3.0–6.0. A few fungal species produce arabinan-degrading enzymes having pH optima as low as pH 2.0. These pH optima are generally significantly lower as compared to similar enzymes from bacterial strains which have a pH optimum in the range of pH 5.0–7.0 (Karimi and Ward (1989) J. Indust. Microbiol., 4, 173; Lee and Forsberg (1987) Can. J. Microbiol., 33, 1011). Thus, it is clear that bacterial arabinan-degrading enzymes are less suitable for use in, for example, processes requiring lower pH conditions.

SUMMARY OF THE INVENTION

The present invention provides purified and isolated DNA molecules of fungal origin, each encoding an enzyme having arabinan-degrading activity.

It is also an object of the present invention to provide DNA constructs for the enhanced microbial expression of the DNA molecules of the present invention. The DNA (or expression) constructs provided contain the DNA molecule encoding the desired arabinan-degrading enzyme with either its native 5' and 3' regulatory regions or, in an alternative embodiment, hybrid DNA constructs are provided in which the DNA molecule is operably linked to regulatory regions such as promoter, secretion leader and terminator signals which may be selected to provide for the optimal expression of the enzyme in the desired expression host and, if desired, the secretion therefrom.

It is a further object of the present invention to provide microbial expression hosts, transformed with one or more DNA constructs of the present invention, which are capable of the enhanced expression and, if desired, the secretion of arabinan-degrading enzymes of fungal origin.

It is yet a further object of the present invention to provide methods for the production of large quantities of arabinan-degrading enzymes of interest which may be advantageously used in industrial processes. Typically, industrial processes which require the activity of arabinan-degrading enzymes at a lower pH than that at which similar enzymes of bacterial origin optimally function.

BRIEF DESCRIPTION OF THE FIGURES

FIG. 2 Amino acid sequence of the N-terminus of *A. niger* ABF B protein (Formula 1) (SEQ ID NO:1) and the nucleotide sequence of the oligonucleotide mixture AB1719 (Formula 1a) (SEQ ID NO:3).

FIG. 3 Amino acid sequence of the N-terminus of the 15 kDa CNBr fragment of the *A. niger* ABF B protein (Formula 3) (SEQ ID NO:2) and the nucleotide sequence of the oligonucleotide mixture AB2306 (Formula 3a) (SEQ ID NO:4).

FIG. 5 Nucleotide sequence of the *A. niger* abfB gene (Formula 4) (SEQ ID NO:5).

FIG. 6 Amino acid sequence (Formula 5) (SEQ ID NO:6), of the *A. niger* ABF B protein, derived from the abfB gene sequence and confirmed by the abfB cDNA sequence.

▧: sequences encoding the 18 amino acid signal peptide of the *A. niger* amyloglucosidase (AG) gene (glaA).

■: sequences encoding the mature ABF B protein

Amp: the ampicillin resistance gene ori: *E. coli* origin of replication

AG: the *A. niger* amyloglucosidase (AG) promoter

Figure 10:
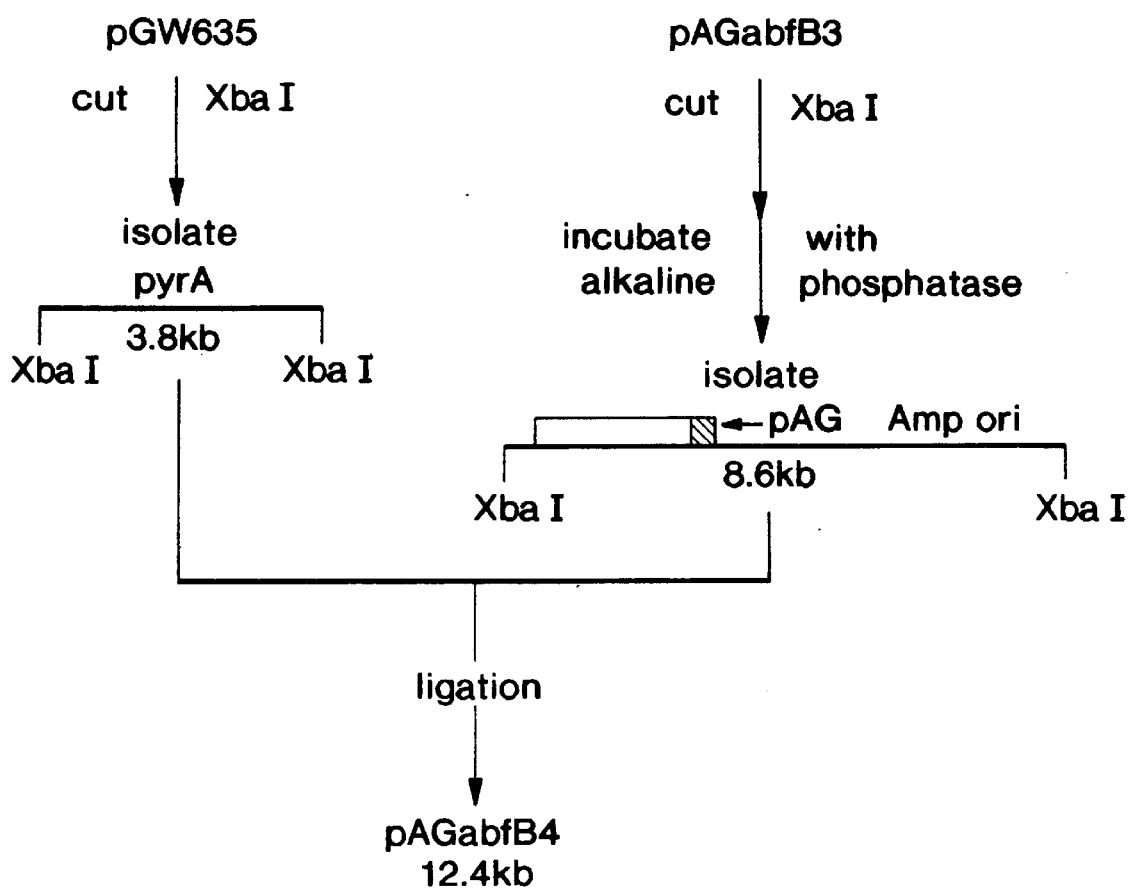

FIG. 10 The construction of the expression cassette pAGabfB4. Key to the symbols used:

pyrA: the *A. niger* gene coding for orotidine-5'-phosphate-decarboxylase

Figure 9:
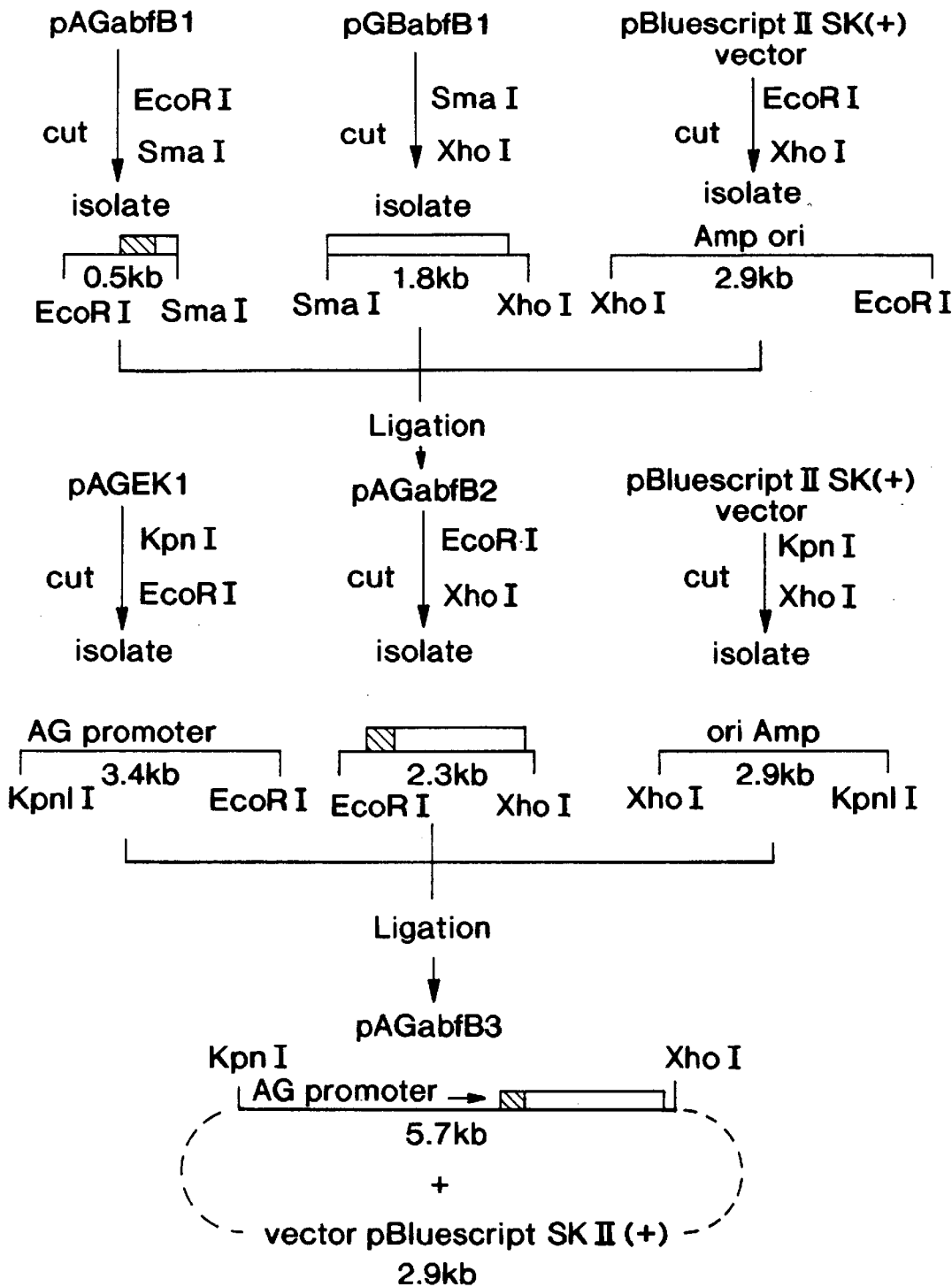
FIG. 9 A schematic representation of the construction of pAGabfB2 and pAGabfB3. Key to the symbols used.

The remaining symbols are the same as those presented in the legends of FIG. 9.

Figure 11:
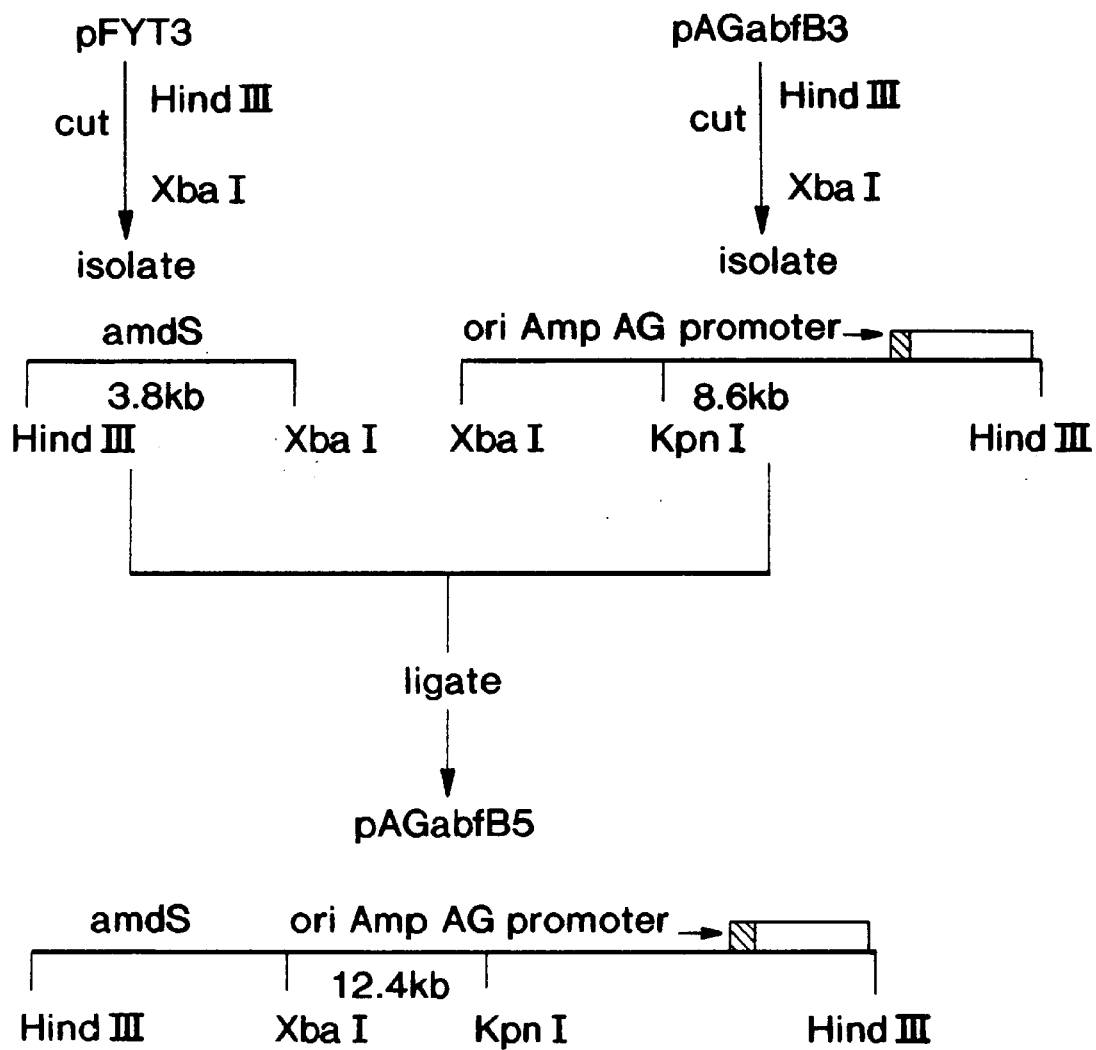

FIG. 11 The construction of the expression cassette pAGabfB5. Key to the symbols used:

amdS: the A. nidulans gene coding for an acetamidase
The remaining symbols are the same as those presented in the legends of FIG. 9.

Figure 12:
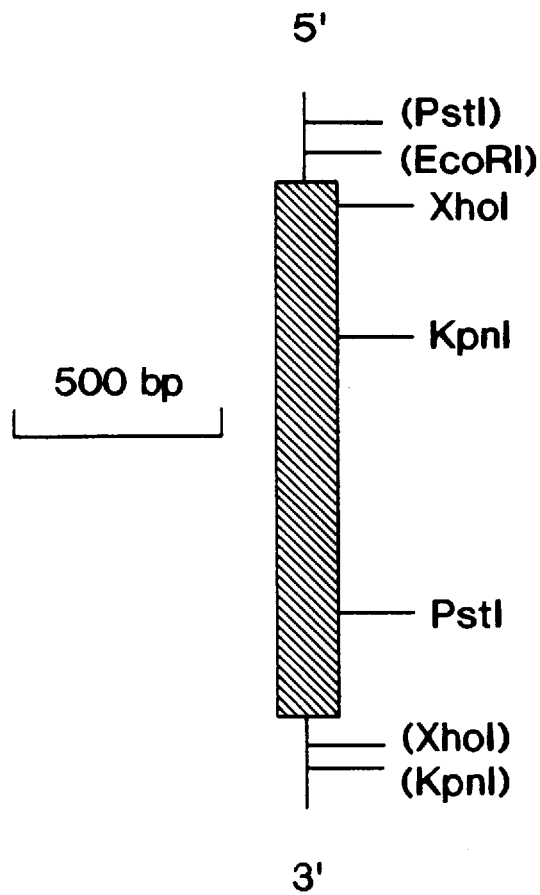

FIG. 12 Restriction map of cDNA clone pC1X1. Only the KpnI, PstI and XhoI sites are indicated. Restriction sites from the polylinker of the pBluescript SK-vector part of pC1X1 are denoted between brackets and not drawn on scale.

Figure 13:
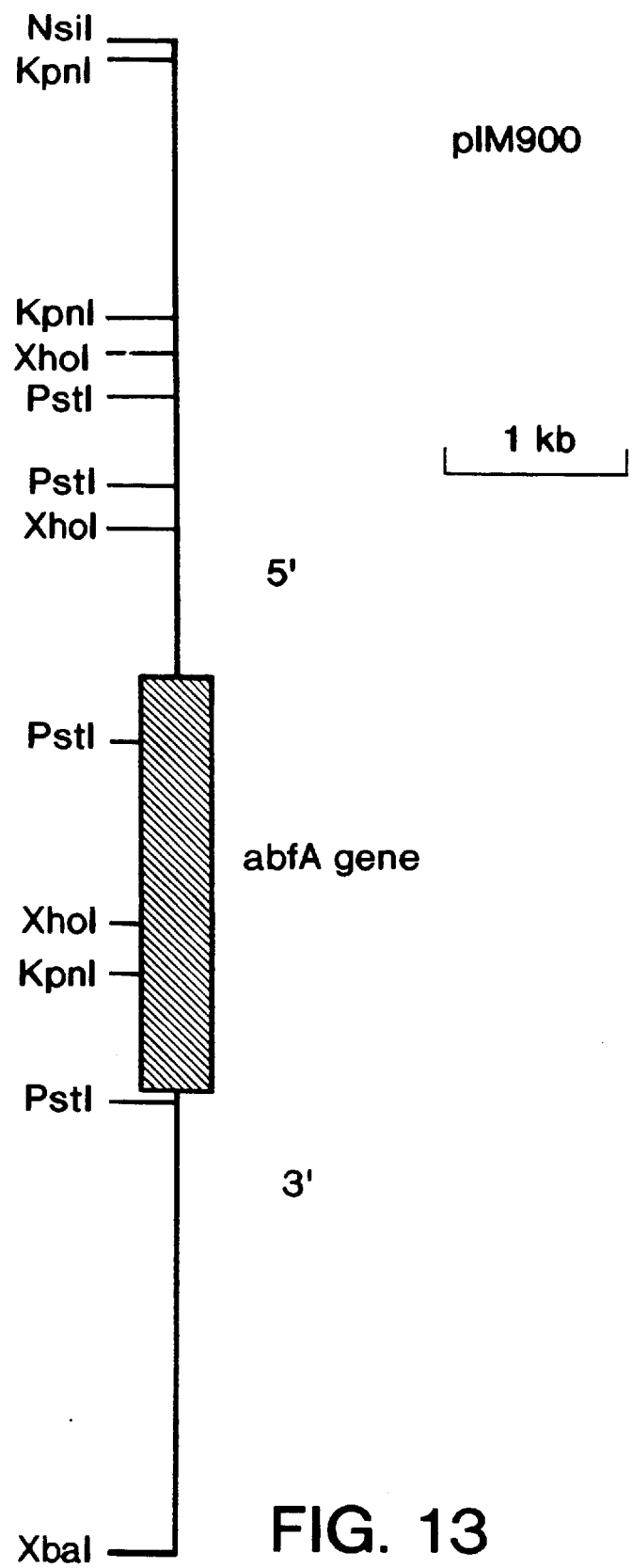

FIG. 13 Restriction map of pIM900. The bar represents the 8.5 kb XbaI/NsiI fragment cloned in the vector pGEM-7Zf(+). The hatched box represents the approximate position of the abfA gene. Only the KpnI, PstI and XhoI sites are indicated.

FIG. 14 Nucleotide sequence of the A. niger abfA gene (Formula 20) (SEQ ID NO:21).

FIG. 15 Amino acid sequence (Formula 21) (SEQ ID NO:22) of the A. niger ABF A protein derived from the abfA cDNA sequence.

FIG. 16

A: Analysis of culture filtrate of A. nidulans abfA transformants and wild type WG096 grown for 24 hours on sugar beet pulp by SDS-PAGE followed by Coomassie Brilliaint Blue R250 staining.
  lane 1: 1 µg purified α-L-arabinofuranosidase A
  lane 2: WG096
  lanes 3 to 6: randomly chosen abfA transformants B: Analysis of culture filtrate of A. niger abfA transformants and wild type N402 grown for 24 hours on sugar beet pulp by Western blot analysis.
  lane 1: 1 µg purified α-L-arabinofuranosidase A
  lane 2: N402
  lanes 3 to 6: randomly chosen abfA transformants FIG. 17 Analysis of the induction pattern of ABF B and ABN A in A. niger N572 by Western blot analysis of culture filtrates using anti ABF B and anti ABN A antibodies.
  lane 1: 24 hours growth on 1% D-glucose
  lane 2: 1 hour induction on 1% L-arabitol
  lane 3: 2 hours induction on 1% L-arabitol
  lane 4: 3 hours induction on 1% L-arabitol
  lane 5: 4 hours induction on 1% L-arabitol
  lane 6: 5 hours induction on 1% L-arabitol
  lane 7: 6 hours induction on 1% L-arabitol
  lane 8: 7 hours induction on 1% L-arabitol
  lane 9: 1 µg purified α-L-arabinofuranosidase B FIG. 18 Restriction map of pIM950. The bar represents the 3.1 HindIII fragment cloned in the vector pEMBL19. The hatched box represents the approximate position of the abnA gene.

FIG. 19 Nucleotide sequence of the A. niger abnA gene (Formula 22) (SEQ ID NO:23).

FIG. 20 Amino acid sequence (Formula 23) (SEQ ID NO:24) of the A. niger ABN A protein derived from the abnA cDNA sequence.

Figure 21:
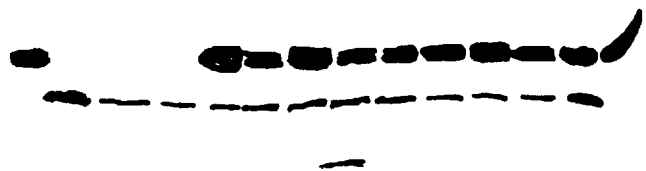

FIG. 21 Analysis of culture filtrate of A. nidulans abnA transformants and wild type WG096 grown for 24 hours on sugar beet pulp by Western blot analysis.
  lane 1: 1 µg purified endo 1,5-α-L arabinanase from A. niger
  lane 2: 1 µg purified endo 1,5-α-L arabinanase from A. nidulans
  lanes 3 and 4: A. nidulans WG096
  lane 5: Transformant #20
  lane 6: Transformant #18
  lane 7: Transformant #17
  lane 8: Transformant #16
  lane 9: Transformant #12
  lane 10: Transformant #11
  lane 11: Transformant #7
  lane 12: Transformant #6
  lane 13: Transformant #2
  lane 14: Transformant #1

Figure 22A:
Figure 22B:

FIG. 22 Western blot analysis of culture filtrates of A. niger abnA transformants and wild type N402 grown for 24 hours on sugar beet pulp by Western blot analysis.
A:
  lane 1: 1 µg purified endo 1,5-α-L arabinanase from A. niger
  lane 2: N402
  lanes 3 to 9: Transformants 1 to 7
B:
  lane 1: 1 µg purified endo 1,5-α-L arabinanase from A. niger
  lane 2: N402
  lanes 3 to 9: Transformants 8 to 14

DETAILED DESCRIPTION OF THE INVENTION

The present invention provides purified and isolated DNA molecules obtainable from fungi, and genetic variants thereof, which encode enzymes having arabinan-degrading activity. Genetic variants include DNA molecules encoding mutant arabinan-degrading proteins and degenerate DNA molecules wherein the desired activity of the enzyme expressed therefrom is retained.

The present invention also provides DNA constructs (also referred to herein as expression constructs) for the expression of one or more arabinan-degrading enzymes in a desired expression host. The DNA constructs provided may comprise the DNA molecule encoding the desired arabinan-degrading enzyme with its native 5' and 3' regulatory regions. Alternatively, hybrid DNA constructs are provided which comprise a DNA molecule encoding the arabinan-degrading enzyme operably linked to regulatory regions, such as promoter, secretion and terminator signals originating from homologous or heterologous organisms, these regulatory regions being capable of directing the enhanced expression of the structural gene in an appropriate host. Preferably, the expression construct will be integrated into the genome of the selected expression host.

The present invention further provides vectors, preferably plasmids, for the cloning and/or transformation of microbial hosts via the introduction into the microbial host of the DNA constructs for the expression of the desired arabinan-degrading enzyme.

In addition, the present invention provides microbial hosts transformed with one or more vectors, each containing at least one of the DNA constructs described above. Microbial expression hosts may be selected from bacteria, yeasts or fungi.

Within the context of the present invention, the term "enhanced expression" is defined as the expression of the DNA construct whereby the arabinan-degrading enzyme of interest is produced at levels higher than that which are ordinarily encountered in the homologous wild-type organism. In the same context, enhanced expression also intends expression in a heterologous organism which does not normally produce such arabinan-degrading enzyme except for the introduction of the DNA molecule encoding the arabinan-degrading enzyme of interest, together with appropriate regulatory regions, into the heterologous expression host. Progeny of these expression hosts are, of course, also to be understood to be embraced by the present invention.

Within the context of the present invention, the term "homologous" is understood to intend all that which is native to the DNA molecule encoding the arabinan-degrading enzyme of interest, including its regulatory regions. A homologous host is defined as the species from which such DNA molecule may be isolated.

The term "heterologous" is thus defined as all that which is not native to the DNA molecule encoding the arabinan-degrading enzyme of interest itself, including regulatory regions. A "heterologous" host is defined as any microbial species other than that from which the arabinan-degrading enzyme-encoding gene has been isolated.

Within the scope of the present invention, the term "arabinan-degrading enzyme of interest" is understood to include arabinan-degrading enzymes of fungal origin.

Arabinan-degrading activity, as defined in the context of the present invention, is the ability of an enzyme to release arabinose residues, either monomers or oligomers, from arabinan backbones or from arabinan-containing sidechains of other hemicellulose backbone structures such as arabinoxylans or arabinogalactans, or even the release of arabinose monomers via the cleavage of the 1→6 linkage between the terminal arabinofuranosyl unit and the intermediate glucosyl unit of monoterpenyl α-L-arabinofuranosyl glucosides.

Examples of preferred "arabinan-degrading activity" may be selected from:

a) the ability to cleave (1→2)-α-L-arabinosidic linkages;
b) the ability to cleave (1→3)-α-L-arabinosidic linkages;
c) the ability to cleave (1→5)-α-L-arabinosidic linkages;
d) the ability to cleave the 1→6 linkage between the terminal arabinofuranosyl unit and the intermediate glucosyl unit of monoterpenyl α-L-arabinofuranosyl glucosides.

Most preferred arabinan-degrading enzymes are α-L-arabinofuranosidases and α-L-arabinanases which have 1) exo-type arabinan-degrading activity on (1→5)-α-L-arabinosidic linkages; or 2) exo-type arabinan-degrading activity on (1→3)-α-L-arabinosidic linkages and (1→2)-α-L-arabinosidic linkages; 3) endo-type arabinan-degrading activity on (1→5)-α-L-arabinosidic linkages; or 4) the ability to cleave the 1→6 linkage between the terminal arabinofuranosyl unit and the intermediate glucosyl unit of monoterpenyl α-L-arabinofuranosyl glucosides.

Preferred DNA molecules encoding arabinan-degrading enzyme of the present invention are those which are obtainable from filamentous fungi of the genera Aspergillus (especially *A. niger, A. niger* var. *tubigensis* (see also Kusters-van Someren (1991) Curr. Genet., *19, 21*), *A. niger* var. *awamori, A. nidulans* (with the exception of the abfA gene) and *A. aculeatis*), Dichotomitus (especially *D. squalens*), Corticium (especially *C. rolfsii*), Penicillium (especially *P. chrysogenum*) and Rhodotorula (especially *R. flava*). Especially preferred are the α-L-arabinanase (ABN A), and the α-L-arabinofuranosidases (ABF A and ABF B) which are obtainable from *Aspergillus niger, Aspergillus niger* var. *tubigensis* or *Aspergillus niger* var. *awamori*.

The present invention also includes DNA sequences which hybridize under low stringency conditions to the DNA sequences obtainable from the fungi described above, but which may differ in codon sequence due to the degeneracy of the genetic code or cross-species variation.

Arabinofuranosidases having the desired activity may be identified by various methods not critical to the present invention. For example, assays for the presence of paranitrophenol or arabinose monomers are indicative of the ability of the enzyme to cleave 1→3 or 1→2-α-L-arabinosidic linkages using para-nitrophenyl-α-L-arabinoside or other arabinan-containing substrates, respectively, using methods such as those described by Rombouts et al. ((1988) supra) or van der Veen et al. ((1991) supra). The ability of an enzyme to cleave 1→5-α-L-arabinosidic linkages may be determined using an apple juice ultrafiltration retentate (UFR) arabinan substrate and assaying for the presence of small arabinoside oligomers as described by Rombouts et al., supra. Alternatively, endo 1,5-α-L-arabinanase activity of a culture filtrate may be measured using a test kit such as Arabina-Zyme™ tablets as produced by Megazyme Pty. Ltd. (North Rocks, New South Wales, Australia).

Figure 1:
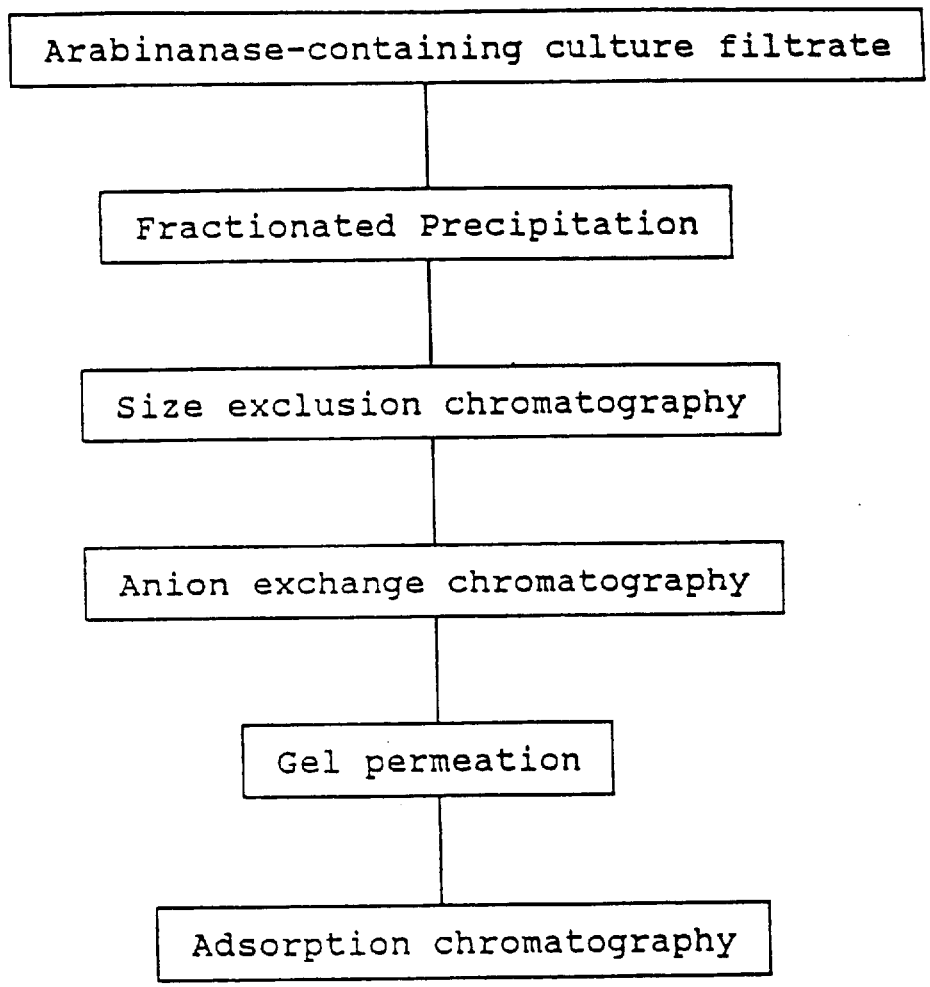
FIG. 1 Schematic diagram of the purification procedure for obtaining the α-L-arabinofuranosidase (ABF B) enzyme from *A. niger*.

Once an arabinan-degrading enzyme of interest has been identified, the DNA molecule encoding such arabinan-degrading enzyme may be obtained from the filamentous fungus which naturally produces it by culturing the fungus in a suitable medium, isolating the desired arabinan-degrading enzyme using known methods such as those outlined in FIG. 1 (ABF B enzyme) or those as described by Rombouts et al. ((1988) supra) or van der Veen et al. ((1991) supra) and determining at least a portion of the amino acid sequence of the purified protein.

DNA probes may thereafter be obtained by designing oligonucleotides based on the deduced partial amino acid sequence. Amino acid sequences may be determined from the N-terminus of the complete protein and/or from the N-termini of internal peptide fragments obtained via proteolytic or chemical digestion of the complete protein. Once obtained, the DNA probe(s) are then used to screen a genomic or cDNA library.

A genomic library may be prepared by partially digesting the fungal chromosomal DNA with a restriction enzyme which recognizes a DNA sequence of four successive nucleotides, e.g. Sau3A, and cloning the resulting fragments in a suitable plasmid or lambda phage vector, e.g. lambda GEM-11.

Alternatively, a cDNA library may be prepared by cloning cDNA, synthesized from mRNA isolated from fungal cells induced for the synthesis of arabinan-degrading enzyme, into an appropriate phage vector, e.g. lambda gt10, such as described by Harmsen et al. (1990) Curr. Genet., 18, 161.

Subsequently, after plating of a sufficient amount of colonies or plaques, the genomic or cDNA library may be screened with a suitable DNA probe.

If this method is unsuccessful, the genomic or cDNA library may be differentially screened with cDNA probes obtained from mRNA from non-induced and induced cells. Induced mRNA is prepared from cells grown on media containing arabinan as a carbon source, while non-induced mRNA must be isolated from cells grown on a carbon source other than arabinan, e.g. glucose. Among the clones which only hybridize with the induced cDNA probe, a clone containing the gene encoding the desired arabinan-degrading enzyme may be recovered. Alternatively, a gene encoding an arabinan-degrading enzyme of interest may be identified by cross-hybridization with a gene from a related arabinan-degrading enzyme.

In the case of the ABF B enzyme, oligonucleotide probes are obtained from the N-terminal amino acid sequence (see FIG. 2, Formula 1) (SEQ ID NO:1) of an arabinan-degrading enzyme having an apparent molecular weight of 60 kDa (in glycosylated form) purified from an *Aspergillus niger* culture filtrate and/or from the amino acid sequence of an internal peptide fragment (see FIG. 3, Formula 3) (SEQ ID NO:2) obtained by digestion of the enzyme with CNBr. The oligonucleotide mixtures AB1719 (FIG. 2, Formula 1a) (SEQ ID NO:3) and AB2306 (FIG. 3, Formula 3a) (SEQ ID NO:4) are complementary to the corresponding deduced arabinofuranosidase mRNA. Four positive phage clones were obtained from the screening of a lambda GEM-11 library, prepared from partially Sau3A digested DNA isolated from *Aspergillus niger*, with the N-terminal oligo mixture AB 1719.

DNA isolated from the four phage clones hybridized with the N-terminal oligonucleotide mixture AB1719 (see FIG. 2, Formula 1a) (SEQ ID NO:3). A 2.8 kb SacI fragment was obtained (see FIG. 4) and has been sequenced. The nucleotide sequence and encoded amino acid sequence are depicted in FIGS. 5 and 6 (SEQ ID NO:5 and SEQ ID NO:6), (Formulas 4 and 5, respectively). The SacI fragment, in plasmid pGBabfB1, was deposited in *E. coli* strain DH5α at the Centraal Bureau voor Schimmelcultures (Baarn, the Netherlands on Mar. 11, 1991, under accession number CBS 156.91).

The abfB gene encodes a protein 499 amino acids in length having a deduced molecular weight of 52523 Da (FIG. 6, Formula 5) (SEQ ID NO:6), as derived from the abfB gene sequence (FIG. 5) (SEQ ID NO:5) and confirmed by the abfB cDNA sequence. The N-terminal amino acid sequence, as determined in Example 12.2 (Formula 14) is preceded by a 18 amino acid-long hydrophobic sequence. The amino acid sequences determined from the CNBr peptides (Formulas 15, 16 and 17) are found in the sequence from amino acid position 203 until position 219, 267 until 286 and 294 until 312, respectively. The mature ABF B protein is 481 amino acids in length, and the unglycosylated protein has a deduced molecular weight of 50663 Da and a theoretical IEP of 3.8.

In the case of the ABF A enzyme, a cDNA library was made after the induction of mRNA in a strain of *Aspergillus niger*, using L-arabitol as inducer. Poly A$^+$ RNA was isolated and used to synthesize cDNA which was in turn ligated into a bacteriophage lambda vector. The cDNA expression library was screened and phages expressing a fusion protein containing a part of the α-L-arabinofuranosidase A (ABF A) protein were identified by probing the filters with anti α-L-arabinofuranosidase A antiserum and subsequent detection using an alkaline phosphatase conjugate. The clone containing the largest insert (1.3 kb), designated pC1X1, was subjected to a limited restriction analysis (FIG. 12).

An *Aspergillus niger* genomic library was also constructed and screened for the abfA gene. Plaque hybridization, using nitrocellulose replicas, was performed and 18 hybridizing plaques, appearing in duplicate on the replica filters, were identified: lambda$_{abf}$A1 to lambda$_{abf}$A18. The DNA isolated from phages lambda$_{abf}$A1, lambda$_{abf}$A5, lambda$_{abf}$A6 and lambda$_{abf}$A12 was analyzed by restriction analysis. A partial restriction map of the genomic region of the abfA gene was obtained. An 8.5 kb NsiI/XbaI fragment from phage lambda$_{abf}$A5 was ligated in the vector pGEM-7Zf(+), resulting in the plasmid pIM900. The plasmid pIM900 was further analyzed using restriction enzymes resulting in a restriction map as shown in FIG. 13. The plasmid pIM900 containing the abfA gene was recloned into *E. coli* JM109 and was deposited at the Centraal Bureau voor Schimmelcultures (Baarn, the Netherlands on Mar. 17, 1992, under accession number CBS 187.92). The sequence of the abfA gene is provided in FIG. 14 (Formula 20) (SEQ ID NO:21).

The abfA gene encodes a protein 628 amino acids in length (FIG. 15, Formula 21) (SEQ ID NO:22) as derived from the abfA cDNA sequence. The N-terminal amino acid sequence, as determined in Example 12.1 (Formula 12) is preceded by a 25 amino acids long hydrophobic sequence. The amino acid sequence determined from the CNBr peptide (Formula 13) is found in the sequence from position 38 until position 52. The mature ABF A protein is 603 amino acids in length, and the unglycosylated protein has a deduced molecular weight of 65378 Da and a theoretical IEP of 3.7.

In the case of the ABN A enzyme, a cDNA library was made after the induction of mRNA in a strain of *Aspergillus niger*, using L-arabitol as inducer. The strain was cultured and mycelium was harvested at regular time intervals. RNA was isolated and used to synthesize cDNA and construct an expression library. The library was amplified and screened using antibodies raised against ABN A. A single positive clone was isolated. The length of the cDNA insert was determined by digestion with EcoRI/XhoI and subsequent agarose electrophoresis. The cDNA fragment was approximately 700 bp in length.

An *Aspergillus niger* genomic library was also constructed and screened for the abnA gene. Plaque hybridization was performed as for the ABN A enzyme and 6 hybridizing plaques were isolated. DNA was isolated from each of the phages and was used for restriction analysis which resulted in a partial restriction map. Using this restriction map, a 3.1 kb HindIII was selected for subcloning of the abnA gene into the vector pEMBL19, which resulted in the plasmid pIM950. This plasmid was further analyzed using restriction enzymes, providing the restriction map shown in FIG. 18. The plasmid pIM950 containing the abnA gene was recloned into *E. coli* JM109 and was deposited at the Centraal Bureau voor Schimmelcultures (Baarn, the Netherlands on Mar. 17, 1992, under accession number CBS 188.92). The sequence of the abnA gene is provided in FIG. 19 (Formula 22) (SEQ ID NO:23).

The abnA gene encodes a protein 346 amino acids in length, having a molecular weight of 37184 Da (FIG. 20, Formula 23) (SEQ ID NO:24) as derived from the abnA cDNA sequence. The N-terminal sequence, as determined in Example 12.3 (Formula 18) is preceded by a 19 amino acids long hydrophobic sequence. The amino acid sequence as determined from a CNBr peptide (Example 12.3, Formula 19) is found from position 106 until position 125 of the amino acid sequence. The mature protein is 327 amino acids in length and the unglycosylated protein has deduced a molecular weight of 35204 Da and a theoretical IEP of 3.6.

The availability of a DNA molecule encoding an arabinan-degrading enzyme of interest enables the construction of mutant arabinan-degrading enzymes by site-directed mutagenesis. If the tertiary structure of the arabinan-degrading enzyme is known, and its catalytic and substrate binding domains are localized, amino acids may be selected for mutagenesis (for example with the aid of computer modelling) which most likely affect catalytic and/or substrate binding functions. If the tertiary structure of the protein is not available, random mutants may be either generated along with the entire coding sequence, or the tertiary structure of the protein may be predicted by comparison with similar known arabinan-degrading enzymes isolated from another microorganism.

To facilitate the insertion of the DNA fragment containing the same DNA molecule encoding the arabinan-degrading enzyme into expression constructs comprising one or more heterologous regulatory regions, the polymerase chain reaction (PCR) (*PCR Technology: Principles and Applications for DNA Amplification,* (1989) H. A. Ehrlich, ed., Stockton Press, New York) may be used for introduction of appropriate restriction enzyme sites in the 5' and 3' ends of the coding sequence. The choice of restriction sites depends on the nucleotide sequence of the expression vector, i.e. the presence of other restriction sites within the DNA molecule.

To obtain the enhanced expression of the DNA construct for the production of the arabinan-degrading enzyme of interest in the original (homologous) production species, or alternatively in a heterologous fungal strain, the DNA molecule encoding the enzyme of interest, including its native regulatory regions, may be introduced into the selected expression host to increase the copy number of the construct and, consequently, protein expression.

If a heterologous expression host is preferred, and a yeast or a bacterial strain is selected, an uninterrupted (intronless) DNA molecule is used for the construction of a heterologous expression construct in order to avoid the possibility that splice signals residing on the genomic fragment are not recognized by the heterologous host. This uninterrupted DNA molecule may be obtained from a cDNA library constructed from mRNA isolated from cells, induced for the synthesis of arabinan-degrading enzymes. This library may be screened with an oligonucleotide or cDNA probe obtained as described before. Alternatively, an uninterrupted DNA molecule may be obtained by applying a polymerase chain reaction using appropriate 5' and 3' oligonucleotides on the first strand cDNA synthesized from the RNA of arabinan-induced cells.

Enhanced expression of the DNA molecule encoding the arabinan-degrading enzyme of interest may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the arabinan-degrading enzyme of interest.

Aside from the promoter native to the gene encoding the arabinan-degrading enzyme of interest, other promoters may be used to direct its expression. The promoter may be selected for its efficiency in directing the expression of the arabinan-degrading enzyme of interest in the desired expression host.

In another embodiment, a constitutive promoter may be selected to direct the expression of the desired arabinan-degrading enzyme. Such an expression construct may provide additional advantages since it circumvents the need to culture the expression hosts on a medium containing arabinans as an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (adhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase promoters.

Examples of strong bacterial promoters are the α-amylase and Spo2 promoters as well as promoters from extracellular protease genes.

Hybrid promoters may also advantageously be used to improve inducible regulation of the expression construct.

Often, it is desirable for the arabinan-degrading enzyme of interest to be secreted from the expression host into the culture medium from where the arabinan-degrading enzyme may be more easily recovered.

According to the present invention, the arabinan-degrading enzyme of interest's native secretion leader sequence may be used to effect the secretion of the expressed arabinan-degrading enzyme.

However, an increase in the expression of the arabinan-degrading enzyme sometimes results in the production of the protein in levels beyond that which the expression host is capable of processing and secreting, creating a bottleneck such that the protein product accumulates within the cell. Accordingly, the present invention also provides heterologous leader sequences to provide for the most efficient secretion of the arabinan-degrading enzyme from the chosen expression host.

According to the present invention, the secretion leader may be selected on the basis of the desired expression host. A heterologous secretion leader may be chosen which is homologous to the other regulatory regions of the expression construct. For example, the leader of the highly secreted amyloglucosidase (AG) protein may be used in combination with the amyloglucosidase (AG) promoter itself, as well as in combination with other promoters. Hybrid signal sequences may also advantageously be used within the context of the present invention.

Examples of preferred heterologous secretion leader sequences are those originating from the fungal amyloglucosidase (AG) gene (glaA—both 18 and 24 amino acid versions e.g. from Aspergillus), the α-factor gene (yeasts e.g. Saccharomyces and Kluyveromyces) or the α-amylase gene (Bacillus).

In general, terminators are not considered to be critical elements for the enhanced expression of genes. If desired, a terminator may be selected from the same genes as the promoters, or alternatively, the homologous terminator may be employed.

In addition to the genomic fragment mentioned above, the transforming DNA may contain a selection marker to discriminate cells which have incorporated the desired gene from the bulk of untransformed cells. This selection marker, provided with the appropriate 5' and 3' regulatory sequences, may reside on the same DNA molecule containing the desired gene or be present on a separate molecule; In the latter case, a co-transformation must be performed. The ratio of the expression vector/selection vector must be adjusted in such a manner that a high percentage of the selected transformants also have incorporated the vector containing the expression construct of the arabinan-degrading enzyme of interest.

The most suitable selection systems for industrial microorganisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pyrA), phleomycin (Durand et al. (1991) Curr. Genet., 19, 149) and benomyl resistance (benA). Exemplary of non-fungal selection markers are the bacterial G418 resistance gene (this may also be used in yeast, but not in fungi), the ampicillin resistance gene (*E. coli*), the neomycin resistance gene (Bacillus) and the *E. coli* uidA gene, coding for β-glucuronidase (GUS).

Once the desired expression construct has been assembled, it is transformed into a suitable cloning host such as *E. coli* to propagate the construct. Afterwards, the expression construct is introduced into a suitable expression host wherein the expression construct is preferably integrated into the genome. Certain hosts such as Bacillus species may be used as both cloning and expression hosts, thus avoiding an extra transformation step.

According to the present invention, a variety of organisms may be used as hosts for the production of the arabinan-degrading enzyme of interest. If more than one arabinan-degrading enzyme of interest is to be produced, multiple vectors, each containing an expression construct for an arabinan-degrading enzyme of interest (e.g. ABF A, ABF B and/or ABN A) may be introduced into the same expression host. Alternatively, each desired arabinan-degrading enzyme may be produced independently in separate expression hosts.

In one embodiment of the present invention, a homologous expression host may be used. This involves the introduction of the expression construct back into the strain from which the arabinan-degrading enzyme encoding DNA molecule was isolated either in increased gene copy numbers, or under the control of heterologous regulatory regions as described above, or both.

In another embodiment, one or more arabinan-degrading enzymes of interest may be produced by introducing and expressing one or more DNA molecule(s) encoding the arabinan-degrading enzyme(s) of interest, each under the control of appropriate regulatory regions, into heterologous hosts such as bacteria, yeasts or fungi. For that purpose, a DNA molecule encoding an arabinan-degrading enzyme of interest is preferably expressed under the control of promoter and terminator sequences originating from the heterologous host. In addition, it may be necessary to replace the native secretion leader sequence of the gene of the arabinan-degrading enzyme of interest with a leader sequence homologous to the expression host in order to achieve the most efficient expression and secretion of the product.

Factors such as the size (molecular weight), the need for proper glycosylation or the desirability of the extracellular secretion of an arabinan-degrading enzyme of interest play an important role in the selection of the expression host.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium. Other bacteria suitable as hosts are those from the genera Streptomyces and Pseudomonas.

Depending on the nature of the DNA molecule encoding the arabinan-degrading enzyme of interest, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen wherein the arabinan-degrading enzyme of interest is produced in a form which is substantially free from other polysaccharide-degrading enzymes. This may be achieved by choosing a host which does not normally produce such enzymes such as *Kluyveromyces lactis*.

Examples of preferred expression hosts within the scope of the present invention are fungi such as Aspergillus species (described in European Patent Applications 184.438 and 284.603) and Trichoderma species; bacteria such as Bacillus species (described in European Patent Applications 134.048 and 253.455), Streptomyces species and Pseudomonas species; and yeasts such as Kluyveromyces species (described in European Patent Applications 96.430 and 301.670) and Saccharomyces species.

Particularly preferred expression hosts may be selected from *Aspergillus niger, Aspergillus niger* var. *tubigensis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

According to the present invention, the production of arabinan-degrading enzyme(s) of interest is effected by the culturing of microbial expression hosts which have been transformed with one or more DNA constructs of the present invention, in a conventional nutrient fermentation medium.

The fermentation medium consists of an ordinary culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). optionally, an inducer (e.g. sugar beet arabinan) may be included.

The selection of the appropriate medium may be based on the choice of expression hosts and/or based on the regulatory requirements of the expression construct. Such media are well-known to those skilled in the art. The medium may, if desired, contain additional components favoring the transformed expression hosts over other potentially contaminating microorganisms.

The fermentation is performed over a period of 0.5–20 days in a batch or fed-batch process at a temperature in the range of between 0° and 45° C. and a pH between 2 and 10. Preferred fermentation conditions are a temperature in the range of between 20° and 37° C. and a pH between 3 and 9. The appropriate conditions are selected based on the choice of the expression host.

After fermentation, the cells are removed from the fermentation broth by means of centrifugation or filtration. After removal of the cells, The arabinan-degrading enzyme of interest may then be recovered and, if desired, purified and isolated by conventional means.

The product is stably formulated either in liquid or dry form. For certain applications, immobilization of the enzyme on a solid matrix may be preferred.

Arabinan-degrading enzymes of interest, produced by means of the present invention, may be applied either singly, or as a mixture of arabinan-degrading enzyme activities (i.e. combinations of ABF A and/or ABF B and/or ABN A activities), and optionally together with other selected enzymes in a variety of processes requiring the action of arabinan-degrading enzymes. Moreover, the fungal arabinan-degrading enzymes of the present invention, which generally have lower pH optima than arabinan-degrading enzymes of bacterial origin, are particularly well suited for use in industrial processes which are performed at low pH.

It has been found that, owing to the fact that the ABF A enzyme acts only on low oligomeric arabinosides, the ABF B enzyme preferably hydrolyzes the side chain L-arabinose residues (with some endo activity) and the ABN A acts optimally on linear arabinan, mixtures of the ABF A and/or ABF B enzyme act synergistically when combined with endo arabinanase (ABN A) activity. The present invention allows the skilled artisan to produce mixtures of the desired arabinan-degrading enzyme activities having optimal proportions of the desired activities for specific industrial applications.

In accordance with the present invention, it has been found that the arabinan-degrading enzymes produced via the present invention, may be used in the production of concentrated juices, especially fruit (e.g. apple, pear and the like) or vegetable juices to eliminate "arabinan haze".

The incorporation of an amount of ABF B, for example, to an enzyme preparation (such as that obtained from an Aspergillus species) which in turn is added to the pulp prior to pressing provides an increased yield of the resultant juice without the presence of the undesirable arabinan haze in either concentrated or non-concentrated forms of the juice. A mixture of all three arabinan-degrading enzymes produced according to the present invention, may be supplemented in the processing of concentrated juices from fruits having higher amounts arabinans (e.g. pear juice). Additional enzymatic activity such as pectinase activity may also be added for optimal results as may be determined by one skilled in the art.

Moreover, the incorporation of arabinan-degrading enzymes produced according to the present invention in fruit and vegetable juices improve the filterability of the juices such as grape juice. In order to breakdown the arabinogalactans which are known to cause viscosity, the juice is first treated with an enzyme mixture having high amounts of arabinanases and arabinofuranosidases produced according to the present invention, followed by treatment with β-1-3- and β-1-6- galactanases.

Alternatively, α-L-arabinofuranosidases, particularly the ABF B enzyme, may be used to assist in the liberation of aroma compounds from substrates such as juices or wines, as described by Gunata et al. ((1989) and (1990), supra). This is achieved in a two step process wherein the first step comprises the use of an α-L-arabinofuranosidase, preferably having ABF β-like activity, to catalyze the release of arabinose residues from monoterpenyl α-L-arabinofuranosyl glucosides contained in the fruit or vegetable juice via the cleavage of the (1→6) linkage between a terminal arabinofuranosyl unit and the intermediate glucose of a monoterpenyl α-L-arabinofuranosylglucoside. The α-L-arabinofuranosidase preferably being in purified form to avoid the undesirable degradation of other components of the juice which may be detrimental to the ultimate quality of the juice. The resulting desarabinosylated monoterpenyl glucoside is then treated with a β-glucosidase to yield the free terpenol. If desired, both reaction steps may be performed in the same reaction vessel without the need to isolate the intermediate product (Gunata et al. (1989), supra).

The liberation of these aroma compounds improves the flavor of the juice or wine. Moreover, in the case of wine, the control of the liberation of aroma compounds provides wines with a more consistent flavor, thus reducing or eliminating the undesirable effect of "poor vintage years".

Arabinan-degrading enzymes may also be added to animal feeds which are rich in arabinans. When added to feeds (including silage) for monogastric animals (e.g. poultry or swine) which contain cereals such as barley, wheat, maize, rye or oats or cereal by-products such as wheat bran or maize bran, the enzyme significantly improves the break-down of plant cell walls which leads to better utilization of the plant nutrients by the animal. As a consequence, growth rate and/or feed conversion are improved. Moreover, arabinan-degrading enzymes may be used to the reduce the viscosity of feeds containing arabinans.

An arabinan-degrading enzyme may be added beforehand to the feed or silage if pre-soaking or wet diets are preferred. More advantageously, the arabinan-degrading enzymes produced via the present invention continue to hydrolyze arabinans in the feed in vivo. Fungal arabinan-degrading enzymes, which generally have lower pH optima, are capable of releasing important nutrients in such acidic environments as the stomach of the animal ingesting such arabinan-degrading enzyme-supplemented feed.

Another application for the arabinan-degrading enzymes produced according to the present invention is in the pulp and paper industry. The application of xylanases is often reported to be beneficial in the removal of lignins and terpenoids from the cellulose and hemicellulose residues of a hemicellulose backbone, an essential step in the processing of wood, wood pulp or wood derivative product for the production of paper. The addition of arabinan-degrading enzymes, produced according to the present invention, to the xylanase treatment step assists in the degradation of an arabinan-containing hemicellulose backbone and thus facilitates an improved, more efficient removal of both lignins and terpenoids. The application of arabinan-degrading enzymes is particularly advantageous in the processing of soft woods in which the hemicellulose backbone contains arabinoglucoronic xylans.

In addition, the arabinan-degrading enzymes produced via the present invention may be used in other processes such as to increase yield in the enzymatic hydrolysis of sugar beet pulp, the resulting hydrolyzed fraction being capable of use in microorganism culture medium; and the hydrolysis of sycamore or gum arabic or agricultural residues such wheatstraw.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Celsius and pressure is at or near atmospheric.

EXAMPLE 1

Enzyme Assays

Protein content, used for the determination of specific enzymatic activity, was measured according to the method of Lowry et al. ((1951) J. Biol. Chem 193, 265), except where otherwise denoted.

Arabinofuranosidase activity may be determined by the addition of 0.250 ml enzyme solution to 8 mM p-nitrophenyl α-L-arabinofuranoside (PNA—in 0.1M sodium acetate buffer; pH 4.4). After incubation for 10 min at 40° C., the reaction was stopped by the addition of 2 ml of 0.5M glycine-sodium buffer, pH 9.0. The concentration of p-nitrophenol (pNP) was determined by reading the absorbance at 400 nm. 1 nkat of activity corresponds to the liberation of 1 nmol of pNP per second under the test conditions. Alternatively, arabinofuranosidase activity may be expressed in Units per milliliter (U/ml) wherein a unit of arabinofuranosidase activity is defined as the amount of enzyme which releases 1 μmol pNP per minute from PNA (see van der Veen et al. (1991) supra).

β-D-glucopyranosidase and α-L-rhamnopyranosidase activities were measured under the same conditions, according to their action on p-nitrophenyl β-D-glucopyranoside and p-nitrophenyl α-L-rhamnopyranoside substrates, respectively.

Endo 1,5-α-L-arabinanase activity of a culture filtrate was measured and calculated using the ArabinaZyme™ test kit as produced by Megazyme Pty. Ltd. (North Rocks, New South Wales, Australia), according to the manufacturer's instructions. One unit of activity is defined as the amount of enzyme required to release 1 μmol of arabinose reducing sugar equivalents from carboxymethyl linear (1→5)-α-L-arabinan per minute under the assay conditions.

EXAMPLE 2

Purification of *Aspergillus niger* α-L-arabinofuranosidase B (ABF B)

A schematic diagram of the procedure which was applied for the purification of the α-L-arabinofuranosidase (ABF B) enzyme from a culture filtrate obtained from the *A. niger* HEM strain is shown in FIG. 1. Five steps were used for purification: 1) fractionated precipitation with ammonium sulphate; 2) size exclusion; 3) ion exchange chromatography; 4) gel permeation; and 5) adsorption chromatography.

Eluted fractions were analyzed for arabinan-degrading, rhamnosidase, glucopyranosidase activities via the calorimetric method as described in Example 1. Protein content was measured with a Bradford microtest on a titration microplate (Margaret et al. (1985) Anal. Biochem. 147, 144). Chromatography experiments were carried out at 5° C.

EXAMPLE 2.1

Fractionated Precipitation with $(NH_4)_2SO_4$

The sample of a culture filtrate obtained from *A. niger* strain HEM containing the ABF B enzyme, inter alia, was adjusted to pH 5.5 (the isoelectric point of α-L-arabinofuranosidase), with dilute acetic acid and recovered by fractionated precipitation with $(NH_4)_2SO_4$ at concentrations of 50, 60, 70, 80 and 90% of saturation at a temperature of 5° C. The precipitate was solubilized in sodium acetate buffer (pH 4.5; 0.05M) and diafiltered in the same buffer in order to remove salts. Characteristics of the different fractions are summarized in Table 1.

TABLE 1

| Enzymatic activities of the precipitates | | | | | |
|---|---|---|---|---|---|
| Enzymatic Activity | % $(NH_4)_2SO_4$ | | | | |
| (nkat/ml) | 50 | 60 | 70 | 80 | 90 |
| α-L-arabinofuranosidase | 1160 | 1100 | 260 | 43 | 12 |
| β-D-glucopyranosidase | 1300 | 1700 | 230 | 37 | 12 |
| α-L-rhamnopyranosidase | 131 | 140 | 63 | 62 | 2.7 |

EXAMPLE 2.2

Size Exclusion on BIO-GEL P10

A BIO-GEL P 10 column (BIO-RAD; Richmond, Va., U.S.A.) was pre-equilibrated with sodium acetate buffer (pH 4.5; 0.05M) at a flow rate of 60 ml/hour. A sample of 100 ml of the 50% $NH_4)_2SO_4$ precipitate was applied to the column. Proteins were eluted under the same conditions. Fractions of 20 ml were collected and assayed for their α-L-arabinofuranosidase activity. Fractions 14 to 22 were pooled and concentrated by ultrafiltration (cut-off=10,000×D) at the start volume.

EXAMPLE 2.3

Anion Exchange Chromatography on DEAE ART LS

A DEAE ART LS column (5,2×36 cm; IBF Biotechnics, France) was pre-equilibrated in 0.05M; pH 4.5 sodium acetate buffer at a flow rate of 100 ml/hour. A 100 ml volume of the pool of α-L-arabinofuranosidase obtained from Example 2.2 (above) was applied to the column. The protein was eluted using a gradient of sodium chloride from 0 to 0.5M in the start buffer. Fractions of 15 ml were collected and assayed for enzyme activities.

An α-L-rhamnosidase peak appeared near the void volume of the column, showing that this enzyme was in the neutral or cationic form at this pH (pool CY183 III-1). β-D-glucopyranosidase and α-L-arabinofuranosidase each eluted separately with good resolution using a sodium chloride gradient.

Fractions 164 to 166 were pooled (pool CY183 III-3); ultrafiltered and stabilized on glycerol 50/50 w/w. The characteristics of the different pools are summarized in Table 2.

TABLE 2

| Characteristics of the glycosidases purified by DEAE TRISACRYL ART LS | | | |
|---|---|---|---|
| | Enzymatic activity (nkat/ml) | | |
| Product | α-L-A* | α-L-R** | β-D-G*** |
| Rhamnopyranosidase (*A. niger*) | 34.5 | 231 | 15.0 |
| Glucopyranosidase (*A. niger*) | 0 | 0 | 243 |
| Arabinofuranosidase (*A. niger*) | 4240 | 0 | 14.8 |

*α-L-arabinofuranosidase
**α-L-rhamnopyranosidase
***β-D-glucopyranosidase

EXAMPLE 2.4

Gel Permeation

A BIO-GEL P60 column (2.8×30 cm; BIO-RAD; Richmond, Va., U.S.A.) was pre-equilibrated with 0.01M sodium phosphate buffer (pH 8.8), at a flow rate of 30 ml/hour. A sample of 5 ml α-L-arabinofuranosidase stabilized on glycerol 1/1 w/w obtained from DEAE ART LS chromatography (Example 2.3, above) was applied to the column. The eluted protein was detected with a UV detector at an absorbance of 280 nm.

Fractions of 5 ml were collected and analyzed for their activity on p-nitrophenyl α-L-arabinofuranoside. Proteins were eluted in a single sharp peak which contained the α-L-arabinofuranosidase activity.

EXAMPLE 2.5

Adsorption Chromatography on BIO-GEL HTP

A BIO-GEL HTP column (2.8×20 cm; BIO-RAD; Richmond, Va., U.S.A.) was pre-equilibrated with 0.01M sodium phosphate buffer (pH 8.8), at a flow rate of 30 ml/hour. The pool of α-L-arabinofuranosidase from BIO-GEL P60 (35 ml) (obtained from Example 2.4, above) was applied to the pre-equilibrated BIO-GEL HTP column and chromatographed at a flow rate of 30 ml/hour. The proteins were eluted with an appropriate sodium phosphate buffer gradient (pH 8.8) from 0.01 to 0.2M.

Fractions of 5 ml were collected and analyzed for their α-L-arabinofuranosidase, β-D-glucopyranosidase and α-L-rhamnopyranosidase activities. The two latter enzymes were not detected in the standard conditions. The ABF B enzyme was eluted with the first major peak.

EXAMPLE 3

Characterization of the Purified *Aspergillus niger* α-L-arabinofuranosidase B (ABF B) Enzyme

EXAMPLE 3.1

High Performance Size Exclusion Chromatography (HPSEC) on TSK G3000 SW

To determine the homogeneity of the enzyme and to estimate the molecular weight, fractions 63, 64, 65, 66, 67 (as obtained from Example 2, above) were chromatographed on a TSK G3000 SW column (LKB, Produckter AB; Bromma, Sweden) under the following conditions. 100 1 aliquots of each fraction were injected on the TSK G3000 SW column, which was pre-equilibrated with sodium-potassium phosphate buffer (pH 7.00; 0.1M) at a flow rate of 0.5 ml/min. The eluted proteins were detected spectrophotometrically at an absorbance of 280 nm. Fractions of 0.5 ml were collected and the α-L-arabinofuranosidase activity was tested qualitatively with the colorimetric test on a microtitre plate.

The column was calibrated with standard molecular weight proteins (Pharmacia Gel filtration calibration kit; Pharmacia AB, Uppsala, Sweden). The chromatographic profile reveals the high homogeneity of the protein eluted in fraction 63 to 66. The molecular weight of the α-L-arabinofuranosidase B enzyme was determined to be approximately 70 kDa which agrees fairly closely to the molecular weight for the same enzyme as reported by van der Veen et al. ((1991) supra).

EXAMPLE 3.2

SDS-PAGE Electrophoresis

Fractions 62 to 66 (obtained from Example 2, above) were pooled and concentrated by ultrafiltration (cut-off=10,000× D). The characteristics of this sample were determined and are summarized below:

| | |
|---|---|
| Protein concentration: | 0.25 mg/ml |
| Activity on pNP-arabinofuranoside: | 38 nkat/ml |
| Specific activity: | 153 nkat/mg |

SDS PAGE electrophoresis confirms the high purity of the enzyme and the molecular weight as determined by HPSEC.

EXAMPLE 4

Amino Acid Sequence Determination of the N-termini of the Mature ABF B Protein and Two CNBr-Generated Peptide Fragments Approximately 10 μg of the purified ABF B was electrophoresed on a 7.5% SDS-polyacrylamide gel and electroblotted onto Immobilon membrane (Millipore), according to the method as described by Matsudaira ((1987) J. Biol. Chem., 262, 10035). The appropriate band was cut out and sent in for sequence determination (Eurosequence, Groningen). The following N-terminal sequence was obtained:

Gly-Pro-Xaa-Asp-Ile-Tyr-Glu-Ala-Gly-Asp-Thr-Pro-Xaa-Val-Ala-Ala    (Formula 1) (SEQ ID NO:1)

Approximately 100 μg of pure ABF B was digested overnight at room temperature in a volume of 150 μl 0.15 CNBr in 70% formic acid. Digestion products were separated on a 15% SDS-polyacrylamide gel and electroblotted onto Immobilon (Millipore; Matsudaira, supra). Two bands, of 29 and 15 kDa, were cut out and sequenced (Eurosequence, Groningen, the Netherlands). The following sequences were obtained from respectively the 29 (Formula 2) and 15 kDa fragment (Formula 3):

Gly-Pro-Xaa-Asp-Ile-Tyr-Glu-Ala-Gly-Asp-Thr-Pro-Xaa-Val-Ala-Ala    (Formula 2) (SEQ ID NO:1)

Xaa-Lys-Glu-Xaa-Ala-Ile-Ile-Leu-Gly-Ile-Gly-Gly-Asp-Xaa-Xaa-Asn-Gly-Ala    (Formula 3) (SEQ ID NO:2)

The amino acid sequence as depicted in Formula 2 is identical to the N-terminal sequence of the ABF B protein (see Formula 1), the 29 kDa band represents the N-terminal fragment of the protein, while the 15 kDa fragment represents an internal fragment.

EXAMPLE 5

Construction of an *Aspergillus niger* genomic library 5 g of *A. niger* HEM mycelium was ground in a mortar in liquid nitrogen until a fine white powder was obtained. The powder was lysed in 35 ml TES (10 mM Tris.HCl, pH 7.5; 50 mM EDTA; 150 mM NaCl)+1% SDS at 55° C. for a period of 2–4 hours. The lysate was extracted once with one volume phenol and several times with one volume phenol-chloroform, until the interphase was no longer visible. After a final extraction with one volume chloroform, the DNA was ethanol-precipitated. The pellet was dissolved in TE (10 mM Tris; 1 mM EDTA; pH 8.0) and RNase was added to a concentration of 1 μg/ml.

10 μg of this DNA was partially digested with Sau3AI in such a way that fragments were obtained with an average length of 10–20 kb. The resulting Sau3AI ends were partially filled in with Klenow polymerase using the nucleotides dGTP and dATP and ligated to LambdaGEM™-11 XhoI half-site arms (Promega). These arms contain partially filled-in XhoI sites (with dTTP and dCTP) and are purchased ready-for-use from the manufacturer. The ligated DNA was packaged using the Packagene in vitro packaging system (Promega). Titration of this primary genomic library on *E. coli* MB406 resulted in 8000 plaque-forming units (pfu).

EXAMPLE 6

Screening of the *A. niger* Genomic Library for the α-L-arabinofuranosidase B (abfB) Gene and Partial Characterization of Hybridizing Phage Clones Details of molecular cloning techniques are described by Sambrook et al. in *Molecular Cloning: A Laboratory Manual*, 2nd edition (1989; Cold Spring Harbor Laboratory Press). Enzyme incubations are performed following instructions described by the manufacturer.

The amino acid sequences as depicted in Formulas 1 and 3 (SEQ ID NO:1 and SEQ ID NO:2) were used for the construction of oligonucleotide mixtures AB1719 and AB2306 (see FIGS. 2 and 3). Inosine nucleotides were used in case of a degeneracy of the genetic code of four or more nucleotides.

Southern blots of 10 μg chromosomal *A. niger* HEM DNA digested with either BamHI, BglII, EcoRI or HindIII were hybridized overnight at 35° C. in 6×SSC, 5×Denhardt's solution, 0.5% SDS and 100 μg/ml denatured calf thymus DNA with 15 pmol of these oligo mixtures, after which the blots were washed two times during 10 min at 35° C. with 6×SSC, 0.1% SDS. Oligo AB1719 (FIG. 2, Formula 1a) (SEQ ID NO:3), gave a pattern of several distinct hybridizing bands per enzyme digest.

For the screening of the *A. niger* HEM genomic library, $2 \times 10^3$ pfu per plate were plated on three plates of 15 cm diameter using *E. coli* MB406 as plating bacterium. TB (10 g/l Bacto-tryptone; 5 g/l NaCl) medium plus 0.9% and 0.75% agar were used for the bottom and top, respectively. Duplicate filters (nitrocellulose, Millipore) were prepared from each plate and screened with oligo AB1719 using hybridization and washing conditions similar to those used for Southern Blot hybridizations. Five in duplo hybridizing plaques could be detected. Each plaque was removed with a Pasteur pipette and the phages were eluted from the agar plug in 0.5 ml Phage Buffer (20 mM Tris.HCl, pH 7.5; 100 mM NaCl; 10 mM MgSO$_4$). Plaques were purified by repeated plating of phages eluted from isolated agar plugs and subsequent screening with oligo AB1719. The five plaques were found to hybridize to a different extent with oligo AB1719:

| Plaque | Hybridization signal |
| --- | --- |
| 7 | +++++ |
| 8 | +++++ |
| 12 | ± |
| 45 | ++ |
| 53 | +++++ |

After plaque purification, DNA was isolated from phages originating from a single hybridizing plaque. Number 12 was omitted because of its low hybridization signal. Between 30,000–50,000 plaques were plated on 15 cm plates using TB without NaCl and agarose instead of agar in bottom and top. After overnight incubation, phages were eluted from the top agar by continuous shaking of the plate on a rocker platform during 90 minutes with 15 ml Phage Buffer. Halfway, the plates were given a quarter turn. The phage suspension was collected from the plates and centrifuged to remove cell debris. DNase and RNase were added to a final concentration of 1 μg/ml and the phage suspension was incubated 45 min at 37° C. Phages were PEG-precipitated for one hour on ice in 1M NaCl and 10% PEG 6000. After centrifugation, the phage pellet was resuspended in 1 ml Phage Buffer per plate and insoluble debris removed by centrifugation. SDS and EDTA were added to a final concentration of 0.2% and 15 mM, after which proteinase K was added to 50 μg/ml and the mixture incubated for 30 min at 65° C. After successive extractions with equal volumes of phenol, phenol/chloroform and chloroform, the DNA was precipitated from the aqueous phase with isopropanol. The DNA was dissolved in TE, containing 0.1 μg/ml RNase.

Figure 4:
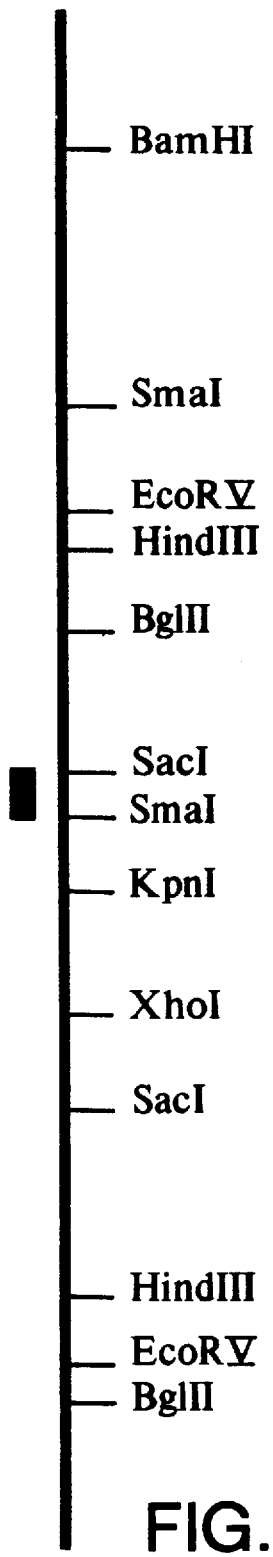
FIG. 4 Partial restriction enzyme map of the hybridizing phage clone 7.

Of each phage DNA, a partial restriction map was constructed (see FIG. 4—phage clone 7). Two of the phages clones (8 and 53) contained a fragment from the same genomic region of *A. niger*, while the others (7 and 45) contained different genomic fragments.

EXAMPLE 7

Isolation and Characterization of the abfB Gene

Phage DNA was digested until completion with enzymes recognizing a sequence of four successive nucleotides and the resulting fragments were ligated in pTZ18R or pUC18. The resulting colonies were transferred to nitrocellulose membranes and screened with oligo AB1719 to select plasmids with a hybridizing insert. Sufficiently small inserts were sequenced to identify the insert. Sequence analysis of a 2.8 kb SacI fragment of phage clone 7 was performed using a Sequenase® version 2.0 reagent kit (United States Biochemical) according to the manufacturer's instructions. The results of the sequence analysis (FIG. 5, Formula 4) (SEQ ID NO:5) demonstrate a sequence in which both the nucleotide sequence of oligo AB1719 and the amino sequence of the N-terminus of the ABF B protein could be detected (compare Formula 1 and FIG. 6, Formula 5) (SEQ ID NO:6).

The 2.8 kb SacI fragment was cloned into the *E. coli* plasmid pUC18. The resulting plasmid was given the designation pGBabfB and was deposited in *E. coli* strain DH5α at the Centraal Bureau voor Schimmelcultures (Baarn, the Netherlands on Mar. 11, 1991, under accession number CBS 156.91).

EXAMPLE 8

Introduction of the abfB Gene in *Aspergillus niger* N 593 by Co-transformation

The phage clone 7 DNA, obtained in Example 6 is introduced into *Aspergillus niger* by co-transformation of *Aspergillus niger* strain N593 using the *Aspergillus niger* pyrA gene as a selective marker on the plasmid pGW635 (Goosen et al. (1989) Mol. Gen. Genet. 219, 282) and the phage clone 7 DNA as the co-transforming DNA. For co-transformation, 1:20 molar ratios of transforming DNAs were added in order to favor the frequency of co-transformation.

To assay the co-transformation frequencies, the plasmid pNOM102 (Roberts et al. (1989) Curr. Genet., 15, 177) harboring the *E. coli* uidA gene, coding for β-glucuronidase (GUS) was used as co-transforming DNA.

PYRA+ transformants were subsequently transferred to X-glucuronide medium (Clontech, Palo Alto, Calif., U.S.A.; Roberts et al. (1989) supra) and scored for GUS activity. Blue colonies were scored as GUS+ phenotype, colourless as GUS- phenotype. *A. niger*, co-transformed with pNOM102 and pGW635 plasmids for transformation/selection respectively, gave co-transformation frequencies up to 85%.

Protoplasts were prepared from mycelium by growing *Aspergillus niger* N593 on minimal medium supplemented with 50 mM glucose, 0.5% yeast extract, 0.2% casamino acids and 10 mM uridine for 20 hours at 30° C. The minimal medium had the following composition (per 1000 ml): 6.0 g NaNO$_3$, 1.5 g KH$_2$PO$_4$, 0.5 g MgSO$_4$.7H$_2$O, 0.5 g KCl, 1 ml Visniac solution (Visniac, W. & Santer, M. (1957) Bact. Rev., 21, 195), carbon source as indicated, pH 6.0. The preparation of protoplasts of *A. niger* N593 and the transformation procedure was performed as described by Goosen et al. (1987) Current Genet., 11, 499.

The resulting PYR+ transformants were isolated, purified and tested for arabinofuranosidase production in shake flasks (see Example 9). Since no plate assay for the co-transformed gene was available, a Polymerase Chain Reaction (PCR) amplification test developed by D. Seth (Biotech International Ltd., Australia) as a quick screen to identify those transformants harbouring the non-selected gene was utilized. This PCR amplification test was performed as follows:

A few young strands of mycelium from PYR+ transformants were put in a 1.5 ml tube;

50 μl of a 2% SDS solution was added to this tube and heated at 95° C. for 10 minutes;

The heated sample was diluted 100 times with sterilized ultrapure water;

5 μl of the diluted sample was used for the PCR amplification;

The polymerase chain reactions were performed according to the supplier of AmpliTaq™ polymerase (Perkin Elmer Cetus). After denaturation (8 minutes at 100° C.) and addition of 1 μl AmpliTaq™ polymerase, the reaction mixtures were subjected to 25 amplification cycles (each: 2' at 94° C., 2' at 55° C., 3' at 72° C.) in a PHC-2 DNA-amplifier (Techne). After the last cycle, the polymerization step at 72° C. was extended to 7 minutes to complete all strands;

The PCR products were analyzed by agarose gel electrophoresis. The co-transformation frequencies ranged from 5–45% for this pyrA/PCR screening.

EXAMPLE 9

Screening of Co-Transformants for the Expression of the abfB Gene

The PYR$^+$ transformants obtained in Example 8 were analyzed for the expression of the abfB gene. The PYR$^+$ transformants harboring bacteriophage lambda 7 DNA are selected by the PCR amplification test.

Spores of these transformants were collected from cells grown for 5 days at 34° C. on potato-dextrose agar (Difco) plates.

Arabinofuranosidase production was tested in shake flasks under the following conditions:

Approximately 1×10$^6$ spores were inoculated in 100 ml pre-culture medium containing (per liter): 30 g sucrose, 2 g NaNO$_3$, 1 g K$_2$HPO$_4$, 0.5 g MgSO$_4$.7H$_2$O, 0.5 g KCl, 0.01 g FeSO$_4$.7H$_2$O, 5 g yeast-extract, 10 g malt-extract and 3 g carboxypolymethylene (B. F. Goodrich Company). The pH was adjusted to 6.1 with NaOH.

After growing for 48 hours at 34° C. in a rotary shaker (250 rpm), 5 ml of the grown culture was inoculated in a 100 ml main-culture P medium containing (per liter): 5 g soya meal, 4.4 g beet pulp, 3 g (NH$_4$)$_2$SO$_4$, 3 g glycine, 12 g (NH$_4$)$_2$HPO$_4$ and 0.24 g MnSO$_4$.H$_2$O. The pH was adjusted to 6.2 with H$_3$PO$_4$.

The mycelium was grown for at least a further 100 hours at 34° C. and at 250 rpm. Samples were taken at selected intervals. The mycelium was removed by filtration and the culture filtrate analyzed by SDS-polyacrylamide gel electrophoresis and by the arabinofuranosidase assay as described in Example 1.

The results of the arabinofuranosidase assays are presented in Table 3.

TABLE 3

Arabinofuranosidase production by co-transformation of A. niger N593 with Lambda clone 7

| PYR$^+$ transformant* of strain N593 | PCR assay$^a$ | α-L-arabinofuranosidase activity (nkat/ml) hours after inoculation | | | |
|---|---|---|---|---|---|
| | | 24 | 48 | 72 | 96 |
| *2  | −  | 8  | 13 | 22 | 6  |
| *6  | −  | 12 | 30 | 34 | 22 |
| *7  | −  | 13 | 31 | 36 | 25 |
| *9  | −  | 17 | 33 | 30 | 19 |
| *1  | +  | 37 | 50 | 43 | 35 |
| *8  | +  | 33 | 52 | 49 | 37 |
| *21 | +  | 44 | 57 | 62 | 48 |
| *34 | +  | 46 | 53 | 59 | 41 |

$^a$− indicates the absence of a PCR DNA fragment
+ indicates the presence of a PCR DNA fragment after agarose gel electrophoresis.

From the results presented in Table 3, it may be concluded that PCR positive transformants produce only 1.5–2 times more arabinofuranosidase than the PCR negative transformants, i.e. those who received only the selective pyrA marker from the plasmid pGW635.

EXAMPLE 10

Arabinofuranosidase Expression in Aspergillus Transformed with Expression Vectors Containing the abfB Gene Fused to the Promoter and Signal Sequences of the A. niger amyloglucosidase (glaA) Gene

EXAMPLE 10.1

Construction of the Expression Vector

All constructs were made using standard molecular biological procedures as described e.g. in Sambrook et al. (1989) *Molecular Cloning: A laboratory manual,* 2nd edition, Cold Spring Harbor Laboratory Press, N.Y.

To obtain overexpression of arabinofuranosidase in *Aspergillus niger*, an additional expression cassette has been made in which the abfB gene is under control of the *A. niger* amyloglucosidase (AG) promoter in combination with the 18 amino acid signal sequence of the glaA gene.

EXAMPLE 10.2

Construction of pAB6-1, pAB-6-3, pAB6-4, pAB6-31 and pAGEK1

The amyloglucosidase (AG) gene (glaA) of *A. niger* was isolated from plasmid libraries containing 3–4 kb EcoRI fragments or 13–15 kb HindIII fragments in the *E. coli* vector pUC19 (Yanisch-Perron et al. (1985) Gene, 33, 103; obtainable from e.g. Pharmacia LKB Biotechnology, Sweden) using the following AG-specific oligos:

AG-1: 5'-GACAATGGCTACACCAGCACCGCAACG-
    GACATTGTTTGGCCC-3'     (Formula 6) (SEQ ID NO:7)

AG-2: 5'-AAGCAGCCATTGCCCG-
    AAGCCGAT-3'     (Formula 7) (SEQ ID NO:8)

both based on the nucleotide sequence published for *A. niger* (Boel et al. (1984) EMBO J., 3, 1097–1102 ; Boel et al. (1984) Mol. Cell. Biol., 4, 2306). The oligonucleotide probes were derived from the sequence surrounding intron 2: oligo AG-1 is located 3' of the intron and has a polarity identical to the AG mRNA and oligo AG-2 is found upstream of intron 2 and is chosen antiparallel to the AG mRNA.

Figure 7:
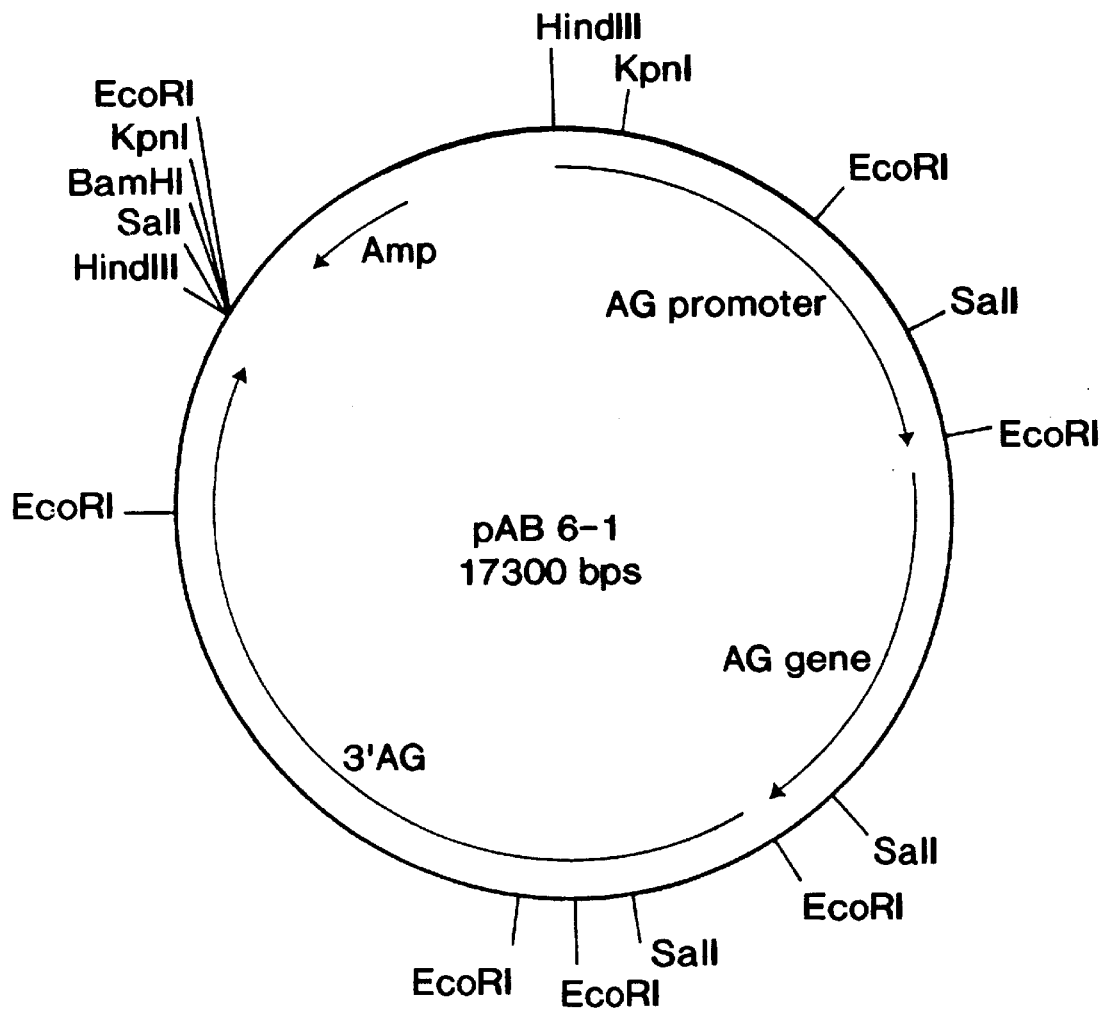
FIG. 7 Physical map of pAB 6-1. The 14.5 kb HindIII DNA insert in pUC19 contains the entire amyloglucosidase (AG) locus from *A. niger*.

From this screening, plasmid pAB6-1 was obtained which contains the glaA gene on a 14.5 kb HindIII fragment (see FIG. 7).

From plasmid pAB6-1 several subclones were made in pUC19: pAB6-3 which contains a 1.8 kb EcoRI fragment just upstream of the glaA gene and probably harbors regulatory sequences; pAB6-4 which contains a 4.6 kb HindIII - BglI fragment comprising the promoter of the glaA gene and a portion of the 5'-end of this gene.

Next, plasmid pAB6-3 was partially digested with EcoRI and treated with T4 polymerase. Into this plasmid, the HindIII plus EcoRI fragment of plasmid pAB6-4 was ligated, again after treatment with T4 polymerase. The resulting construct was designated pAB6-31; this construct contains a 3.6 kb upstream fragment of the glaA gene with a destroyed EcoRI site in the middle and an unique EcoRI site close to the glaA gene.

From plasmid pAB6-31, a 3.4 kb KpnI/EcoRI fragment harboring the same upstream sequences of the glaA gene was subcloned into the vector pTZ18R (Pharmacia, Sweden). The resulting construct was desginated pAGEK1.

EXAMPLE 10.3

Construction of pAGabfB1

Figure 8:
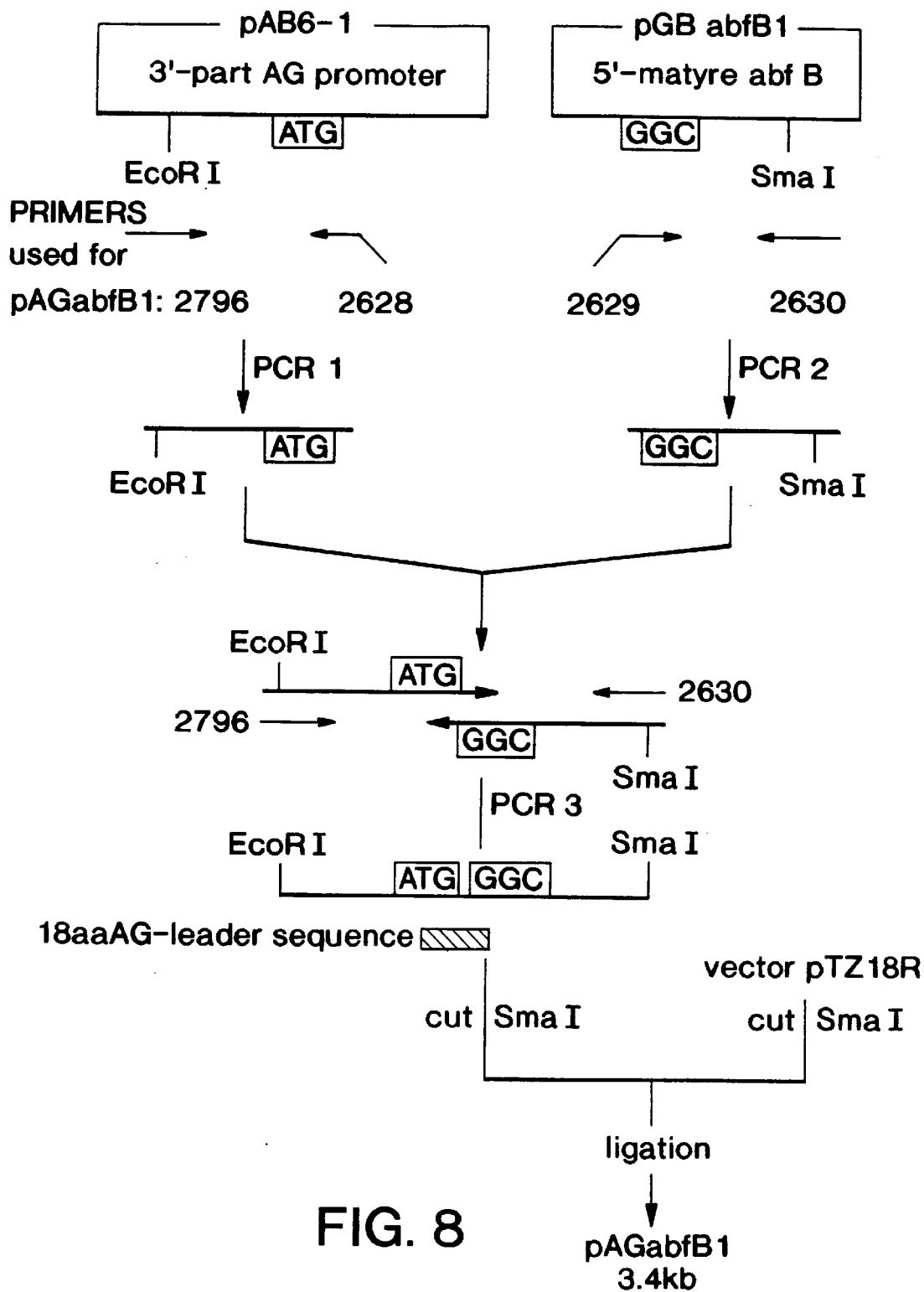
FIG. 8 A schematic view of the generation of AG/abfB gene fusions by the polymerase chain reaction (PCR). The sequences of all oligonucleotide primers used are indicated in the text.

Fusion of the AG-promoter and the 18 amino acid leader sequence of the glaA gene to the abfB structural gene encoding the mature protein were performed by the Polymerase Chain Reaction (PCR) method as presented schematically in FIG. 8.

As primers for the PCR-amplifications, four synthetic oligonucleotides were designed with the following sequences:
primer 2796: 5'-CTCTGCAGGAATTCAAGCTAG-3'
an AG-specific sequence around the EcoRI site approximately 250 bp upstream from the ATG initiation codon. (Formula 8) (SEQ ID NO:9)

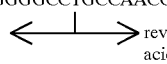

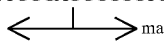

primer 2630:
5'-GCTTAGCCCGGGGGTGCTTGGGTCAGG-3'
an abfB-specific sequence located at the SmaI site on position 483. (Formula 11) (SEQ ID NO:12)

The PCR was performed as described by Pomp & Medrano (1991) Biotechniques, 10, 58, with minor modifications (see Example 8).

To fuse the AG sequences to the abfB coding sequences, two separate PCR's were carried out:
the first reaction (PCR(1) in FIG. 8) using pAB6-1 as template and oligos 2796 and 2628 as primers to amplify a 230 bp DNA fragment containing the 3'-fragment of the AG promoter and the 18 amino acid AG-leader sequence flanked at the 3'-border by the nucleotides of the abfB gene;
the second reaction (PCR(2) in FIG. 8) using pGBabfB1 as template and oligos 2629 and 2630 as primers to amplify a 300 bp DNA fragment containing the 5'-portion of the mature arabinofuranosidase B (abfB) gene flanked at the 5'-border by 18 nucleotides of the amyloglucosidase (AG) signal peptide.

The two DNA fragments generated by PCR were purified by gel electrophoresis and Sephaglas™ Band prep kit (Pharmacia, Sweden).

These two purified DNA fragments were used as templates in the third reaction (PCR (3) in FIG. 8) using oligos 2796 and 2630 as primers to generate the AG-arabinofuranosidase B fusion. The 530 bp DNA fragment was digested with SmaI, purified by agarose gel electrophoresis and Sephaglas™ Band prep kit, and ligated into the SmaI-cut pTZ18R vector.

The ligated DNA was transformed into E. coli electrocompetent Top10 cells as described by the supplier (Invitrogen corporation; San Diego, Calif., U.S.A.). Selection was made on Luria Broth (LB) plates containing Xgal (5-bromo-4-chloro-3-indolyl-β-D-galactoside), IPTG (isopropylthiogalactoside) and ampicillin. Plasmid DNA from white transformants was prepared as described by Andreoli, P. (1985) Mol. Gen. Genet., 199, 372 and analyzed with the restriction enzymes EcoRI and SmaI. Those transformants containing the 530 bp fusion DNA fragment were sequenced and designated pAGabfB1.

A schematic view of the construction of plasmid pAGabfB1 is presented in FIG. 8.

EXAMPLE 10.4

Construction of pAGabfB2 and pAGabfB3

A schematic view of these two plasmid constructions is presented in FIG. 9.

The E. coli vector pBluescript II SK(+), obtainable from Stratagene cloning systems (La Jolla, Calif., U.S.A.), was digested with EcoRI and XhoI and purified by agarose gelelectrophoresis.

The 530 bp EcoRI-SmaI fragment from plasmid pAGabfB1 was isolated and the 1.8 kb SmaI-XhoI fragment from pGBabfB1 (containing the mature abfB gene) was isolated (see Example 7). These two fragments were ligated into the EcoRI-XhoI cut-pBluescript II SK(+) vector and transformed to E. coli DH5α competent cells prepared according to a modified Hanahan procedure ((1983) J. Mol. Biol., 166, 557). Selection was made on LB plates containing Xgal, IPTG and ampicillin. Plasmid DNA from white transformants was prepared and analyzed with the restriction enzymes EcoRI and XhoI. The plasmid that harbored the desired 2.3 kb EcoRI-XhoI fragment was designated pAGabfB2.

For the construction of pAGabfB3, the remaining 3.4 kb upstream region of the AG-promoter was obtained by digestion of plasmid pAGEK1 with KpnI and EcoRI and purified by agarose gel electrophoresis.

The 2.3. kb EcoRI-XhoI fragment containing the AG-arabanase gene fusion was purified from plasmid pAGabfB2.

These two fragments were ligated into the pBluescript II SK(+) vector (which was cut with KpnI-XhoI) and used to transform E. coli DH5α competent cells as described above.

After plasmid DNA isolations and restriction enzyme analyses, the desired expression cassette pAGabfB3 was obtained (see FIG. 9).

EXAMPLE 10.5

Construction of pAGabfB4

To introduce a homologous selection marker for the transformation of Aspergillus niger strain N593 (Goosen et al. (1987) supra), the 3.8 kb XbaI fragment of plasmid pGW635 containing the pyrA gene (Goosen et al. (1989) supra), was inserted into the unique XbaI site of the pAGabfB3 expression cassette. The resulting expression/selection plasmid was designated pAGabfB4 and is shown in FIG. 10.

EXAMPLE 10.6

Construction of pAGabfB5

A 3.8 kb HindIII-XbaI fragment from plasmid pFYT3 (van Gorcom, R. F. et al. (1991) European Patent Application 0 420 358 A1) comprising the amdS selection gene from Aspergillus nidulans (Corrick et al. (1987) Gene, 53, 63) was isolated and inserted into the HindIII-XbaI cut-pAGabfB3 plasmid. The resulting expression/selection plasmid was designated pAGabfB5 and is depicted in FIG. 11.

EXAMPLE 10.7

Introduction of the pAGabfB3 and pAGabfB4 Expression Cassettes into Aspergillus niger N593

The plasmid pAGabfB3 was introduced into A. niger by co-transformation of strain N593 using the pyrA gene as a selective marker on the plasmid pGW635 (Goosen et al. (1989) supra) and the expression cassette pAGabfB3 as the co-transforming DNA.

Transformation of strain N593 with the expression cassette pAGabfB4 was performed as described by Kusters-van Someren et al. (1991) Curr. Genet., 20, 293.

The resulting PYR$^+$ transformants were isolated, purified and tested for arabinofuranosidase production in shake flasks using the process as described in Example 11.

As a control, transformants possessing only the vector pGW635 were tested.

EXAMPLE 10.8

Introduction of the pAGabfB5 Expression Cassette in Aspergillus niger Strain CBS 513.88

The plasmid pAGabfB5 was introduced in Aspergillus niger strain CBS 513.88 (deposited Oct. 10, 1988) using transformation procedures as described by Tilburn et al. (1983) Gene, 26, 205 and Kelly & Hynes (1985) EMBO J., 4, 475 with the following modifications:

mycelium was grown on Aspergillus minimal medium (Cove (1966) Biochem. Biophys. Acta, 113, 51) supplemented with 10 mM arginine and 10 mM proline for 16 hours at 30° C. in a rotary shaker at 300 rpm;

only Novozym 234 (NOVO Industri), and no helicase, was used for formation of protoplasts;

after 90 minutes of protoplast formation, 1 volume of STC buffer (1.2M sorbitol, 10 mM Tris-HCl pH 7.5, 50 mM CaCl$_2$) was added to the protoplast suspension and centrifuged at 2500 g at 4° for 10 minutes in a swinging-bucket rotor. The protoplasts were washed twice and resuspended in STC-buffer at a concentration of 108 cells/ml;

plasmid DNA was added in a volume of 10 μl in TE buffer (10 mM Tris-HCl pH 7.5, 0.1 mM EDTA) to 100 μl of the protoplast suspension;

after incubation of the DNA-protoplast suspension at 0° C. for 15 minutes, 200 μl of PEG solution was added dropwise (25% PEG 4000 (Merck), 10 mM Tris-HCl pH 7.5, 50 mM CaCl$_2$) and the incubation continued at room temperature for 10 minutes. Subsequently, 1 ml of PEG solution (60% PEG 4000 in 10 mM Tris-HCl pH 7.5, 50 mM CaCl$_2$) was added slowly, with repeated mixing of the tubes. After incubation at room temperature for 20 minutes, the suspensions were diluted with STC-buffer, mixed by inversion and centrifuged at 2000×g at 4° C. for 10 minutes. The protoplasts were resuspended gently in 200 μl STC-buffer and plated on Aspergillus selective minimal medium with 10 mM acetamide as the sole nitrogen source, 1M sucrose, solidified with 0.75% bacteriological agar n°1 (Oxoid). Growth was performed at 30° C. for 6–10 days.

The resulting transformants were replica-plated to selective acetamide minimal medium 1.2% agarose plates and incubated at 30° C. for 4–7 days.

After 4–7 days, fast growing and good sporulating transformants appear, against a very low background.

The amdS$^+$ transformants were purified by streaking for single colonies on selective acetamide minimal medium 1.2% agarose plates and tested for arabinofuranosidase production in shake flasks using the process as described in Example 11.

EXAMPLE 11

Expression of the arabinofuranosidase B Gene Under the Control of the AG Promoter and 18 Amino Acid AG Leader Sequence in Aspergillus niger Spores of purified transformants were collected from cells grown for 3–5 days at 34° C. on potato-dextrose agar (Difco) plates.

Approximatively 1×10$^8$ spores were inoculated in 100 ml pre-culture medium containing (per liter): 1 g KH$_2$PO$_3$; 30 g saccharose (maltose); 5 g yeast-extract; 10 g casein-hydrolysate; 0.5 g MgSO$_4$.7H$_2$O and 3 g Tween 80. The pH was adjusted to 5.5.

After growing overnight at 34° C. in a rotary shaker (250 rpm), 1 ml of the growing culture was inoculated in a 100 ml main-culture containing (per liter): 1 g KH$_2$PO$_3$; 70 g maltodextrin (Maldex MDO3, Amylum); 12.5 g yeast-extract; 25 g casein-hydrolysate; 2 g K$_2$SO$_4$; 0.5 g MgSO$_4$.7H$_2$O; 0.03 g ZnCl$_2$; 0.02 g CaCl$_2$; 0.05 g MnSO$_4$.4H$_2$O and 0.3 g FeSO$_4$. The pH was adjusted to 5.6.

The mycelium was grown for at least a further 140 hours at 34° C. and at 250 rpm. Samples were taken at selected intervals. The mycelium was removed by filtration and the culture filtrate analyzed by SDS-polyacrylamide gel electrophoresis and by the arabinofuranosidase assay as described in Example 1.

The N593 transformants harboring the pAGabfB3 or the pAGabfB4 expression cassette exhibit enhanced production of the ABF B enzyme as compared to the N593 transformants harboring only the pyrA selection marker.

The CBS 513.88 transformants harboring the pAGabfB5 expression cassette exhibit enhanced production of the ABF B enzyme as compared to the CBS 513.88 transformants harboring the p18FYT3 expression cassette.

EXAMPLE 12

Determination of Amino Acid Sequences

EXAMPLE 12.1

Amino Acid Sequence Determination of α-L-arabinofuranosidase A (ABF A)

Approximately 1–2 nmol α-L-arabinofuranosidase A (ABF A) obtained from a culture filtrate of *A. niger* N400, purified as described by van der Veen et al. ((1991) supra), was used in gas-phase sequencing (SON facility, Leiden, NL). The following sequence was determined:

Xaa-Xaa-(Leu)-Lys-Val-Xaa-Thr-Gln-
(Gly)-(Gly)            (Formula 12) (SEQ ID NO:13)

In addition, 2–4 nmol of the protein was cleaved by CNBr using the following methods: the protein was dialyzed against bidest for 18 hours after which the protein was freeze-dried. The powder was resuspended in 70% formic acid at a concentration of 1 mg/ml. To this solution a 200 fold excess of CNBr, with respect to the number of expected methionine residues, was added and the protein solution was incubated in the dark at room temperature for 24 hours The reaction mixture was freeze-dried and washed twice with bidest and resuspended in sample buffer (50 Mm Tris pH 6.8; 100 Mm dithiothreitol; 2% SDS 0.1% bromphenol blue and 10% glycerol). This solution was heated for 3 minutes at 100° C., after which the peptides were separated on a 15% SDS-polyacrylamide gel, followed by blotting onto Immobilon-P membrane (Millipore) according to the method described by Matsudaira, P. ((1987) J. Biol. Chem., 262, 10035). Membrane fragments containing 2–3 nmol of the particular peptide were washed with bidest and subjected to sequence analysis, according to the method described by Amons, R. ((1987) FEBS Lett., 212, 68). The following amino acid sequence was determined:

Leu-Gln-Asn-Pro-Gly-Leu-Gln-Gly-Thr-Ala-Pro-Xaa-Leu-Thr-
Ala(Gly)            (Formula 13) (SEQ ID NO14)

EXAMPLE 12.2

Amino Acid Sequence Determination of α-L-arabinofuranosidase B (ABF B)

A sample of the α-L-arabinofuranosidase B (ABF B) protein was obtained from a culture filtrate of *A. niger* N400 and purified as described by van der Veen et al. ((1991) supra). The following N-terminal amino acid sequence was determined as described in Example 12.1:

Xaa-Pro-Xaa-Asp-Ile-Tyr-Glu-Ala-Gly-
Asp-Thr-Pro            (Formula 14) (SEQ ID NO15)

In addition to this N-terminal sequence, additional sequences were obtained by sequencing CNBr peptides as described in Example 12.1:

Glu-Asn-Asn-Leu-Phe-Ser-(Gly)-Ala-Asp-Glu-(Gly)-Tyr-Asn-Ser-
(Thr)-Asp-Pro-Thr            (Formula 15) (SEQ ID NO:16)

Ser-Lys-Glu-Gly-Ala-Ile-Ile-Leu-Gly-Ile-Gly-Gly-Asp-Asn-Ser-
Asn-Gly-Ala-Gln-Gly            (Formula 16) (SEQ ID NO:17)

Thr-Ser-Gly-Tyr-Pro-Ser-Asp-Asp-Val-Glu-Asn-(Ser)-Val-Xaa-Gln-
Ile-Val-Ala            (Formula 17) (SEQ ID NO18)

The amino acid sequences of Formulas 14–17 are also found in the derived amino acid sequnce as provided in FIG. 6. This confirms that the ABF B enzyme is conserved in varying strains of *Asnergillus niger*.

EXAMPLE 12.3

Amino Acid Sequence Determination of endo 1,5-α-L-arabinanase (ABN A)

A sample of the endo 1,5-α-L-arabinanase (ABN A) protein was obtained from a culture filtrate of *A. niger* N400 and purified as described by van der Veen et al. ((1991) supra). The following N-terminal amino acid sequence was determined as described in Example 12.1:

Tyr-Ala-Asp-Pro-Gly-Ala-Xaa-Ser-Gly-
Val-Xaa-Thr-Thr            (Formula 18) (SEQ ID NO:19)

In addition to this N-terminal sequence, additional sequences were obtained by sequencing CNBr peptides as described in Example 12.1:

Glu-Tyr-Gly-Ser-Trp-Thr-Asp-His-Gly-Ser-Thr-Gly-Ile-Ala-Ser-
(Arg)-Xaa-Ala-Lys-Ile            (Formula 19) (SEQ ID NO:20)

EXAMPLE 13

Molecular Cloning and Analysis of the *Aspergillus niger* α-L-arabinofuranosidase A Gene (abfA)

EXAMPLE 13.1

Construction of the cDNA Expression Library

EXAMPLE 13.1.1

Induction and Isolation of mRNA

*A. niger* N572 (Witteveen et al. (1989) J. Gen. Microbiol., 135, 2163) was precultivated for 24 hours on minimal medium containing 1% D-glucose as a carbon source, after which mycelium was harvested by filtration and washed with sterile saline. The mycelium was then transferred to fresh medium containing 1% (w/v) L-arabitol. After 16 hours induction, the mycelium was recollected by filtration and washed thoroughly with sterile saline. The mycelium was subsequently frozen in liquid nitrogen after which it was powdered using a Microdismembrator (Braun). Total RNA was isolated from mycelial powder according to the guanidine monothiocyanate/LiCl protocol of Cathala et al. ((1983) DNA 2, 329), except that SDS was omitted from the solubilization buffer. Poly $A^+$ RNA was isolated from 1 mg of total RNA by oligo(dT)-cellulose chromatography (Aviv & Leder (1972) Proc. Nat. Acad. Sci. U.S.A., 69, 1408; Sambrook et al. (1989) *Molecular Cloning: a Laboratory*

*Manual,* 2nd ed., Cold Spring Harbor Laboratory Press, N.Y.) with the following modifications: 10 mM HEPES pH 7.6 was used as a buffer and SDS was omitted from all solutions, the loading buffer was supplemented with 9% (v/v) dimethylsulfoxide.

EXAMPLE 13.1.2

Construction and Immunochemical Screening of the cDNA Expression Library cDNA was synthesized from 5 µg poly A$^+$ RNA and ligated into bacteriophage lambda Uni-ZAP XR using the ZAP™-cDNA synthesis kit (Stratagene) according to the manufactors instructions. After ligation of the cDNA into Uni-ZAP XR vector-arms, the phage DNA was packaged using Packagene™ extracts (Promega). Ligation of 200 ng cDNA in 1 µg vector arms and subsequent packaging of one-fifth of the reaction mixture results in a primary library consisting of 2×10$^5$ recombinant phages. The primary library was amplified using *E. coli* PLK-F↑, titrated and stored at 4° C.

Screening of the cDNA expression library obtained was performed essentially as described by Young and Davies ((1983) Science 222, 778). In short, 5000 plate forming units (pfu) of the amplified stock were plated on NZYCM medium (per 1000 ml: 10 g NZ amine, 5 g NaCl, 5 g yeast extract, 1 g casamino acids, 2 g MgSO$_4$.7H$_2$O, pH 7.5—for plates, 12 g agar was added, for topagarose 7 g agarose) using *E. coli* BB4 (Stratagene) cells as a host in 0.6% topagarose. Plates were incubated for 5 hours at 37° C., after which they were covered with nitrocellulose filters which were previously soaked in 10 mM IPTG and air-dried. Plates were then further incubated for 6 hours at 37° C. Plates were cooled to 4° C. and the position of the filters on the plates was marked before they were removed. The filters were incubated for 15 minutes in 0.5M NaCl, 0.05% Tween 20 (Biorad), 20 mM Tris-HCl pH 7.5 with gentle shaking, this was repeated once. The bacterial debris was removed by gentle scrubbing with gloved hands. Phages expressing a fusion protein containing a part of the α-L-arabinofuranosidase A (ABF A) protein were identified by probing the filters with anti α-L-arabinofuranosidase A antiserum and subsequent detection using an alkaline phosphatase conjugate, according to the procedure described for Western blots in the manufacturer's instructions (Biorad). In two experiments, 5×10$^3$ and 5×10$^4$ pfu of the amplified library were screened for expression of α-L-arabinofuranosidase A cDNA: two and nine positives were found, respectively. Upon purification and excision, the plasmids were isolated by growing the resulting colonies overnight in LB medium (per 1000 ml: 10 g trypticase peptone (BBL), 5 g yeast extract (BBL), 10 g NaCl, 0.5 mM Tris-HCl pH 7,5) containing 100 µg/ml ampicillin. From the cultures, plasmid DNA was isolated by the alkaline lysis method as described by Maniatis et al. ((1982) Molecular Cloning, a Laboratory Manual, Cold Spring Harbor Laboratory, N.Y., 368–369). The lengths of the cDNA insert were determined by digestion with EcoRI and XhoI and subsequent agarose electrophoresis. The clone containing the largest insert (1.3 kb), designated pC1X1, was subjected to a limited restriction analysis (FIG. 12).

EXAMPLE 13.2

Screening of the *A. niger* Genomic Library for the α-L-arabinofuranosidase A Gene (abfA) and Isolation of the Gene

EXAMPLE 13.2.1

Screening of the *A. niger* Genomic Library for abfA Gene

An *A. niger* N400 genomic library was constructed as described by Harmsen et al. ((1990) supra). To screen the library for the abfA gene, 10$^4$ pfu per plate were plated in NZYCM topagarose containing 0.7% agarose on 85-mm-diameter NZYCM (1.2% agar) plates as described (Maniatis et al. (1982) supra, 64).

Plaque hybridization, using nitrocellulose replicas, was performed as follows: 6×10$^4$ pfu were plated with *E. coli* BB4 cells in 0.6% topagarose. After overnight incubation of the plates at 37° C., two replicas of each plate were made on nitrocellulose filters as described by Maniatis et al. ((1982) supra, 320). The filters were wetted and washed for 60 minutes at room temperature in 3×SSC, after which they were prehybridized at 68° C. for two hours in prehybridization buffer containing: 6×SSC, 0.5% SDS, 5×Denhardt's solution and 100 µg/ml heat denatured herring sperm DNA (Boehringer Mannheim). The SSC solution was made from a 20×SSC stock (per 1000 ml: 175.3 g NaCl, 107.1 g sodium citrate.5.5H$_2$O, pH 7.0). The 5×Denhardt's solution was made from a 100×stock solution (per 500 ml: 10 g Ficoll-400, 10 g polyvinyl pyrrolidone, 10 g Bovine Serum Albumin (Pentax Fraction V)). After two hours prehybridization, the prehybridization buffer was replaced by hybridization buffer which was identical to the prehybridization buffer, except that this buffer contained the $^{32}$P-labelled 1.0 kb PstI fragment from cDNA clone pC1X1 (FIG. 12), isolated and labelled as described by van den Broeck et al. ((1992) European Patent Application 0463 706 A1—see Examples 2.1 and 7.1). The filters were hybridized for 18 hours at 68° C. After hybridization, the filters were washed twice at 68° C. for 30 minutes in 2×SSC/0.1% SDS, followed by two washes for a period of 30 minutes at 68° C. in 0.2×SSC/0.1% SDS. The air-dried filters were taped on a sheet of Whatman 3MM paper, keying marks were made with radioactive ink and the Whatman paper and filters were covered with Saran Wrap™. Hybridizing plaques were identified by exposure of Kodak XAR X-ray film for 18 hours at −70° C. using an intensifying screen.

18 hybridizing plaques, appearing in duplicate on the replica filters, were identified: lambda$_{abf}$A1 to lambda$_{abf}$A18. Each positive plaque was picked from the plate using a Pasteur pipette and the phages were eluted from the agar plug in 1 ml of SM buffer (per 1000 ml: 5.8 g NaCl, 2.0 g MgSO$_4$.7H$_2$O, 50 ml 1M Tris-HCl pH 7.5, 5 ml 20% gelatin) containing 20 µl chloroform, as described by Maniatis et al. ((1982) supra, 64). The phages obtained were purified by repeating the procedure described above using filter replicas from plates containing 50–100 plaques of the isolated phages.

After purification, the phages were propagated by plating 5×10$^3$ phages on NZYCM medium. After overnight incubation at 37° C., confluent plates were obtained, from which the phages were eluted by adding 5 ml SM buffer and storing the plates for 2 hours at 4° C. with intermittent shaking. After collection of the supernatant using a pipette, the bacteria were removed from the solution by centrifugation at 4,000×g for 10 minutes at 4° C. To the supernatant, 0.3% chloroform was added and the number of pfu was determined by titration as described van den Broeck et al. ((1992), supra, see Example 2.4). These phage stocks contained approximately 10$^{10}$ pfu/ml.

EXAMPLE 13.2.2

Isolation of DNA from Bacteriophage lambda

Four of the isolated phages (lambda$_{abf}$A1, lambda$_{abf}$A5, lambda$_{abf}$A6 and lambda$_{abf}$A12) were propagated by combining 5×10$^9$ *E. coli* LE392 bacteria (Murray, N. (1977)

Mol. Gen. Genet., 150, 53) in 300 μl SM buffer with 2×10⁶ phages and incubating at 37° C. for 15 minutes. After the incubation period, the infected bacteria were used to inoculate 100 ml prewarmed (37° C.) NZYCM medium and were subsequently incubated for 9–12 hours at 37° C. in a New Brunswick rotation shaker at 250 rpm, after which period the bacteria were lysed. The bacterial debris was removed by centrifugation for 10 minutes at 10 krpm at 4° C. in a Sorvall High speed centrifuge. The phages were precipitated from the supernatant obtained (100 ml) by the addition of 10 g polyethylene glycol-6000 and 11.7 g NaCl and storing the solution overnight at 4° C. The precipitated phages were collected by centrifugation at 14,000×g at 4° C. for 20 minutes. The supernatant was removed by aspiration, while the last traces of liquid were removed using a paper towel. The phages were carefully resuspended in 4 ml SM buffer and extracted once with an equal volume of chloroform.

Before the DNA was extracted from the phage particles, DNA and RNA originating from the lysed bacteria was removed by incubation of the phage suspension with DNase I and RNase A (both 100 μg/ml) for 30 minutes at 37° C. The phage DNA was subsequently released from the phages by the addition of EDTA to a final concentration of 20 mM, while the protein was removed from the solution by extracting twice with an equal volume of a solution of phenol/chloroform/isoamyl alcohol (25:24:1). After separation of the phases by centrifugation using a Sorvall centrifuge (14,000×g, 10 minutes), the aqueous phase was extracted once with an equal volume of a solution of chloroform/isoamyl alcohol (24:1). The phases were separated by centrifugation, after which the DNA was precipitated from the aqueous phase by :the addition of 0.1 vol. 5M sodium perchlorate and 0.1 vol. isopropanol, followed by incubation on ice for 30 minutes. The DNA was recovered by centrifugation for 10 minutes at 4° C. (14,000×g). The supernatant was removed by aspiration, after which the DNA was resuspended in 400 μl TE buffer. The DNA was precipitated once again from this solution by the addition of 0.1 vol. 3M sodium acetate and 2 vol. ethanol. The DNA was collected by centrifugation for 10 minutes at 4° C. (14,000×g). The supernatant was removed by aspiration, the remaining pellet was briefly dried under vacuum, after which the DNA was resuspended in 125 μl TE buffer containing 0.1 μg/ml RNase A. This purification procedure results in the isolation of approximately 50–100 μg DNA from each phage.

EXAMPLE 13.2.3

Restriction Analysis of abfA Containing Phages

The DNA isolated from phages lambda$_{abf}$A1, lambda$_{abf}$A5, lambda$_{abf}$A6 and lambda$_{abf}$A12 was analyzed by Southern analysis. The DNA was digested for 3 hours at 37° C. in a reaction mixture composed of the following solutions: 5 μl (approximately 1 μg) DNA solution; 2 μl of the appropriate 10×React buffer (BRL); 10 Units restriction enzyme (BRL) and sterile distilled water to give a final volume of 50 μl. After digestion, the DNA was precipitated by the addition of 0.1 vol. 3M sodium acetate and 2 vol. ethanol. The DNA was collected by centrifugation for 10 minutes at room temperature (14,000×g). The supernatant was removed by aspiration and the remaining pellet was briefly dried under vacuum and resuspended in 20 μl sterile distilled water. After the addition of 4 μl DNA loading buffer (0.25% (w/v) bromophenol blue, 0.25% (w/v) xylene cyanol, 15% (w/v) Ficoll type 400 in H₂O), the samples were incubated for 10 minutes at 65° C. and rapidly cooled on ice, before loading the samples on a 0.6% agarose gel in TAE buffer (50×TAE buffer per 1000 ml: 242.0 g Trizma base (Sigma), 57.1 ml glacial acetic acid, 100 ml 0.5M EDTA pH 8.0). The DNA fragments were separated by electrophoresis at 25 V for 15–18 hours.

After electrophoresis, the DNA was transferred and denatured by alkaline vacuum blotting (VacuGene XL, Pharmacia LKB) to nylon membrane (Gene Bind 45, Pharmacia LKB) as described in the instruction manual (pp. 25–26) and subsequently prehybridized and hybridized using a ³²P-labelled 1 kb PstI fragment and hybridization conditions as described in Example 12.2.1. The hybridization pattern was obtained by exposure of Kodak XAR-5 X-ray film for 18 hours at −70° C. using an intensifying screen.

The restriction patterns obtained were used to derive a partial restriction map of the genomic region of the abfA gene. A 8.5 kb NsiI/XbaI fragment was selected for subcloning.

EXAMPLE 13.2.4

Subcloning of the A. niger abfA Gene

From phage lamoda$_{abf}$A5, the 8.5 kb NsiI/XbaI fragment was isolated by digesting the phage DNA and subsequent agarose electrophoresis. The fragment was cut from the agarose gel, after which it was recovered from the piece of agarose by electro-elution using ISCO cups. A dialysis membrane was mounted on both the large and the small containers of this cup, the cup was filled with 0.005×TAE and the piece of agarose was placed in the large container of the cup. The cup was subsequently placed in the electro-elution apparatus, the large container in the cathode chamber contained TAE and the small container at the anode chamber contained TAE/3M sodium acetate. The fragments were electro-eluted at 100 V for a period of 2 hours. After this period, the cup was taken from the electro-elution apparatus and the buffer was removed from the large container, while the buffer was only removed from the upper part of the small container. The remaining buffer (200 μl) containing the DNA fragments was dialyzed in the cup against distilled water for a period of 30 minutes. Finally, the DNA was precipitated by the addition of 0.1 vol. 3M sodium acetate (pH 5.6) and 2 vol. cold (−20° C.) ethanol. The DNA was collected by centrifugation (Eppendorf centrifuge) for 30 minutes at 14,000×g. and 4° C. After removal of the supernatant, the DNA pellet was dried using a Savant Speedvac vacuum centrifuge. The DNA was dissolved in 10 μl TE buffer and the concentration was determined by agarose electrophoresis, using lambda DNA with a known concentration as a reference and ethidium bromide staining to detect the DNA.

The fragment obtained was ligated in the vector pGEM-7Zf(+), which was digested with NsiI and XbaI prepared as follows: 1 μl (1 μg/μl) pGEM-7Zf(+) was mixed with 2 μl 10×React 1 (BRL), 1 μl (10 U/μl) NsiI, 1 μl (10 U/μl) XbaI and 16 μl sterile distilled water. The DNA was digested for 1 hour at 37° C. The vector was isolated from a 0.6% agarose gel as described above.

The 8.5 kb NsiI/XbaI fragment was ligated in the vector, resulting in the plasmid pIM900, by the following procedure: 100 ng pGEM-7Zf(+) fragment was mixed with 100 ng 8.5 kb NsiI/XbaI fragment and 4 μl 5×ligation buffer (composition: 500 mM Tris-HCl (pH 7.6); 100 mM MgCl₂; 10 mM ATP; 10 mM dithiotreitol; 25% PEG-6000) and 1 μl (1.2 U/μl). T₄ DNA ligase (BRL) was added to this mixture to a final volume of 20 μl. After incubation for 16 hours at 14° C., the mixture was diluted to 100 μl with sterile water.

10 μl of the diluted mixture was used to transform *E. coli* JM101 competent cells (Yanish-Perron et al. (1985) Gene, 33, 103), prepared by the CM1, CM2 method as described in the Pharmacia Manual for the M13 cloning/sequencing system. A selection of six of the resulting colonies were grown overnight in LB medium containing 100 μg/ml ampicillin. Plasmid DNA was isolated from the cultures by the alkaline lysis method as described by Maniatis et al. ((1982) supra, 368), which was used in restriction analysis to select a clone harboring the desired plasmid, pIM900. Plasmid DNA was isolated on a large scale from 500 ml cultures of *E. coli* JM101 which contained pIM900. The cultures were grown in LB medium containing 100 μg/ml ampicillin (Maniatis et al. (1982) supra, 86). The plasmid was purified by CsCl centrifugation, phenolyzed, ethanol precipitated and dissolved in 400 μl TE. Approximately 500 μg was obtained.

The plasmid pIM900 was further analyzed using restriction enzymes resulting in a restriction map as shown in FIG. 13.

The plasmid pIM900 containing the abfA gene was recloned into *E. coli* JM109 and was deposited at the Centraal Bureau voor Schimmelcultures (Baarn, the Netherlands on Mar. 17, 1992, under accession number CBS 187.92).

EXAMPLE 13.3

The Primary Structure of the abfA Gene

EXAMPLE 13.3.1

Sequence Analysis of the *A. niger* abfA Gene

The sequence of the *A. niger* abfA gene, its promoter-regulation region, the structural gene and the termination region, was determined by subcloning fragments from pIM900 in M13mp18/mp19, in combination with the use of specific oligonucleotides as primers in the sequencing reactions.

For nucleotide sequence analysis, restriction fragments were isolated as described in Example 13.2.4 and were then cloned in bacteriophage M13 mp18/19 RF DNA vectors (Messing, J. (1983) Methods in Enzymology, 101C, 20; Norrander et al.(1983) Gene, 26, 101), which were digested with the appropriate restriction enzymes. The nucleotide sequences were determined by the dideoxynucleotide chain-termination procedure (Sanger et al. (1977) Proc. Nat. Acad. Sci. U.S.A., 74, 5463) using the Pharmacia T7 DNA polymerase sequencing kit. Computer analysis was performed using the PC/GENE program. The nucleotide sequence of the abfA gene as determined is provided in FIG. 14 (Formula 20). The amino acid sequence of the ABF A protein, as derived from the abfA cDNA sequence, is provided in FIG. 15 (Formula 21).

EXAMPLE 13.3.2

Characterization of the abfA Gene

The sequence comprising the abfA structural gene (FIG. 14, Formula 20) is preceded by a 1246 nucleotide long upstream region. No putative TATA box is found, the sequence TTAATTT at position 1156–1162, resembles most closely such a sequence. However regions which are extreme rich in CT are found in front of the translation initiation site (Gurr et al. (1987) In: Gene Structure in Eukaryotic Microbes, Vol. 22, Kinghorn, J. R. (editor), IRL Press, Oxford, 93).

The structural portion of the abfA gene ranges from position 1247 until position 3483 and contains seven introns. Intron A is a putative intron, based on the consensus sequences for fungal introns (Gurr et al. (1987) supra), the position of the six other introns is established by sequencing the cDNA fragment in pC1X1 and pC2X1.

The abfA gene encodes a protein 628 amino acids in length (FIG. 15, Formula 21) ((SEQ ID NO:22), as derived from the abfA cDNA sequence. The N-terminal amino acid sequence, as determined in Example 12.1 (Formula 12) (SEQ ID NO:13) is preceded by a 25 amino acids long hydrophobic sequence. The amino acid sequence determined from the CNBr peptide (Formula 13) (SEQ ID NO:14) is found in the sequence from position 38 until position 52. The mature ABF A protein is 603 amino acids in length, and has a deduced molecular weight of 65378 Da and a theoretical IEP of 3.7. The deduced molecular weight values for this enzyme differs from those reported in the literature as mentioned above (see Rombouts et al., supra and van der Veen et al., supra). This is most likely to be attributable to the literature evaluations being made on the glycosylated protein whereas the deduced molecular weight of the ABF A protein found in the present example is based strictly on the unglycosylated protein.

EXAMPLE 14

Expression of the Cloned abfA Gene in *A. niger* and *A. nidulans*

EXAMPLE 14.1

Introduction of the abfA Gene in *A. niger* N593 and *A. nidulans* G191 by Cotransformation The plasmid pIM900 was introduced into *A. niger* by cotransformation of *A. niger* N593 using the *A. niger* pyrA gene, located on the plasmid pGW613 (Goosen et al. (1987) supra), as a selective marker and the plasmid pIM900 as the cotransforming plasmid. Analogously the gene was introduced into *A. nidulans* G191 (Balance & Turner (1985) Gene, 36, 321) using the above-mentioned plasmids.

Protoplasts from both strains were prepared from mycelium obtained after growth on minimal medium supplemented with 0.5% yeast extract, 0.2% casamino acids, 50 mM glucose and 10 mM uridine for 20 hours at 30° C. The preparation of protoplasts and the transformation procedure was performed as described by Goosen et al. ((1987) supra), using 3 μg pGW613 and 50 μg pIM900.

The PYR$^+$ transformants obtained were then analyzed for the expression of the abfA gene by SDS-PAGE followed by Coomassie Brilliant Blue R250 staining or Western blot analysis and by measuring the activity in the culture filtrate.

EXAMPLE 14.2

Screening of Transformants for the Expression of the abfA Gene

The transformants obtained in Example 14.1 were analyzed for the expression of the abfA gene product, the ABF A protein. Four transformants of each strain were selected and grown on minimal medium supplemented with 0.1% yeast extract containing 1% sugar beet pulp as a sole carbon source. After 24 hours of growth at 30° C., the mycelium was removed by filtration and the arabinofuranosidase activity of culture filtrate was measured using para-nitrophenyl-α-L-arabinofuranoside (PNA) as decribed by van der Veen et al. ((1991) supra). In addition, the culture filtrate was analyzed by SDS-polyacrylamide gel electrophoresis (Laemmli, U.K. (1970) Nature, 220, 680) using a gel containing 10% acrylamide followed by Coomassie Brilliant Blue R250 staining (in the case of the *A. nidulans* transformants) and followed by Western blotting (in the case of the *A. niger* transformants). The ABF A protein was detected on nitrocellulose after electroblotting and incubation with polyclonal antibodies raised against the ABF A protein which was purified as described in Example 12.1. The bound antibody was detected after incubation with goat-anti-mouse antibody conjugated to alkaline phosphatase, according to the Biorad instruction manual.

Figure 16A:
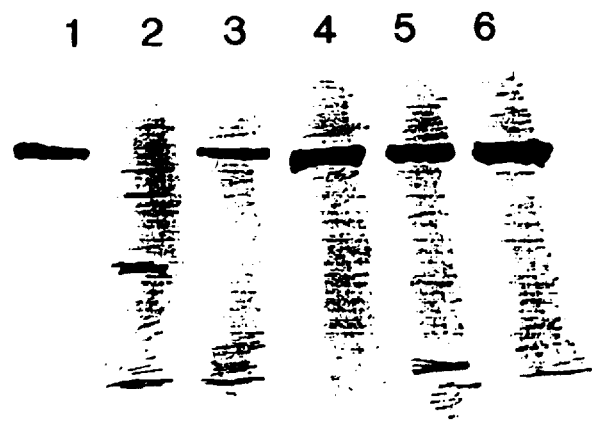
Figure 16B:
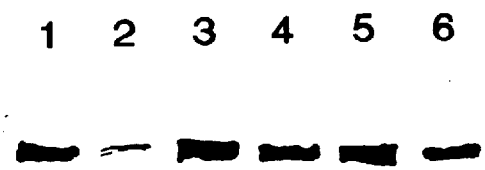

All four transformants of both strains analyzed overproduced the ABF A protein as detected by Coomassie Brilliaint Blue staining (FIG. 16A) or by Western blotting (FIG. 16B). Furthermore, an increased level of activity was found in the culture filtrate of both strains (Table 4 and Table 5).

TABLE 4

PNA hydrolyzing activity in culture medium of *Aspergillus nidulans* wild type WG096 (Uitzetter, J.H.A.A. (1982) "Studies on carbon metabolism in wild type and mutants of *Aspergillus nidulans*", PhD Thesis, Wageningen Agricultural University, Wageningen, The Netherlands) and abfA transformants at 24 hours of growth on sugar beet pulp as a carbon source.

| Strain | Activity (U/ml culture medium) |
| --- | --- |
| WG096 | 0.16 |
| G191::pIM900-1 | 1.34 |
| G191::pIM900-2 | 2.64 |
| G191::pIM900-3 | 2.13 |
| G191::pIM900-4 | 2.63 |

TABLE 5

PNA hydrolyzing activity in culture medium of *Aspergillus niger* wild type N402 and abfA transformants at 24 hours of growth on sugar beet pulp as a carbon source.

| Strain | Activity (U/ml culture medium) |
| --- | --- |
| N402 | 0.35 |
| N593::pIM900-1 | 2.48 |
| N593::pIM900-2 | 1.25 |
| N593::pIM900-3 | 1.99 |
| N593::pIM900-4 | 1.79 |

EXAMPLE 15

Molecular Cloning of the *Aspergillus niger* endo 1, 5-α-L-arabinanase (abnA) Gene

EXAMPLE 15.1

Construction of the cDNA Expression library

EXAMPLE 15.1.1

Induction and Isolation of mRNA

Figure 17:
Figure 18:
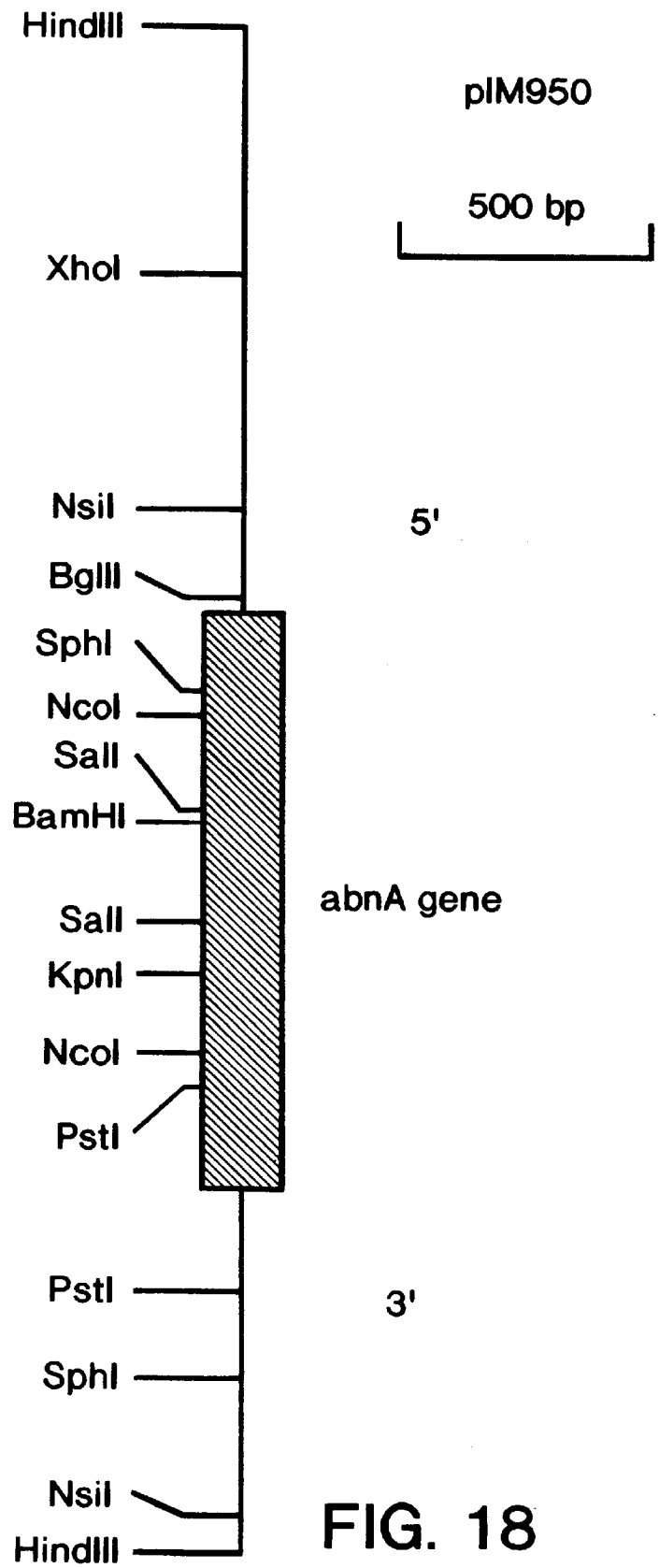

*A. niger* N572 was precultivated for 24 hours on minimal medium containing 1% glucose as a carbon source and supplemented with 0.1% yeast extract and 1 mg/L nicotinamide, after which the mycelium was harvested by filtration and washed with sterile saline. The mycelium was then divided into eight equal portions and each portion was then transferred to a 250 ml erlenmeyer flask containing 50 ml minimal medium with 1% arabitol. These cultures were then incubated at 30° C. for time intervals of 0, 1, 2, 3, 4, 5, 6 and 7 hours. For each time-point, the mycelium was harvested, washed with cold saline, frozen using liquid nitrogen and stored at −70° C. The induction patterns of endo 1,5-α-L-arabinanase A (ABN A) and ABF B were studied by Western blot analysis of 50 times concentrated culture samples of each of the time-points taken. ABF B was present in the culture medium 1 hour after transfer, while ABN A was found after 2 hours (FIG. 17).

From the mycelium harvested at time-points of 1, 2, 3, 4, 5 and 6 hours of incubation, RNA was isolated as described in Example 13.1.1.

EXAMPLE 15.1.2

Construction and Immunochemical Screening of the cDNA Expression Library

Half of the RNA of each time-point was pooled and the combined RNA sample was used to synthesize cDNA and construct an expression library as described in Example 13.1.2. After ligation of the cDNA into the vector and subsequent packaging of the DNA, a primary library of $3 \times 10^4$ phages was obtained. This primary library was amplified and screened using antibodies raised against ABN A (van der Veen et al. (1991) supra) as described in Example 13.1.2. Screening of $5 \times 10^4$ phages resulted in the isolation of a single positive clone. The length of the cDNA insert was determined by digestion with EcoRI/XhoI and subsequent agarose electrophoresis. The cDNA fragment was approximately 700 bp in length.

EXAMPLE 15.2

Screening of the *A. niger* Genomic Library for the endo 1,5-α-L-arabinanase (abnA) Gene and Isolation of the Gene Using a 550 bp KpnI fragment (which was derived from the cDNA described in Example 15.1.2. and isolated and labelled as described in Example 13.2.1), the *A. niger* N400 genomic library was screened for the abnA gene, as described in Example 13.2.1. Screening of $6 \times 10^4$ phages resulted in the isolation of six hybridizing phages. These phages were purified as described in Example 13.2.1, following which DNA was isolated from each of the phages as described in Example 13.2.2. The DNA obtained was used for restriction analysis as described in Example 13.2.3, which resulted in a partial restriction map. Using this restriction map, a 3.1 kb HindIII was selected for subcloning of the abnA gene into the vector pEMBL19 as described in Example 13.2.4, which resulted in the plasmid pIM950. This plasmid was further analyzed using restriction enzymes, providing the restriction map shown in FIG. 18.

The plasmid pIM950 containing the abnA gene was recloned into *E. coli* JM109 and was deposited at the Centraal Bureau voor Schimmelcultures (Baarn, the Netherlands on Mar. 17, 1992, under accession number CBS 188.92).

EXAMPLE 15.3

Screening for cDNA Clones Hybridizing to 5' End of the abfB Gene and the abnA Gene The cDNA library described in Example 15.1.1 and 15.1.2 was screened using $^{32}$P-labelled fragments. From the abfB gene, an approximately 550 bp EcoRI/SalI fragment from plasmid pGBabfB1, was used as a probe. From the abnA gene, an approximately 300 bp SphI/BamHI fragment from plasmid pIM950, was used as a probe. The cDNA library was plated and screened with the labelled fragments as described in Example 13.2.1. Screening of 10 phages resulted in the isolation of 36 phages hybridizing to the abnA fragment and 8 phages hybridizing to the abfB fragment. For both genes, three phages were purified, the plasmid excised and isolated as described in Example 13.1.2. Sequencing of the 5'-termini of these cDNA fragments gave identical 5' ends for all three clones of both the abfB as well as the abnA gene. The cDNA of the abfB gene starts at position 120 (FIG. 5, Formula 4) (SEQ ID NO:5) and the cDNA of the abnA gene starts at position 1163 (FIG. 19, Formula 22) (SEQ ID NO:23).

EXAMPLE 15.4

The Primary Structure of the abnA Gene

EXAMPLE 15.4.1

Sequence Analysis of the abnA Gene

The sequence of the A. niger abnA gene, its promoter-regulation region, the structural gene and the termination region, was determined by subcloning fragments from pIM950 into M13mp18/mp19, pGEM-7Zf(+) and pBluescript vectors, in combination with the use of specific oligonucleotides as primers in the sequencing reactions.

For nucleotide sequence analysis, restriction fragments were isolated as described in Example 13.2.4 and were then cloned in bacteriophage M13 mp18/19 RF DNA vectors (Messing (1983) supra; Norrander et al. (1983) supra), digested with the appropriate restriction enzymes. The nucleotide sequences were determined by the dideoxynucleotide chain-termination procedure (Sanger et al. (1977) supra) using the Pharmacia T7 DNA polymerase sequencing kit. Computer analysis was performed using the PC/GENE program. The nucleotide sequence determined is provided in FIG. 19 (Formula 22) (SEQ ID NO:23).

EXAMPLE 15.4.2

Characterization of the abnA Gene

The sequence comprising the abnA structural gene (FIG. 19, Formula 22) (SEQ ID NO:23) is preceded by a 1177 nucleotides long upstream region, having a putative TATA box at position 1106–1113.

The structural portion of the abnA gene ranges from position 1178 until position 2378 and contains three introns. The position of the introns is established by sequencing the cDNA fragment obtained in Example 4.3. These introns are found at positions 1445 until 1494, 1972 until 2030 and 2117 until 2167.

The abnA gene encodes a protein 346 amino acids in length, having a molecular weight of 37184 Da (FIG. 20, Formula 23) (SEQ ID NO:24) as derived from the abnA cDNA sequence. The N-terminal sequence, as determined in Example 12.3 (Formula 18) (SEQ ID NO:19) is preceded by a 19 amino acids long hydrophobic sequence. The amino acid sequence as determined from a CNBr peptide (Example 12.3, Formula 19) (SEQ ID NO:20) is found from position 106 until position 125 of the amino acid sequence. The mature protein is 327 amino acids in length and has a deduced molecular weight of 35204 Da and a theoretical IEP of 3.6.

EXAMPLE 16

Expression of the Cloned abnA Gene in A. niger and A. nidulans

EXAMPLE 16.1

Introduction of the abnA gene in A. niger N593 and A. nidulans WG191 by cotransformation The plasmid pIM950 was introduced into A. niger by cotransformation of A. niger N593 using the A. niger pyrA gene, located on the plasmid pGW613 (Goosen et al. (1989) supra), as a selective marker and the plasmid pIM950 as the cotransforming plasmid. Analogously, the gene was introduced in A. nidulans G191 using the above-mentioned plasmids. Transformation of both strains was performed as described in Example 14.1.

EXAMPLE 16.2

Screening of Transformants for the Expression of the abnA Gene

The transformants obtained in Example 16.1 were analyzed for the expression of the abnA gene product, the ABN A protein. Ten A. nidulans transformants and fourteen A. niger transformants were selected and grown on minimal medium containing 1% sugar beet pulp as a sole carbon source. After 24 hours of growth at 37° C. for A. nidulans and at 30° C. for A. niger, the mycelium was removed by filtration and the endo 1,5-α-L-arabinanase activity of culture filtrate was measured using ArabinaZyme tablets (Megazyme Pty. Ltd., North Rocks, New South Wales, Australia) according to the manufactors instructions. The results for both strains are summarized in Table 6 and Table 7.

TABLE 6

Endo 1,5-α-L-arabinanase activity in culture medium of Aspergillus nidulans wild type and abnA transformants at 24 hours of growth on sugar beet pulp as a carbon source.

| Strain | Activity (U/ml culture medium) |
|---|---|
| G191::pGW635 | 0.31 |
| G191::pIM950-1 | 0.83 |
| G191::pIM950-2 | 0.83 |
| G191::pIM950-6 | 0.79 |
| G191::pIM950-7 | 1.88 |
| G191::pIM950-11 | 1.17 |
| G191::pIM950-12 | 0.70 |
| G191::pIM950-16 | 0.70 |
| G191::pIM950-17 | 2.34 |
| G191::pIM950-18 | 1.18 |
| G191::pIM950-20 | 2.26 |

TABLE 7

Endo 1,5-α-L-arabinanase activity in culture medium of Aspergillus niger wild type and abnA transformants at 24 hours of growth on sugar beet pulp as a carbon source.

| Strain | Activity (U/ml culture medium) |
|---|---|
| N402 | 0.17 |
| N593::pIM950-1 | 0.91 |
| N593::pIM950-2 | 0.35 |
| N593::pIM950-3 | 0.25 |
| N593::pIM950-4 | 1.13 |
| N593::pIM950-5 | 1.23 |
| N593::pIM950-6 | 0.28 |
| N593::pIM950-7 | 1.13 |
| N593::pIM950-8 | 1.31 |
| N593::pIM950-9 | 1.09 |
| N593::pIM950-10 | 0.22 |
| N593::pIM950-11 | 1.23 |
| N593::pIM950-12 | 0.28 |
| N593::pIM950-13 | 0.32 |
| N593::pIM950-14 | 0.91 |

In addition, the culture filtrates were analyzed by Western blotting as described in Example 14.2. (FIG. 21 A and B—A. nidulans transformants; FIG. 22 A and B—A. niger transformants).

EXAMPLE 17

Characterization of the abfB Gene

The sequence comprising the abfB structural gene (FIG. 5, Formula 4) (SEQ ID NO:5), as found in the 2.8 kb SacI fragment (see Example 7), is preceded by a 166 nucleotide long upstream region. A putative TATA box extends from position 54 until position 60.

The structural portion of the abfB gene ranges from position 167 until position 1666 and contains no introns as is determined by sequencing the cDNA fragment obtained in Example 15.3.

The abfB gene encodes a protein 499 amino acids in length having a deduced molecular weight of 52523 Da (FIG. 6, Formula 5) ((SEQ ID NO:6) as derived from the abfB gene sequence and confirmed by the abfB cDNA sequence. The N-terminal amino acid sequence, as determined in Example 12.2 (Formula 14) (SEQ ID NO:15), is preceded by a 18 amino acid-long hydrophobic sequence. The amino acid sequences determined from the CNBr peptides (Formulas 15, 16 and 17) (SEQ ID NO:16, SEQ ID NO:17 and SEQ ID NO:18) are found in the sequence from amino acid position 203 until position 219, 267 until 286 and 294 until 312, respectively. The mature ABF B protein is 481 amino acids in length, and has a deduced molecular weight of 50663 Da and a theoretical IEP of 3.8. The deduced molecular weight value for the ABF B enzyme differs from those reported in the literature as mentioned above (see Rombouts et al., supra and van der Veen et al., supra). This is most likely to be attributable to the literature evaluations being made on the glycosylated protein whereas the deduced molecular weight found in the present example is based strictly on the unglycosylated protein.

EXAMPLE 18

ABF B Enzymatic Activity on Arabinoside-Containing Glucosidic Extracts Obtained from Grape A glycosidic extract was obtained by extraction of a must of Muscat de Frontignan variety grapes according to the method as described by Gunata et al. ((1989) supra).

The experimental protocol for the enzymatic hydrolysis on the glycosidic extract using the ABF B enzyme was as described by Gunata et al. ((1989) supra).

To 200 µl of the glycosidic extract, 50 µl (0.15 nkat, as determined according to the method described by Gunata et al. ((1989) supra) of a solution of α-arabinosidase (ABF B) was added and incubated for 16 hours at 40° C., pH 4.4. The solution was then extracted with 5×250 µl pentane. The hydrolysis was monitored via thin-layer and gas chromatography.

Afterwards, 50 µl (0.15 nkat, as determined according to the method described by Gunata (1989), supra) of a β-glucosidase solution was added to the solution. The thus-obtained solution was reincubated for 16 hours at 40° C., pH 4.4 and extracted with 5×250 µl pentane. The hydrolysis was monitored via thin-layer and gas chromatography.

The results obtained demonstrated that the ABF B enzyme was able to hydrolyze 70% of the arabinosyl glucoside from the glycosidic extract.

EXAMPLE 19

In-vitro Digestion of Sugar Beet Pulp with β-L-galactanase and/or α-L-arabinofuranosidase In a model system simulating the conditions found in the porcine stomach and small intestine, sugar beet pulp was incubated with respectively α-L-arabinofuranosidase (ABF B), β-L-galactanase and a mixture of both enzymes.

The sugar beet pulp was first incubated for three hours at pH=3.0 and T=39° C. (porcine stomach conditions). Afterwards, the pulp was incubated for an additional three hours at pH=6.5 and T=39° C. (porcine small intestine conditions).

After the enzymatic incubation, the difference between the initial dry mass and the insolubles remaining after the enzymatic hydrolysis (the matter was dried for 24 hours at T=103° C.) was measured. This difference in dry matter was considered to be a relative measure of the in-vitro digestion of the sugar beet pulp. The results of the experiments are summarized in Table 8.

TABLE 8

Percentage of digestibility in terms of dry mass after enzymatic incubation of sugar beet pulp at pig stomach and small intestine conditions

|  | % of digestion |
|---|---|
| Blank | 15,9 |
| α-L-arabinofuranosidase (ABF B) | 15,8 |
| β-L-galactanase | 16,0 |
| α-L-arabinofuranosidase (ABF B) plus β-L-galactanase | 24,8 |

Similar results were obtained from wheat bran.

While the present invention has been described with reference to specific embodiments thereof, it should be understood by those skilled in the art that various changes may be made and equivalents may be substituted without parting from the true spirit and scope of the invention. In addition, many modifications may be made to adapt a particular situation, material, process, process step or steps to the object, spirit and scope of the invention. All such modifications are intended to be within the scope of the claims appended hereto.

---

We claim:

1. An isolated DNA molecule that comprises a nucleotide sequence that encodes an enzyme having arabinan-degrading activity which cleaves the (1→2)-α-L-arabinosidic linkage, the (1→3)-α-L-arabinosidic linkage, the (1→5)-α-L-arabinosidic linkage, or the (1→6) linkage between the terminal arabinofuranosyl unit and the intermediate glucosyl unit of monoterpenyl α-L-arabinofuranosyl glucosides, wherein said enzyme is encoded by, or is a modified form of the enzyme encoded by, the nucleotide sequence of SEQ ID NO:5, SEQ ID NO:21 or SEQ ID NO:23, wherein said modified form of said enzyme differs by one or more amino acids from that encoded by said SEQ ID NO:5, SEQ ID NO:21 or SEQ ID NO:23 and is encoded by a nucleotide sequence which hybridizes to the encoding nucleotide sequence of SEQ ID NO:5 or SEQ ID NO:21 or SEQ ID NO:23 under conditions of an overnight incubation at 35° C. in a solution of 6×SSC, 5×Denhardt's solution 0.5% SDS and 100 μg/ml denatured non-specific DNA, followed by two 10 minute washes at 35° C. in a solution of 6×SSC and 0.1% SDS.

2. The DNA molecule of claim 1 wherein said encoding nucleotide sequence hybridizes to the encoding nucleotide sequence of SEQ ID NO:5 or SEQ ID NO:21 or SEQ ID NO:23 under conditions of hybridization for 18 hours at 68° C. in the presence of 6×SSC, 0.5% SDS, 5×Denhardt's solution followed by two washes for 30 minutes at 68° C. in 2×SSC/0.1% SDS followed by two washes for 30 minutes at 68° C. and 0.2×SSC/0.1% SDS.

3. The isolated DNA molecule of claim 1 wherein said encoding nucleotide sequence encodes an enzyme which cleaves (1→2)-α-L-arabinosidic linkages and (1→3)-α-L-arabinosidic linkages and wherein said encoding nucleotide sequence hybridizes to the encoding nucleotide sequence of SEQ ID NO:5 under conditions of an overnight incubation at 35° C. in a solution of 6×SSC, 5×Denhardt's solution, 0.5% SDS and 100 μg/ml denatured non-specific DNA, followed by two 10 minute washes at 35° C. in a solution of 6×SSC and 0.1% SDS.

4. The DNA molecule of claim 1, wherein said enzyme has exo-type arabinan-degrading activity on (1→3)-α-L-arabinosidic linkages and (1→2)-α-L-arabinosidic linkages.

5. The isolated DNA molecule of claim 1 wherein the nucleotide sequence encoding said enzyme having arabinan-degrading activity has the encoding nucleotide sequence of SEQ ID NO:5 or its genetic variants.

6. The isolated DNA molecule of claim 1 which is isocoding for the amino acid sequence of SEQ ID NO:6.

7. The isolated DNA molecule of claim 1 wherein said encoding nucleotide sequence encodes an enzyme which cleaves (1→5)-α-L-arabinosidic linkages and wherein said encoding nucleotide sequence hybridizes to the encoding nucleotide sequence of SEQ ID NO:21 under conditions of an overnight incubation at 35° C. in a solution of 6×SSC, 5×Denhardt's solution, 0.5% SDS and 100 μg/ml denatured non-specific DNA, followed by two 10 minute washes at 35° C. in a solution of 6×SSC and 0.1% SDS.

8. The DNA molecule of claim 1, wherein said enzyme has endo-type arabinan-degrading activity on (1→5)-α-L-arabinosidic linkages.

9. The isolated DNA molecule of claim 1 wherein the nucleotide sequence encoding said enzyme having arabinan-degrading activity has the encoding nucleotide sequence of SEQ ID NO:21 or its genetic variants.

10. The isolated DNA molecule of claim 1 which is isocoding for the amino acid sequence of SEQ ID NO:22.

11. The isolated DNA molecule of claim 1 wherein said encoding nucleotide sequence encodes an enzyme which cleaves (1×5)-α-L-arabinosidic linkages and wherein said encoding nucleotide sequence hybridizes to the encoding nucleotide sequence of SEQ ID NO:23 under conditions of an overnight incubation at 35° C. in a solution of 6×SSC, 5×Denhardt's solution 0.5% SDS and 100 μg/ml denatured non-specific DNA, followed by two 10 minute washes at 35° C. in a solution of 6×SSC and 0.1% SDS.

12. The DNA molecule of claim 1, wherein said enzyme has exo-type arabinan-degrading activity on (1→5)-α-L-arabinosidic linkages.

13. The isolated DNA molecule of claim 1 wherein the nucleotide sequence encoding said enzyme having arabinan-degrading activity has the encoding nucleotide sequence of SEQ ID NO:23 or its genetic variants.

14. The isolated DNA molecule of claim 1 which is isocoding for the amino acid sequence of SEQ ID NO:24.

15. The DNA molecule of claim 1, wherein said enzyme is an Aspergillus enzyme.

16. The DNA molecule of claim 15, wherein said Aspergillus is selected from the group consisting of *Aspergillus niger*, *Aspergillus niger* var. *tubigensis*, *Aspergillus niger* var. *awamori*, and *Aspergillus aculeatis*.

17. A DNA molecule comprising an expression system for the production of an enzyme having arabinan activity wherein the encoding nucleotide sequence of any of claims 1–3, 5–7, 9–11, 13 or 14 is recombinantly ligated to regulatory regions which direct expression of said encoding sequence in an appropriate host.

18. The DNA molecule of claim 17 wherein said regulatory regions comprise a promoter selected from the group of regulatory regions in native association with the coding regions of fungal endo-α-L-arabinanase (abnA) gene; fungal-α-L-arabinofuranosidase A (abfA) gene; fungal-α-L-arabinofuranosidase B (abfB) gene; fungal xylanase (xlnA) gene; fungal phytase gene; fungal ATP-synthetase synthetase gene; fungal subunit 9 (oliC) gene; fungal triose phosphate isomerase (tpi) gene; fungal alcohol dehydrogenase (adhA) gene; fungal α-amylase (amy) gene; fungal amyloglucosidase (glaA) gene; fungal acetamidase (amdS) gene; fungal glyceraldehyde-3-phosphate dehydrogenase (gpd) gene; yeast alcohol dehydrogenase gene; yeast lactase gene; yeast 3-phosphoglycerate kinase gene; yeast triose-phosphate isomerase gene; bacterial α-amylase gene; bacterial Spo2 gene; and bacterial extracellular protease genes.

19. The DNA molecule of claim 17 wherein the regulatory regions include a secretion leader sequence obtainable from a gene selected from the group of regulatory regions in native association with the coding regions of fungal amyloglucosidase (glaA) gene 18 amino acid AG leader; fungal amyloglucosidase (glaA) gene 24 amino acid AG leader; yeast α-factor gene; and bacterial α-amylase gene.

20. A vector which comprises the encoding nucleotide sequence of claim 1.

21. The vector of claim 20 which is a plasmid.

22. The DNA molecule of claim 4, wherein the encoding nucleotide sequence is comprised within the plasmid pGBabfB1 (CBS 156.91).

23. The DNA molecule of claim 8, wherein the encoding nucleotide sequence is comprised within the plasmid pIM950 (CBS 188.92).

24. The DNA molecule of claim 12, wherein the encoding nucleotide sequence is comprised within the plasmid pIM900 (CBS 187.92).

25. The vector of claim 21, wherein the plasmid is selected from pAGabfB3, pAGabfB4, pAGabfB5, pIM900-1, pIM900-2, pIM900-3, pIM900-4, pIM950-1, pIM950-2, pIM950-3, pIM950-4, pIM950-5, pIM950-6, pIM950-7, pIM950-8, pIM950-9, pIM950-10, pIM950-11, pIM950-12, pIM950-13, pIM950-14, pIM950-16, pIM950-17, pIM950-18 and pIM950-20.

26. A transformed microbial host comprising the DNA molecule of claim 17 permitting expression of an enzyme having arabinan-degrading activity.

27. A transformed microbial host according to claim 26, wherein the microbial host is selected from the genera consisting of Aspergillus, Kluyveromyces, Trichoderma, Saccharomyces and Bacillus.

28. A transformed microbial host according to claim 27, wherein the microbial host is selected from the species consisting of *Aspergillus niger, Aspergillus niger* var. *awamori, Aspergillus niger* var. *tubigensis, Aspergillus aculeatus, Aspergillus oryzae, Trichoderma reesei, Bacillus subtilis, Bacillus licheniformis, Kluyveromyces lactis* and *Saccharomyces cerevisiae*.

29. A transformed microbial host which produces an enzyme having arabinan-degrading activity, wherein said microbial host comprises a DNA molecule which comprises an expression system for the encoding nucleotide sequence of claim 12.

30. A transformed microbial host which produces an enzyme having arabinan-degrading activity, wherein said microbial host comprises a DNA molecule which comprises an expression system for the encoding nucleotide sequence of claim 4.

31. A transformed microbial host which produces an enzyme having arabinan-degrading activity, wherein said microbial host comprises a DNA molecule which comprises an expression system for the encoding nucleotide sequence of claim 8.

32. A method for expression of an enzyme having arabinan-degrading activity, comprising:
a) culturing the microbial host of claim 26 under conditions wherein said nucleotide sequence encoding said enzyme is expressed.

33. An enzyme having arabinan-degrading activity which is produced by culturing the microbial host of claim 30 under conditions wherein said enzyme is produced.

34. An enzyme having arabinan-degrading activity which is produced by culturing the microbial host of claim 31 under conditions wherein said enzyme is produced.

35. An enzyme having arabinan-degrading activity which is produced by culturing the microbial host of claim 29 under conditions wherein said enzyme is produced.

36. A method to degrade an arabinan-containing substrate, which method comprises contacting said substrate with the enzyme of claim 33.

37. The method of claim 36 wherein said substrate is a fruit or vegetable juice containing arabinan haze and said contacting is with an amount of enzyme effective in eliminating said haze.

38. The method of claim 36 wherein said substrate is a fruit or vegetable juice containing arabinogalactans and wherein said contacting is with an amount of enzyme effective to degrade said arabinogalactans, and wherein said contacting is followed by treating the fruit or vegetable juice with a galactanase enzyme in an amount sufficient to degrade galactan polymers so as to decrease the viscosity of said fruit or vegetable juice.

39. The method of claim 36 wherein said substrate is fruit or vegetable juice which contains monoterpenyl α-L-arabinofuranosyl glucosides and wherein said contacting is with an amount of enzyme sufficient to catalyze the release of arabinose residues from said glucosides and
which method further includes treating said fruit or vegetable juice with a β-glucosidase enzyme in an amount sufficient to release the terpenyl aroma components from desarabinosylated monoterpenyl glucosides.

40. The method of claim 36 wherein said substrate is a feed composition for an animal and wherein said contacting is with an amount of enzyme sufficient to improve in vivo uptake and utilization of said feed composition by the animal.

41. The method of claim 36 wherein said substrate is an arabinan-containing hemicellulose backbone of wood, wood pulp or wood derivative product and wherein said contacting is with an amount of enzyme sufficient to improve removal of lignins and terpenoids.

42. A method to degrade an arabinan-containing substrate, which method comprises contacting said substrate with the enzyme of claim 34.

43. The method of claim 42 wherein said substrate is a fruit or vegetable juice containing arabinan haze and said contacting is with an amount of enzyme effective in eliminating said haze.

44. The method of claim 42 wherein said substrate is a fruit or vegetable juice containing arabinogalactans and wherein said contacting is with an amount of enzyme effective to degrade said arabinogalactans, and wherein said contacting is followed by treating the fruit or vegetable juice with a galactanase enzyme in an amount sufficient to degrade galactan polymers so as to decrease the viscosity of said fruit or vegetable juice.

45. The method of claim 42 wherein said substrate is fruit or vegetable juice which contains monoterpenyl α-L-arabinofuranosyl glucosides and wherein said contacting is with an amount of enzyme sufficient to catalyze the release of arabinose residues from said glucosides and
which method further includes treating said fruit or vegetable juice with a β-glucosidase enzyme in an amount sufficient to release the terpenyl aroma components from desarabinosylated monoterpenyl glucosides.

46. The method of claim 42 wherein said substrate is a feed composition for an animal and wherein said contacting is with an amount of enzyme sufficient to improve in vivo uptake and utilization of said feed composition by the animal.

47. The method of claim 42 wherein said substrate is an arabinan-containing hemicellulose backbone of wood, wood pulp or wood derivative product and wherein said contacting is with an amount of enzyme sufficient to improve removal of lignins and terpenoids.

48. A method to degrade an arabinan-containing substrate, which method comprises contacting said substrate with the enzyme of claim 35.

49. The method of claim 48 wherein said substrate is a fruit or vegetable juice containing arabinan haze and said contacting is with an amount of enzyme effective in eliminating said haze.

50. The method of claim 48 wherein said substrate is a fruit or vegetable juice containing arabinogalactans and wherein said contacting is with an amount of enzyme effective to degrade said arabinogalactans, and wherein said contacting is followed by treating the fruit or vegetable juice with a galactanase enzyme in an amount sufficient to degrade galactan polymers so as to decrease the viscosity of said fruit or vegetable juice.

51. The method of claim 48 wherein said substrate is fruit or vegetable juice which contains monoterpenyl $\alpha$-L-arabinofuranosyl glucosides and wherein said contacting is with an amount of enzyme sufficient to catalyze the release of arabinose residues from said glucosides and which method further includes treating said fruit or vegetable juice with a $\beta$-glucosidase enzyme in an amount sufficient to release the terpenyl aroma components from desarabinosylated monoterpenyl glucosides.

52. The method of claim 48 wherein said substrate is a feed composition for an animal and wherein said contacting is with an amount of enzyme sufficient to improve in vivo uptake and utilization of said feed composition by the animal.

53. The method of claim 48 wherein said substrate is an arabinan-containing hemicellulose backbone of wood, wood pulp or wood derivative product and wherein said contacting is with an amount of enzyme sufficient to improve removal of lignins and terpenoids.

\* \* \* \* \*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 16 amino acids (B) TYPE: amino acid
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Aspergillus niger (xi) SEQUENCE DESCRIPTION: SEQ ID NO:1: FORMULAS 1 AND 2:

Gly Pro Xaa Asp Ile Tyr Glu Ala Gly Asp Thr Pro Xaa Val Ala
 1           5                   10                      15

Ala
16

(2) INFORMATION FOR SEQ ID NO:2:

(i) SEQUENCE CHARACTERISTICS:
(A) LENGTH: 18 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Aspergillus niger (xi) SEQUENCE DESCRIPTION: SEQ ID NO:2: FORMULA 3:

Xaa Lys Glu Xaa Ala Ile Ile Leu Gly Ile Gly Gly Asp Xaa Xaa
 1           5                   10                      15

Asn Gly Ala
       18

(2) INFORMATION FOR SEQ ID NO:3:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (synthetic)

(iii) HYPOTHETICAL: NO (vi) ORIGINAL SOURCE:
(C) INDIVIDUAL ISOLATE: AB1719

(ix) FEATURE:
(A) NAME/KEY: misc_difference
(B) LOCATION: replace (1)
(D) OTHER INFORMATION: /note= "N indicates inosine."

(ix) FEATURE:
(A) NAME/KEY: misc_difference
(B) LOCATION: replace (7)
(D) OTHER INFORMATION: /note= "N indicates inosine."

(ix) FEATURE:
(A) NAME/KEY: misc_difference
(B) LOCATION: replace (10)
(D) OTHER INFORMATION: /note= "N indicates inosine."

(xi) SEQUENCE DESCRIPTION: SEQ ID NO:3: FORMULA 1A:

NGTRTCNCCN GCYTCRTARA TRTC                                    24

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2306

( i x ) FEATURE:
        ( A ) NAME/KEY: misc_difference
        ( B ) LOCATION: replace (3)
        ( D ) OTHER INFORMATION: /note= "N indicates inosine."

( i x ) FEATURE:
        ( A ) NAME/KEY: misc_difference
        ( B ) LOCATION: replace (6)
        ( D ) OTHER INFORMATION: /note= "N indicates inosine."

( i x ) FEATURE:
        ( A ) NAME/KEY: misc_difference
        ( B ) LOCATION: replace (12)
        ( D ) OTHER INFORMATION: /note= "N indicates inosine."

( i x ) FEATURE:
        ( A ) NAME/KEY: misc_difference
        ( B ) LOCATION: replace (15)
        ( D ) OTHER INFORMATION: /note= "N indicates inosine."

( x i ) SEQUENCE DESCRIPTION: SEQ ID NO:4: FORMULA 3A:

```
TCNCCNCCRA  TNCCNAGRAT  RAT                                              23
```

( 2 ) INFORMATION FOR SEQ ID NO:5:

( i ) SEQUENCE CHARACTERISTICS:
        ( A ) LENGTH: 2753 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Aspergillus niger ( i x ) FEATURE:
        ( A ) NAME/KEY: CDS
        ( B ) LOCATION: 161..1660
        ( C ) IDENTIFICATION METHOD: experimental
        ( D ) OTHER INFORMATION: /codon_start= 161
            / product= "alpha-L-arabinofuranosidase B"
            / evidence= EXPERIMENTAL
            / gene= "exoB"

( i x ) FEATURE:
        ( A ) NAME/KEY: sig_peptide
        ( B ) LOCATION: 161..214

( i x ) FEATURE:
        ( A ) NAME/KEY: mat_peptide
        ( B ) LOCATION: 215..1660

( x i ) SEQUENCE DESCRIPTION: SEQ ID NO:5: FORMULA 4:

```
GAGCTCGATC  TTGCATTTCA  TGCATAGGCA  CTGACTGCAG  TAAAGAATAT  AAATAAGCCT    60

CCCTTCGCAC  CCTAGTAGCA  TGATTTCTTT  CTCCAAGCGG  CCTATCTCAC  TGTCTCCTCT   120
```

| | | | | | | | | | | | | | | | | |
|---|---|---|---|---|---|---|---|---|---|---|---|---|---|---|---|---|
| CCTAGCCCAG | AACTTACTGA | GCAGGCAGTA | ATCCTCCACC | ATG Met -18 | | TTC Phe | TCC Ser | CGC Arg -15 | CGA Arg | | | | | | | 175 |
| AAC Asn | CTC Leu | GTC Val | GCC Ala -10 | CTA Leu | GGG Gly | CTG Leu | GCA Ala | GCC Ala -5 | ACC Thr | GTC Val | AGC Ser | GCC Ala | GGC Gly | CCC Pro 1 | TGT Cys | 223 |
| GAC Asp | ATC Ile 5 | TAC Tyr | GAA Glu | GCC Ala | GGC Gly | GAC Asp 10 | ACG Thr | CCC Pro | TGC Cys | GTA Val | GCC Ala 15 | GCG Ala | CAC His | AGC Ser | ACC Thr | 271 |
| ACC Thr 20 | CGC Arg | GCC Ala | CTA Leu | TAC Tyr | AGC Ser 25 | TCC Ser | TTC Phe | AGC Ser | GGC Gly | GCC Ala 30 | CTC Leu | TAC Tyr | CAG Gln | CTC Leu | CAA Gln 35 | 319 |
| CGT Arg | GGC Gly | TCC Ser | GAC Asp | GAC Asp 40 | ACC Thr | ACC Thr | ACC Thr | ACC Thr | ATC Ile 45 | TCC Ser | CCG Pro | CTC Leu | ACA Thr | GCC Ala | GGC Gly 50 | 367 |
| GGC Gly | GTC Val | GCC Ala | GAC Asp 55 | GCC Ala | TCC Ser | GCC Ala | CAA Gln | GAC Asp 60 | ACC Thr | TTC Phe | TGT Cys | GCC Ala | AAC Asn 65 | ACC Thr | ACC Thr | 415 |
| TGC Cys | TTG Leu | ATC Ile 70 | ACC Thr | ATC Ile | ATC Ile | TAC Tyr | GAC Asp 75 | CAA Gln | TCC Ser | GGC Gly | AAC Asn | GGC Gly 80 | AAC Asn | CAC His | CTG Leu | 463 |
| ACC Thr | CAA Gln 85 | GCA Ala | CCC Pro | CCG Pro | GGA Gly | GGC Gly 90 | TTC Phe | GAC Asp | GGC Gly | CCC Pro | GAC Asp 95 | GTC Val | GAC Asp | GGC Gly | TAC Tyr | 511 |
| GAC Asp 100 | AAC Asn | CTC Leu | GCC Ala | AGC Ser | GCC Ala 105 | ATC Ile | GGC Gly | GCC Ala | CCC Pro | GTC Val 110 | ACC Thr | CTC Leu | AAT Asn | GGC Gly | CAA Gln 115 | 559 |
| AAG Lys | GCC Ala | TAC Tyr | GGC Gly | GTG Val 120 | TTC Phe | ATG Met | TCC Ser | CCC Pro | GGC Gly 125 | ACG Thr | GGC Gly | TAC Tyr | CGT Arg | AAC Asn 130 | AAC Asn | 607 |
| GAA Glu | GCC Ala | ACC Thr | GGC Gly 135 | ACC Thr | GCC Ala | ACC Thr | GGC Gly | GAC Asp 140 | GAA Glu | CCC Pro | GAA Glu | GGC Gly | ATG Met 145 | TAC Tyr | GCC Ala | 655 |
| GTC Val | CTG Leu | GAC Asp 150 | GGC Gly | ACG Thr | CAC His | TAC Tyr | AAC Asn 155 | GAC Asp | GCC Ala | TGC Cys | TGC Cys | TTC Phe 160 | GAC Asp | TAC Tyr | GGC Gly | 703 |
| AAC Asn | GCC Ala | GAG Glu 165 | ACC Thr | AGC Ser | AGC Ser | ACC Thr | GAC Asp 170 | ACT Thr | GGC Gly | GCC Ala | GGC Gly | CAC His 175 | ATG Met | GAG Glu | GCC Ala | 751 |
| ATC Ile 180 | TAC Tyr | CTC Leu | GGG Gly | AAC Asn | AGC Ser 185 | ACC Thr | ACC Thr | TGG Trp | GGC Gly | TAC Tyr 190 | GGC Gly | GCC Ala | GGT Gly | GAC Asp | GGG Gly 195 | 799 |
| CCC Pro | TGG Trp | ATC Ile | ATG Met | GTC Val 200 | GAT Asp | ATG Met | GAG Glu | AAC Asn | AAC Asn 205 | CTC Leu | TTC Phe | TCC Ser | GGT Gly | GCT Ala 210 | GAT Asp | 847 |
| GAG Glu | GGA Gly | TAT Tyr | AAC Asn 215 | TCC Ser | GGA Gly | GAT Asp | CCC Pro | TCG Ser 220 | ATC Ile | AGC Ser | TAC Tyr | AGC Ser | TTT Phe 225 | GTC Val | ACT Thr | 895 |
| GCC Ala | GCG Ala | GTC Val 230 | AAG Lys | GGG Gly | GGC Gly | GCT Ala | GAT Asp 235 | AAG Lys | TGG Trp | GCT Ala | ATT Ile | CGC Arg 240 | GGT Gly | GGT Gly | AAT Asn | 943 |
| GCT Ala | GCC Ala 245 | TCT Ser | GGG Gly | TCC Ser | CTC Leu | TCT Ser 250 | ACT Thr | TAC Tyr | TAC Tyr | AGC Ser | GGC Gly 255 | GCT Ala | CGC Arg | CCG Pro | GAT Asp | 991 |
| TAC Tyr 260 | TCC Ser | GGC Gly | TAT Tyr | AAC Asn | CCC Pro 265 | ATG Met | AGC Ser | AAG Lys | GAG Glu | GGC Gly 270 | GCT Ala | ATC Ile | ATC Ile | CTG Leu | GGT Gly 275 | 1039 |
| ATC Ile | GGC Gly | GGT Gly | GAC Asp | AAC Asn 280 | AGC Ser | AAC Asn | GGC Gly | GCC Ala | CAG Gln 285 | GGT Gly | ACC Thr | TTC Phe | TAC Tyr | GAG Glu 290 | GGT Gly | 1087 |

```
GTC ATG ACC TCC GGC TAC CCG TCG GAC GAT GTC GAG AAC TCC GTC CAG    1135
Val Met Thr Ser Gly Tyr Pro Ser Asp Asp Val Glu Asn Ser Val Gln
        295                     300                 305

GAG AAC ATC GTG GCT GCG AAA TAC GTC TCC GGC TCG CTG GTC AGC GGC    1183
Glu Asn Ile Val Ala Ala Lys Tyr Val Ser Gly Ser Leu Val Ser Gly
            310                 315                 320

CCG TCG TTC ACC TCC GGA GAG GTG GTC TCG CTG CGT GTC ACT ACC CCC    1231
Pro Ser Phe Thr Ser Gly Glu Val Val Ser Leu Arg Val Thr Thr Pro
        325                 330                 335

GGT TAC ACG ACG CGG TAT ATT GCG CAC ACT GAC ACC ACT GTG AAC ACG    1279
Gly Tyr Thr Thr Arg Tyr Ile Ala His Thr Asp Thr Thr Val Asn Thr
340                 345                 350                 355

CAG GTC GTG GAC GAC GAT AGT TCC ACC ACG CTG AAG GAG GAG GCT AGC    1327
Gln Val Val Asp Asp Asp Ser Ser Thr Thr Leu Lys Glu Glu Ala Ser
                    360                 365                 370

TGG ACC GTG GTG ACA GGT CTG GCT AAT AGT CAG TGC TTC TCG TTC GAG    1375
Trp Thr Val Val Thr Gly Leu Ala Asn Ser Gln Cys Phe Ser Phe Glu
                375                 380                 385

TCG GTT GAT ACC CCT GGT AGC TAT ATC CGG CAT TAC AAC TTT GAG TTG    1423
Ser Val Asp Thr Pro Gly Ser Tyr Ile Arg His Tyr Asn Phe Glu Leu
        390                 395                 400

CTG CTT AAT GCC AAC GAT GGC ACG AAG CAG TTC CAT GAG GAT GCT ACT    1471
Leu Leu Asn Ala Asn Asp Gly Thr Lys Gln Phe His Glu Asp Ala Thr
405                 410                 415

TTC TGT CCT CAG GCG CCG TTG AAT GGA GAA GGT ACT TCG TTG AGA TCG    1519
Phe Cys Pro Gln Ala Pro Leu Asn Gly Glu Gly Thr Ser Leu Arg Ser
420                 425                 430                 435

TGG AGT TAT CCG ACG AGG TAT TTC AGG CAT TAT GAG AAT GTC CTG TAT    1567
Trp Ser Tyr Pro Thr Arg Tyr Phe Arg His Tyr Glu Asn Val Leu Tyr
                440                 445                 450

GCT GCT AGT AAT GGT GGT GTG CAG ACG TTT GAT TCC AAG ACG TCG TTT    1615
Ala Ala Ser Asn Gly Gly Val Gln Thr Phe Asp Ser Lys Thr Ser Phe
            455                 460                 465

AAT AAT GAT GTT AGC TTT GAG ATT GAG ACG GCG TTT GCT TCG TAAGGGGGA  1667
Asn Asn Asp Val Ser Phe Glu Ile Glu Thr Ala Phe Ala Ser
            470                 475                 480

ATTGGGGGTT GTTTGGTGGT TTGGGTGTGG GGTTGTATCT GCCTGTGTTG GCGGGGAGAG  1727

TGGTTTGTAA ATAGGTCATT TTTGGTATAT AGCATACGAA TACTATACGA TAGTATACAT  1787

GATAGTGGTT GTTTCATGTA ATCGAGAAAT TATTCAAGGC TTGCAATACA ATATCTTATT  1847

ACTGTATCTC GTGGAGCATT CACAGACTGA ACGGCTGCAC AATGATTCTT ATGCGGTGAT  1907

ATTGACTGTG ATTAGATGAT ATATTCAGGT GTGCTATTTT TCTTGTATTT ATGCTTCATG  1967

CGAATATATG TATTTCACGA CAGACAGAGA GGTTAAACAA AGCATACTAA CGAGCGATTC  2027

AGATATGGCA TGTATGAATA AGACAAAAGT ACTGCGACAC TCAAGACCAA CACAAACCAG  2087

TATACTTCAT AACAATATAT GCTAGGCAGT ACCTCCGATT CTACGATGAG CTTTACCAGA  2147

AAATGGATTT CTTTGTCCCT CGTCATTCTC AATTTTGGG CCTTCCACGG CTGCGGCAAC    2207

CTGTTGAGCA AGACGTGTTC TCTCGTACGG ATGGACGTTG ATCTTCTTCT CGAGCAGGTC  2267

CAATTGCTCT TTCTCCAAAT GGCGGACTCT GACCTCACCG GAGGAATCAC TCGGCAAGCA  2327

TATCTGGTAA GTCGCTGAAA ATTTCTTCTC GAAACTGGCG TAGCTTGGTG CCACTGCGG   2387

GAAGCGTCGG AAGTATTTGC CTGTCCAGAC GGTCAATATG AATGAGTCGG ATACTTCAAT  2447

GCCCGCCTGC CTTCTACGGT CGAAGAAATG CTGGCCGATG CTTCTCACGG AGGCATAGTT  2507

TATAACAGGC TTGATGGGGT TTTGTATGTC GAGGAGACCT AATTCAAAGT GCATAGATAG  2567

GCTCCTGAGA TTGTGAAAAC CGGTTGCTAG TTTGTCGAAG ACGTCGTTGG GCTGTTGTGT  2627
```

```
GGTTATAGTT  CAGTTCATGG  GATGTACTAA  GAGGATTCTT  TGGCTTACCC  ATTGATCGTT      2687

CTCTCTCTTG  ACTCCCACCT  GCAGTGACTT  CAGTTTGGGA  CAGCTAACAT  CGAGGTGGCT      2747

GAGCTC                                                                      2753
```

( 2 ) INFORMATION FOR SEQ ID NO:6:

( i ) SEQUENCE CHARACTERISTICS:
    ( A ) LENGTH: 499 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6: FORMULA 5:

```
Met   Phe   Ser   Arg   Arg   Asn   Leu   Val   Ala   Leu   Gly   Leu   Ala   Ala   Thr   Val
-18               -15                     -10                           -5

Ser   Ala   Gly   Pro   Cys   Asp   Ile   Tyr   Glu   Ala   Gly   Asp   Thr   Pro   Cys   Val
                  1                 5                             10

Ala   Ala   His   Ser   Thr   Thr   Arg   Ala   Leu   Tyr   Ser   Ser   Phe   Ser   Gly   Ala
15                      20                            25                              30

Leu   Tyr   Gln   Leu   Gln   Arg   Gly   Ser   Asp   Thr   Thr   Thr   Thr   Ile   Ser
                  35                            40                              45

Pro   Leu   Thr   Ala   Gly   Gly   Val   Ala   Asp   Ala   Ser   Ala   Gln   Asp   Thr   Phe
                  50                            55                              60

Cys   Ala   Asn   Thr   Thr   Cys   Leu   Ile   Thr   Ile   Ile   Tyr   Asp   Gln   Ser   Gly
            65                            70                              75

Asn   Gly   Asn   His   Leu   Thr   Gln   Ala   Pro   Pro   Gly   Gly   Phe   Asp   Gly   Pro
      80                            85                            90

Asp   Val   Asp   Gly   Tyr   Asp   Asn   Leu   Ala   Ser   Ala   Ile   Gly   Ala   Pro   Val
95                            100                           105                         110

Thr   Leu   Asn   Gly   Gln   Lys   Ala   Tyr   Gly   Val   Phe   Met   Ser   Pro   Gly   Thr
                        115                           120                           125

Gly   Tyr   Arg   Asn   Asn   Glu   Ala   Thr   Gly   Thr   Ala   Thr   Gly   Asp   Glu   Pro
                  130                           135                           140

Glu   Gly   Met   Tyr   Ala   Val   Leu   Asp   Gly   Thr   His   Tyr   Asn   Asp   Ala   Cys
            145                           150                           155

Cys   Phe   Asp   Tyr   Gly   Asn   Ala   Glu   Thr   Ser   Ser   Thr   Asp   Thr   Gly   Ala
      160                           165                           170

Gly   His   Met   Glu   Ala   Ile   Tyr   Leu   Gly   Asn   Ser   Thr   Thr   Trp   Gly   Tyr
175                           180                           185                         190

Gly   Ala   Gly   Asp   Gly   Pro   Trp   Ile   Met   Val   Asp   Met   Glu   Asn   Asn   Leu
                        195                           200                           205

Phe   Ser   Gly   Ala   Asp   Glu   Gly   Tyr   Asn   Ser   Gly   Asp   Pro   Ser   Ile   Ser
                  210                           215                           220

Tyr   Ser   Phe   Val   Thr   Ala   Ala   Val   Lys   Gly   Gly   Ala   Asp   Lys   Trp   Ala
            225                           230                           235

Ile   Arg   Gly   Gly   Asn   Ala   Ala   Ser   Gly   Ser   Leu   Ser   Thr   Tyr   Tyr   Ser
      240                           245                           250

Gly   Ala   Arg   Pro   Asp   Tyr   Ser   Gly   Tyr   Asn   Pro   Met   Ser   Lys   Glu   Gly
255                           260                           265                         270

Ala   Ile   Ile   Leu   Gly   Ile   Gly   Gly   Asp   Asn   Ser   Asn   Gly   Ala   Gln   Gly
                        275                           280                           285

Thr   Phe   Tyr   Glu   Gly   Val   Met   Thr   Ser   Gly   Tyr   Pro   Ser   Asp   Asp   Val
                  290                           295                           300

Glu   Asn   Ser   Val   Gln   Glu   Asn   Ile   Val   Ala   Ala   Lys   Tyr   Val   Ser   Gly
```

|  |  |  |  |  | 305 |  |  |  |  | 310 |  |  |  |  | 315 |  |  |  |
|---|---|---|---|---|---|---|---|---|---|---|---|---|---|---|---|---|---|---|
| Ser | Leu | Val | Ser | Gly | Pro | Ser | Phe | Thr | Ser | Gly | Glu | Val | Val | Ser | Leu |
|  | 320 |  |  |  |  | 325 |  |  |  |  | 330 |  |  |  |  |
| Arg | Val | Thr | Thr | Pro | Gly | Tyr | Thr | Thr | Arg | Tyr | Ile | Ala | His | Thr | Asp |
| 335 |  |  |  |  | 340 |  |  |  |  | 345 |  |  |  |  | 350 |
| Thr | Thr | Val | Asn | Thr | Gln | Val | Val | Asp | Asp | Ser | Ser | Thr | Thr | Leu |
|  |  |  |  | 355 |  |  |  |  | 360 |  |  |  | 365 |  |
| Lys | Glu | Glu | Ala | Ser | Trp | Thr | Val | Val | Thr | Gly | Leu | Ala | Asn | Ser | Gln |
|  |  |  | 370 |  |  |  |  | 375 |  |  |  |  | 380 |  |  |
| Cys | Phe | Ser | Phe | Glu | Ser | Val | Asp | Thr | Pro | Gly | Ser | Tyr | Ile | Arg | His |
|  |  | 385 |  |  |  |  | 390 |  |  |  |  | 395 |  |  |  |
| Tyr | Asn | Phe | Glu | Leu | Leu | Leu | Asn | Ala | Asn | Asp | Gly | Thr | Lys | Gln | Phe |
|  | 400 |  |  |  |  | 405 |  |  |  |  | 410 |  |  |  |  |
| His | Glu | Asp | Ala | Thr | Phe | Cys | Pro | Gln | Ala | Pro | Leu | Asn | Gly | Glu | Gly |
| 415 |  |  |  |  | 420 |  |  |  |  | 425 |  |  |  |  | 430 |
| Thr | Ser | Leu | Arg | Ser | Trp | Ser | Tyr | Pro | Thr | Arg | Tyr | Phe | Arg | His | Tyr |
|  |  |  |  | 435 |  |  |  |  | 440 |  |  |  |  | 445 |  |
| Glu | Asn | Val | Leu | Tyr | Ala | Ala | Ser | Asn | Gly | Gly | Val | Gln | Thr | Phe | Asp |
|  |  |  | 450 |  |  |  |  | 455 |  |  |  |  | 460 |  |  |
| Ser | Lys | Thr | Ser | Phe | Asn | Asn | Asp | Val | Ser | Phe | Glu | Ile | Glu | Thr | Ala |
|  |  | 465 |  |  |  |  | 470 |  |  |  |  | 475 |  |  |  |
| Phe | Ala | Ser |
|  |  | 480 |

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( A ) ORGANISM: Aspergillus niger
        ( C ) INDIVIDUAL ISOLATE: AG-1

( x i ) SEQUENCE DESCRIPTION: SEQ ID NO:7: FORMULA 6:

GACAATGGCT ACACCAGCAC CGCAACGGAC ATTGTTTGGC CC      42

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( A ) ORGANISM: Aspergillus niger
        ( C ) INDIVIDUAL ISOLATE: AG-2

( x i ) SEQUENCE DESCRIPTION: SEQ ID NO:8: FORMULA 7:

AAGCAGCCAT TGCCCGAAGC CGAT      24

( 2 ) INFORMATION FOR SEQ ID NO:9:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  ( A ) ORGANISM: Aspergillus niger
  ( C ) INDIVIDUAL ISOLATE: 2796

( x i ) SEQUENCE DESCRIPTION: SEQ ID NO:9: FORMULA 8:

```
CTCTGCAGGA ATTCAAGCTA G                                              21
```

( 2 ) INFORMATION FOR SEQ ID NO:10:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  ( A ) ORGANISM: Aspergillus niger
  ( C ) INDIVIDUAL ISOLATE: 2628

( x i ) SEQUENCE DESCRIPTION: SEQ ID NO:10: FORMULA 9:

```
GTAGATGTCA CAGGGGCCTG CCAACCCTGT GCAGAC                              36
```

( 2 ) INFORMATION FOR SEQ ID NO:11:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  ( A ) ORGANISM: Aspergillus niger
  ( C ) INDIVIDUAL ISOLATE: 2629

( x i ) SEQUENCE DESCRIPTION: SEQ ID NO:11: FORMULA 10:

```
GTCTGCACAG GGTTGGCAGG CCCCTGTCAC ATCTAC                              36
```

( 2 ) INFORMATION FOR SEQ ID NO:12:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  ( A ) ORGANISM: Aspergillus niger
  ( C ) INDIVIDUAL ISOLATE: 2630

( x i ) SEQUENCE DESCRIPTION: SEQ ID NO:12: FORMULA 11:

```
GCTTAGCCCG GGGGTGCTTG GGTCAGG                                        27
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Aspergillus niger ( x i ) SEQUENCE DESCRIPTION: SEQ ID NO:13: FORMULA 12:

```
Xaa  Xaa  Leu  Lys  Val  Xaa  Thr  Gln  Gly  Gly
 1              5                        10
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Aspergillus niger ( x i ) SEQUENCE DESCRIPTION: SEQ ID NO:14: FORMULA 13:

```
Leu  Gln  Asn  Pro  Gly  Leu  Gln  Gly  Thr  Ala  Pro  Xaa  Leu  Thr  Ala
 1              5                        10                        15
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Aspergillus niger ( x i ) SEQUENCE DESCRIPTION: SEQ ID NO:15: FORMULA 14:

```
Xaa  Pro  Xaa  Asp  Ile  Tyr  Glu  Ala  Gly  Asp  Thr  Pro
 1              5                        10
```

( 2 ) INFORMATION FOR SEQ ID NO:16:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Aspergillus niger ( x i ) SEQUENCE DESCRIPTION: SEQ ID NO:16: FORMULA 15:

```
Glu Asn Asn Leu Phe Ser Gly Ala Asp Glu Gly Tyr Asn Ser Thr
 1               5                  10                  15

Asp Pro Thr
        18
```

( 2 ) INFORMATION FOR SEQ ID NO:17:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Aspergillus niger ( x i ) SEQUENCE DESCRIPTION: SEQ ID NO:17: FORMULA 16:

```
Ser Lys Glu Gly Ala Ile Ile Leu Gly Ile Gly Gly Asp Asn Ser
 1               5                  10                  15

Asn Gly Ala Gln Gly
                20
```

( 2 ) INFORMATION FOR SEQ ID NO:18:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Aspergillus niger ( x i ) SEQUENCE DESCRIPTION: SEQ ID NO:18: FORMULA 17:

```
Thr Ser Gly Tyr Pro Ser Asp Asp Val Glu Asn Ser Val Xaa Gln
 1               5                  10                  15

Ile Val Ala
        18
```

( 2 ) INFORMATION FOR SEQ ID NO:19:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Aspergillus niger ( x i ) SEQUENCE DESCRIPTION: SEQ ID NO:19: FORMULA 18:

```
Tyr Ala Asp Pro Gly Ala Xaa Ser Gly Val Xaa Thr Thr
 1           5                   10          13
```

( 2 ) INFORMATION FOR SEQ ID NO:20:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Aspergillus niger ( x i ) SEQUENCE DESCRIPTION: SEQ ID NO:20: FORMULA 19:

```
Glu Tyr Gly Ser Trp Thr Asp His Gly Ser Thr Gly Ile Ala Ser
 1           5                   10                      15

Arg Xaa Ala Lys Ile
             20
```

( 2 ) INFORMATION FOR SEQ ID NO:21:

( i ) SEQUENCE CHARACTERISTICS:
    ( A ) LENGTH: 3958 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Aspergillus niger ( i x ) FEATURE:
    ( A ) NAME/KEY: exon
    ( B ) LOCATION: 1247..1390

( i x ) FEATURE:
    ( A ) NAME/KEY: intron
    ( B ) LOCATION: 1391..1442

( i x ) FEATURE:
    ( A ) NAME/KEY: exon
    ( B ) LOCATION: 1443..1957

( i x ) FEATURE:
    ( A ) NAME/KEY: intron
    ( B ) LOCATION: 1958..2005

( i x ) FEATURE:
    ( A ) NAME/KEY: exon
    ( B ) LOCATION: 2006..2089

( i x ) FEATURE:
    ( A ) NAME/KEY: intron
    ( B ) LOCATION: 2090..2137

( i x ) FEATURE:

(A) NAME/KEY: exon
(B) LOCATION: 2138..2214

(ix) FEATURE:
(A) NAME/KEY: intron
(B) LOCATION: 2215..2262

(ix) FEATURE:
(A) NAME/KEY: exon
(B) LOCATION: 2263..2295

(ix) FEATURE:
(A) NAME/KEY: intron
(B) LOCATION: 2296..2346

(ix) FEATURE:
(A) NAME/KEY: exon
(B) LOCATION: 2347..2498

(ix) FEATURE:
(A) NAME/KEY: intron
(B) LOCATION: 2499..2548

(ix) FEATURE:
(A) NAME/KEY: exon
(B) LOCATION: 2549..3037

(ix) FEATURE:
(A) NAME/KEY: intron
(B) LOCATION: 3038..3092

(ix) FEATURE:
(A) NAME/KEY: exon
(B) LOCATION: 3093..3485

(ix) FEATURE:
(A) NAME/KEY: CDS
(B) LOCATION: join(1247..1390, 1443..1957, 2006..2089,
        2138..2214, 2263..2295, 2347..2498, 2549..3037,
        3093..3485)
(C) IDENTIFICATION METHOD: experimental
(D) OTHER INFORMATION: /codon_start= 1247
        / product= "alpha-L-arabinofuranosidase A"
        / evidence= EXPERIMENTAL
        / gene= "exoA"

(ix) FEATURE:
(A) NAME/KEY: sig_peptide
(B) LOCATION: 1247..1321

(ix) FEATURE:
(A) NAME/KEY: mat_peptide
(B) LOCATION: 1322..3485

(xi) SEQUENCE DESCRIPTION: SEQ ID NO:21: FORMULA 20:

```
AAGGGACTGA  CTGAACTCAG  TGAGATGTGC  CGCGAAGTAA  CTAAGCGCTG  TGCCTGCAGT   60
GAGGCGTGAT  GGAACACTGC  ATCCGATCTC  AAGACCCCG   ATATGAACCT  TAATGACAAT  120
GGTCTAAGTT  TTTTTGTCAT  CTCGCATAGC  ACGGTAGGCG  ACTAAGTTGA  AGGATAAAGA  180
GAGCAGGATT  AGGATGGCTC  GAGATCAAAT  TGAAAGTAAT  AGAGTAACAG  GGAAAACTC   240
TAACAGTTGG  CTATGACGAA  GGTGGCAGCG  ACTTCCCGGA  GAGAGATTAA  GCCGGGTAGA  300
ACCAAGGGAC  GGCTGTGGCT  GGATCAGGAA  CCCAAATCTA  TTCCAGTATC  GGAGGATACT  360
CAGGGGTCCC  GCCGGGGTTT  TCCCTTGATC  GGAGAACATC  AACCACATCA  AAATGCGGAG  420
TAACGATGAG  GGGGAAGTGC  ACGGCCGACG  TCAGAGTTTC  GCTTGGGTGG  ATCTGCAATG  480
TTTAGGCGGC  CGACTAGACC  GACAGTCCAG  CACCTGCCCT  GGGAGTTCAA  GACAGTGGTT  540
TGACCATCTT  TTGAGAAGAC  TGAAATTCCC  GTAGATTCCA  TCAAGATTAT  TCATGTATCA  600
CTAGCGACTC  AGCACTGGGT  AAGCTGCACC  CACGGATTTT  CTCAGCTATC  TGAATGTATC  660
AGAGACAAAG  ATCTTCGTGG  ATGGAGGCCA  TCAACCGAGC  TTTAATGCGC  CAAACCTACT  720
```

-continued

| | | | | | | |
|---|---|---|---|---|---|---|
| GTATGACTGA | ATAATGGATG | GATCGGCATG | TCGTACGATC | GGGTAAGGGT | CCTAAAAATG | 780 |
| GAGGGCCGGG | GAATTCTGGG | GTTAGCCGTC | GGGATTATTT | CGGTACGACA | AACTCACTGT | 840 |
| TCACTTTGAT | CTCGGCGTGG | TTGCGGCTAA | AAAGATGACC | TTGAAGGTGG | AGCGAACAAC | 900 |
| TGGAGGTGCT | CGGAGGGACG | CGGAGAAGAG | AGGATCCAAG | ACATCGGGGC | AGGGAAGTCC | 960 |
| ATGCCGCGTG | CAGTCACGCT | TTTCCTCCCT | CTGCTCTCTT | CTCCTCCACA | TTCCACATTC | 1020 |
| CACCTCCACA | CTCCTCCACT | CTTCCTCTGG | CACCTTCCTC | TTCCTCGATT | TCTTGGCTTC | 1080 |
| TCGGTTGATT | GTCTTCGACC | TCGTTGCGAT | GACCCCACCG | CATTTTCTGC | TGCCTTGGCC | 1140 |
| TGTCTGATGC | CCCGGTTAAT | TTCACGAAAG | TCCGGTCATA | AAAGGCGTTG | TATCCTCCCT | 1200 |
| TTGCAACAAT | GACACCAGGC | TCAGCTTCCT | CCAGACAGCC | GGCAACATGG | TGGCCTTTTC | 1260 |
| AGCTCTTTCG | GGCGTCAGCG | CCGTTTCTTT | ACTACTATCC | CTCGTTCAAA | ATGCACACGG | 1320 |
| AATCTCCTTG | AAGGTCTCCA | CCCAGGGTGG | CAACTCATCC | AGCCCATCC | TATATGGCTT | 1380 |
| CATGTTTGAG | GTAGGCCGCA | GACTAAGCAG | TAAAGACAA | TTGGTTCTCT | GACGGTGATT | 1440 |
| AGGATATCAA | TCACTCAGGA | GATGGAGGAA | TTTATGGGCA | AATGCTGCAG | AACCCTGGCC | 1500 |
| TTCAGGGAAC | GGCGCCTAAT | CTGACTGCCT | GGGCGGCTGT | CGGTGACGCT | ACCATCGCCA | 1560 |
| TTGATGGCGA | CAGTCCATTG | ACCTCTGCCA | TCCCAGCAC | CATCAAGCTT | AATATTGCGG | 1620 |
| ACGATGCTAC | CGGTGCGGTG | GGTCTCACCA | ATGAGGGATA | TTGGGGCATC | CCAGTCGATG | 1680 |
| GCAGCGAATT | CCATAGTTCC | TTCTGGATAA | AGGGAGATTA | CTCCGGCGAC | ATCACCGTCC | 1740 |
| GACTGGTTGG | AAACTACACC | GGCACGGAGT | ACGGCTCTAC | CACTATCACC | CATACGTCCA | 1800 |
| CAGCAGACAA | CTTCACCCAA | GCCTCCGTCA | AGTTCCCCAC | CACCAAGGCT | CCAGATGGCA | 1860 |
| ACGTTTTGTA | CGAGCTCACA | GTTGATGGAA | GCGTGGCTGC | TGGCTCGTCT | TTGAACTTCG | 1920 |
| GCTACTTGAC | GCTTTTTGGC | GAAACCTATA | AGTCAAGGTT | TGCTTCCCTA | TACTCCGAAG | 1980 |
| AGTGAATTAG | GGGCTAATTG | TGTAGGGAAA | ATGGCCTGAA | GCCCAGCTT | GCCAATGTGT | 2040 |
| TGGATGATAT | GAAAGGATCC | TTCCTGAGAT | TTCCCGGCGG | TAACAACCTG | TAAGTCTCAG | 2100 |
| CTCGCCCGGT | AAGTGTATAG | AAGCTCATCA | GAGGTAGTGA | GGGAAACAGC | GCAGAAAACC | 2160 |
| GCTGGAAGTG | GAACGAGACA | ATCGGCGATC | TTTGTGATCG | TCCCGGACGT | GAAGGTATGT | 2220 |
| CTCATTATTA | GGATTGAAGC | ATTCATCCCT | GACGGTATAT | AGGCACTTGG | ACTTACTATA | 2280 |
| ACACCGACGG | ACTGGGTAAG | TAAAGGGCTA | TATACAAGTA | CCTAGATACT | GTACTAACGC | 2340 |
| TTGTAGGCCT | TCACGAATAC | TTTTACTGGT | GTGAGGATTT | GGGGCTCGTA | CCGGTGCTCG | 2400 |
| GTGTCTGGGA | TGGGTTCGCT | CTGGAGTCGG | GTGGCAACAC | CCCCCTCACG | GGCGACGCAC | 2460 |
| TGACCCCTTA | TATCGACGAT | GTCTTGAACG | AGCTCGAGGT | ATGTTGAGCG | GCATATCAAA | 2520 |
| TTGATAGCTG | AAGCTAACCC | ATTGGCAGTA | CATCTTGGGT | GATACGAGCA | CGACCTATGG | 2580 |
| AGCGTGGCGC | GCGGCAAACG | GACAGGAGGA | GCCGTGGAAC | CTTACCATGG | TCGAGATTGG | 2640 |
| CAATGAGGAC | ATGCTGGGAG | GCGGATGCGA | GTCCTACGCG | GAACGTTTCA | CTGCCTTCTA | 2700 |
| TGATGCGATT | CATGCTGCTT | ATCCGGACCT | TATCCTGATT | GCCAGCACCA | GCGAGGCGGA | 2760 |
| TTGCTTGCCC | GAGTCAATGC | CCGAGGGTAG | CTGGGTCGAC | TACCACGACT | ACAGCACGCC | 2820 |
| TGATGGACTG | GTGGGCCAGT | TCAACTACTT | CGACAATTTA | AACCGCTCGG | TACCATACTT | 2880 |
| CATCGGCGAG | TACTCGCGCT | GGGAGATTGA | CTGGCCCAAC | ATGAAGGGAT | CGGTCGCTGA | 2940 |
| AGCCGTCTTC | ATGATCGGGT | TCGAGAGGAA | CAGCGACGTG | GTGAAGATGG | CGGCGTATGC | 3000 |
| GCCTTTGCTC | CAGCTAATCA | ACTCGACTCA | GTGGACGGTA | AGTCACGACT | GAGCAGCGGG | 3060 |
| GTTTCAGGTA | TGAATGAGCT | AACGAGTGGT | AGCCGGACCT | GATCGGATAC | ACGCAGTCAC | 3120 |

-continued

| | | | | | |
|---|---|---|---|---|---|
| CCGGTGACAT | TTTCCTGTCG | ACCAGCTACT | ACGTGCAGGA | GATGTTCTCG | CGCAACCGGG | 3180 |
| GTGATACAAT | TAAGGAGGTG | ACGTCGGACA | GCGACTTCGG | ACCGTTGTAC | TGGGTTGCGT | 3240 |
| CGAGCGCCGG | GGACTCGTAC | TACGTGAAGC | TGGCCAACTA | TGGCTCCGAG | ACGCAAGACC | 3300 |
| TCACGGTGAG | CATCCCAGGA | ACGAGCACAG | GCAAGTTGAC | GGTGCTGGCG | GACAGTGATC | 3360 |
| CGGATGCGTA | TAACTCGGAC | ACCCAGACGC | TGGTCACGCC | GAGTGAATCG | ACGGTGCAGG | 3420 |
| CGAGCAATGG | CACTTTTACC | TTTAGTTTGC | CGGCATGGGC | GGTGGCTGTC | CTGGCGGCGA | 3480 |
| ACTAGCGTTG | ATTGGGGCGA | GCTCGTATGG | GCGGCAAGTC | GAATATTATC | TGCAGGTGTG | 3540 |
| GTGTCATGTA | CTGCAGTATT | TCTGATTAAC | GATAGAGAGA | TAGATCCATG | CTATATACCT | 3600 |
| GCTTGTATAT | CCAAGGCATT | TATCCAATGA | TAGGCAACGC | CACCACACGT | GGCTATGCAC | 3660 |
| ATACTAGTCA | GGAGGTAGTA | GAGTGACTGA | CTGCTATGTA | GCGGTCGGCC | GGGGATAGCA | 3720 |
| GTTGAATGAC | CCCAATTAAC | AGAACCGCCT | GACTCTCCAA | CGTGTACCTC | TAGGTTATTT | 3780 |
| TATATTTCTT | GTTAAAGCCC | CCCAGAAACA | CAACCGAAGA | ATCAATGGAT | GCGATGAAAA | 3840 |
| CAAGGCACTG | GTAAGCGAAG | GAGGGAAAAA | CAAGCGGATT | GGTTGGTTGT | GGCCCGATGC | 3900 |
| AAACGGGCGG | CCTCTCCACT | CGAATTGGAC | AGAAGCGAAG | GCCGTGCGCC | GAGACGGG | 3958 |

( 2 ) INFORMATION FOR SEQ ID NO:22:

( i ) SEQUENCE CHARACTERISTICS:
        ( A ) LENGTH: 628 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22: FORMULA 21:

```
Met  Val  Ala  Phe  Ser  Ala  Leu  Ser  Gly  Val  Ser  Ala  Val  Ser  Leu  Leu
-24            -20                      -15                      -10

Leu  Ser  Leu  Val  Gln  Asn  Ala  His  Gly  Ile  Ser  Leu  Lys  Val  Ser  Thr
               -5                  -1   +1                 5

Gln  Gly  Gly  Asn  Ser  Ser  Ser  Pro  Ile  Leu  Tyr  Gly  Phe  Met  Phe  Glu
          10                 15                      20

Asp  Ile  Asn  His  Ser  Gly  Asp  Gly  Ile  Tyr  Gly  Gln  Met  Leu  Gln
 25                      30                      35                      40

Asn  Pro  Gly  Leu  Gln  Gly  Thr  Ala  Pro  Asn  Leu  Thr  Ala  Trp  Ala  Ala
               45                       50                       55

Val  Gly  Asp  Ala  Thr  Ile  Ala  Ile  Asp  Gly  Asp  Ser  Pro  Leu  Thr  Ser
               60                       65                       70

Ala  Ile  Pro  Ser  Thr  Ile  Lys  Leu  Asn  Ile  Ala  Asp  Asp  Ala  Thr  Gly
               75                       80                       85

Ala  Val  Gly  Leu  Thr  Asn  Glu  Gly  Tyr  Trp  Gly  Ile  Pro  Val  Asp  Gly
          90                 95                      100

Ser  Glu  Phe  His  Ser  Ser  Phe  Trp  Ile  Lys  Gly  Asp  Tyr  Ser  Gly  Asp
105                     110                     115                     120

Ile  Thr  Val  Arg  Leu  Val  Gly  Asn  Tyr  Thr  Gly  Thr  Glu  Tyr  Gly  Ser
               125                     130                     135

Thr  Thr  Ile  Thr  His  Thr  Ser  Thr  Ala  Asp  Asn  Phe  Thr  Gln  Ala  Ser
               140                     145                     150

Val  Lys  Phe  Pro  Thr  Thr  Lys  Ala  Pro  Asp  Gly  Asn  Val  Leu  Tyr  Glu
          155                     160                     165

Leu  Thr  Val  Asp  Gly  Ser  Val  Ala  Ala  Gly  Ser  Ser  Leu  Asn  Phe  Gly
     170                     175                     180

Tyr  Leu  Thr  Leu  Phe  Gly  Glu  Thr  Tyr  Lys  Ser  Arg  Glu  Asn  Gly  Leu
```

```
            185                     190                     195                     200
Lys  Pro  Gln  Leu  Ala  Asn  Val  Leu  Asp  Asp  Met  Lys  Gly  Ser  Phe  Leu
                    205                     210                     215
Arg  Phe  Pro  Gly  Gly  Asn  Asn  Leu  Glu  Gly  Asn  Ser  Ala  Glu  Asn  Arg
                    220                     225                     230
Trp  Lys  Trp  Asn  Glu  Thr  Ile  Gly  Asp  Leu  Cys  Asp  Arg  Pro  Gly  Arg
               235                     240                     245
Glu  Gly  Thr  Trp  Thr  Tyr  Tyr  Asn  Thr  Asp  Gly  Leu  Gly  Leu  His  Glu
          250                     255                     260
Tyr  Phe  Tyr  Trp  Cys  Glu  Asp  Leu  Gly  Leu  Val  Pro  Val  Leu  Gly  Val
265                     270                     275                     280
Trp  Asp  Gly  Phe  Ala  Leu  Glu  Ser  Gly  Gly  Asn  Thr  Pro  Leu  Thr  Gly
                    285                     290                     295
Asp  Ala  Leu  Thr  Pro  Tyr  Ile  Asp  Asp  Val  Leu  Asn  Glu  Leu  Glu  Tyr
               300                     305                     310
Ile  Leu  Gly  Asp  Thr  Ser  Thr  Thr  Tyr  Gly  Ala  Trp  Arg  Ala  Ala  Asn
               315                     320                     325
Gly  Gln  Glu  Glu  Pro  Trp  Asn  Leu  Thr  Met  Val  Glu  Ile  Gly  Asn  Glu
          330                     335                     340
Asp  Met  Leu  Gly  Gly  Gly  Cys  Glu  Ser  Tyr  Ala  Glu  Arg  Phe  Thr  Ala
345                     350                     355                     360
Phe  Tyr  Asp  Ala  Ile  His  Ala  Ala  Tyr  Pro  Asp  Leu  Ile  Leu  Ile  Ala
                    365                     370                     375
Ser  Thr  Ser  Glu  Ala  Asp  Cys  Leu  Pro  Glu  Ser  Met  Pro  Glu  Gly  Ser
               380                     385                     390
Trp  Val  Asp  Tyr  His  Asp  Tyr  Ser  Thr  Pro  Asp  Gly  Leu  Val  Gly  Gln
          395                     400                     405
Phe  Asn  Tyr  Phe  Asp  Asn  Leu  Asn  Arg  Ser  Val  Pro  Tyr  Phe  Ile  Gly
          410                     415                     420
Glu  Tyr  Ser  Arg  Trp  Glu  Ile  Asp  Trp  Pro  Asn  Met  Lys  Gly  Ser  Val
425                     430                     435                     440
Ala  Glu  Ala  Val  Phe  Met  Ile  Gly  Phe  Glu  Arg  Asn  Ser  Asp  Val  Val
                    445                     450                     455
Lys  Met  Ala  Ala  Tyr  Ala  Pro  Leu  Leu  Gln  Leu  Ile  Asn  Ser  Thr  Gln
               460                     465                     470
Trp  Thr  Pro  Asp  Leu  Ile  Gly  Tyr  Thr  Gln  Ser  Pro  Gly  Asp  Ile  Phe
          475                     480                     485
Leu  Ser  Thr  Ser  Tyr  Tyr  Val  Gln  Glu  Met  Phe  Ser  Arg  Asn  Arg  Gly
          490                     495                     500
Asp  Thr  Ile  Lys  Glu  Val  Thr  Ser  Asp  Ser  Asp  Phe  Gly  Pro  Leu  Tyr
505                     510                     515                     520
Trp  Val  Ala  Ser  Ser  Ala  Gly  Asp  Ser  Tyr  Tyr  Val  Lys  Leu  Ala  Asn
                    525                     530                     535
Tyr  Gly  Ser  Glu  Thr  Gln  Asp  Leu  Thr  Val  Ser  Ile  Pro  Gly  Thr  Ser
               540                     545                     550
Thr  Gly  Lys  Leu  Thr  Val  Leu  Ala  Asp  Ser  Asp  Pro  Asp  Ala  Tyr  Asn
          555                     560                     565
Ser  Asp  Thr  Gln  Thr  Leu  Val  Thr  Pro  Ser  Glu  Ser  Thr  Val  Gln  Ala
          570                     575                     580
Ser  Asn  Gly  Thr  Phe  Thr  Phe  Ser  Leu  Pro  Ala  Trp  Ala  Val  Ala  Val
585                     590                     595                     600
Leu  Ala  Ala  Asn
          604
```

(2) INFORMATION FOR SEQ ID NO:23:

(i) SEQUENCE CHARACTERISTICS:
        (A) LENGTH: 3147 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Aspergillus niger (ix) FEATURE:
        (A) NAME/KEY: exon
        (B) LOCATION: 1178..1444

(ix) FEATURE:
        (A) NAME/KEY: intron
        (B) LOCATION: 1445..1494

(ix) FEATURE:
        (A) NAME/KEY: exon
        (B) LOCATION: 1495..1971

(ix) FEATURE:
        (A) NAME/KEY: intron
        (B) LOCATION: 1972..2030

(ix) FEATURE:
        (A) NAME/KEY: exon
        (B) LOCATION: 2031..2116

(ix) FEATURE:
        (A) NAME/KEY: intron
        (B) LOCATION: 2117..2167

(ix) FEATURE:
        (A) NAME/KEY: exon
        (B) LOCATION: 2168..2378

(ix) FEATURE:
        (A) NAME/KEY: CDS
        (B) LOCATION: join(1178..1444, 1495..1971, 2031..2116,
            2168..2378)
        (C) IDENTIFICATION METHOD: experimental
        (D) OTHER INFORMATION: /codon_start= 1178
            / product= "endo 1,5-alpha-arabinanase"
            / evidence= EXPERIMENTAL
            / gene= "abnA"

(ix) FEATURE:
        (A) NAME/KEY: sig_peptide
        (B) LOCATION: 1178..1234

(ix) FEATURE:
        (A) NAME/KEY: mat_peptide
        (B) LOCATION: 1235..2378

(xi) SEQUENCE DESCRIPTION: SEQ ID NO:23: FORMULA 22:

```
AAGCTTGGTC  GTGTCCGCGG  TAGTACTACC  TCCGTAGAGA  CTCTCTCTGG  ATCTTCTCAA      60

AAGGGGGTTT  CGTGTTCTGG  TACAGACTCT  TCTAGTTCTC  GCTTACGGCT  CCACCCATTG     120

CTGAAGAACC  CCACTCCTGC  TGTTTCCCAT  TTATGTTCCG  GTCTAACGAT  GGCTTCTCCA     180

CCAAGAAATG  GAAGTGTGCT  CTCCTCTCAA  AACTCTCCAA  TTCTGGTTTG  ATCGATGTGA     240

GCTTACCAAG  AAAGAGCGAA  GACTTCCATC  TTGTACTTAC  GGACCCGATT  AGCTATGCTT     300

CCTACACGTT  NAANGACGAT  NGACATATNN  TGCTACCTGT  TACTTGTCAG  ATGGTCTCTC     360

TAACGCTGGC  GGNATGTGGA  CCAGATTCTC  TTCAAAGTTA  TGCCAAGATT  CGCATGGGCC     420
```

```
AATCCTGAAA  AGCGAAAAGC  GCAAGGAGGC  GCAGCTGAGA  CAGAATCCCC  TTTCTGCGAG    480

TCACATCTCG  AGTCCCTTAA  GGCCACCGTC  GAGTGGTGGG  CGATAAACTC  CGCATATCTG    540

CCACCTGAAA  AATATCGGTC  AATACATCTA  TGGCCTAATG  AGACCAGTGG  TCAGAATACG    600

CCTAAGGCCG  GAAACTACTC  CCGCAAATTG  CTGCGACGAA  GACGAGGGGG  GCGTAGTCAT    660

AAATTTGCGT  GTCGTGTGCC  TATGATAATT  TCTTGGGGTC  CGAAGAGCAC  GCTAGGGATG    720

TCAGAACAAC  TAATGTTGCA  GGATTGGTCT  CCATCTCATC  CCTGTCACTG  ACATCATATT    780

ACTTCCTAGT  ATATCATGTT  CACCATTGTA  TAGAGAGACG  CGCCCATCGC  AACGCACGTG    840

TTGGTGAGCA  CCTCCACTAA  AAGTGTCACT  GTTGTCTACA  CACCACTCGT  TTCACGCTGA    900

TGTGCCGAAT  CATACTACAT  GCATCGGCCA  TCGGCTTATA  CCACCAGGTG  CCTCCGGAAT    960

TTTGCTGTTT  CAAAATGTTC  TTTGTAACTC  CCTGAAACGA  CCAAAGTATC  ACGGAGGTAG   1020

CTCCGGACAG  GCGGAAAACA  CAACCACTTT  GTCCACGAAT  CGACACAGTA  GTCTTCCGGT   1080

GGGTTTAGTT  GTCGCTTCAT  GATAGTATAT  ATAGTAATAG  TAGATCTGGA  TGCTTGGGAT   1140

AAGTCATCCA  GTGGTGACAG  CGCCTACCTA  AATCGTCATG  TATCAACTCC  TATCAGTTGC   1200

CTCGGTTCCT  CTGCTGGCCA  GCCTCGTGCA  TGGCTATGCT  GACCCCGGAG  CATGCTCGGG   1260

TGTTTGTACC  ACCCATGACC  CCGGTTTGAT  CCGGAGAGAG  TCGGACGGTA  CATACTTCCT   1320

CTTCTCTACA  GGAAACAAAA  TCTCCTACGT  CTCTGCATCA  TCCATCGAAG  GACCATGGAC   1380

CAGCGTTGGG  TCTATGCTGC  CGGATGGATC  GTCCATCGAC  CTCGATGGCA  ACGATGATCT   1440

TTGGGTAACT  ATGTCCCACT  GCAAACATGA  TTGGCCTGTC  TGACACTAGC  CCAGGCCCCG   1500

GATGTCTCCT  ATGTAGATGG  TCTCTATTAT  GTATACTACG  CTGTGTCGAC  CTTTGGATCC   1560

CAAGATTCCG  CCATCGGACT  TGCAACGTCC  GAGACGATGG  AATATGGCTC  TTGGACGGAT   1620

CATGGCTCCA  CTGGCATTGC  GTCTTCCTCA  GCCAAGATTT  ATAATGCGAT  CGACCCCAAC   1680

CTGATCTACG  CCGATGGCAC  CTACTACATC  AACTTTGGGT  CGTTCTGGGA  TGACATTTAC   1740

CAAGTCCCGA  TGAAGTCGAC  CCCAACGGCA  GCTGCCTCTT  CCTCCTACAA  TCTTGCGTAT   1800

GACCCGTCGG  GTACCCATGC  GGAGGAGGGT  TCCTATATGT  TTCAGTACGG  TGACTACTAC   1860

TACCTCTTTT  ACTCGGCAGG  TATCTGCTGT  GGATACGATA  CATCCATGCC  CGCTTCCGGA   1920

GAGGAGTATC  ATATCAAGGT  CTGCCGTTCG  ACTTCGCCCA  CGGGTGATTT  CGTAAGTATA   1980

TCCGACATTT  AGAGAAAATA  CTAAGTAGGG  AAAGCTAACC  TGGTGCTAAG  GTTGACTCCG   2040

ACGGTACGGC  GTGCACGGAT  GGCGGGGGCA  CGATGGTGCT  CGAAAGCCAT  GGAGAAGTCT   2100

ATGGCCCTGG  CGGACAGTAA  GTGATTCTGC  AGCTGCCCCA  CCGATATTTA  TGCTTATCAT   2160

GTTTTAGGGG  TGTGTATGAC  GATCCCAACC  TTGGTCCGGT  TCTTTACTAC  CACTACATGA   2220

ACACCACGAT  TGGATACGCG  GATTCTGACG  CGCAGTTTGG  GTGGAACACG  ATCGACTTCT   2280

CTGACGGATG  GACCGGTTGT  ATAAGCATCT  TGGTTGGCGA  TGGAAATGGT  GCTGCCTACG   2340

AGAGGGTCTA  CAAGTTGTAT  ATAGGATTGC  GGCTATGAAC  TCGGCCGAGA  TATAGTTAGT   2400

TAGTAACTAC  ATAGTGGAAT  CGTTAGTCAC  TAATGCAGCC  CGCATGAGTG  CTCTGCCTGA   2460

GGCTTCAGTA  CTGTCCCTCA  ATTTCTGTTT  CTGTTTTTAG  TTTAAGCTCT  GCAGCTGCTC   2520

CCCACCCATT  CATCCACTCA  TTTGGTGAAG  ACATTCATTC  TTCCCTTCAA  CCACTCTATT   2580

AGAGCATTTC  CATCTTCTCA  CACTGATCAT  CGTAATGCAG  ATTCAAGATC  AGTTTGGATT   2640

GAGATCCCTA  CTGCATGCAC  TGTGTGCGTG  ACAGAAGCTG  GAACTGGTAC  TCGCTCGATC   2700

CGTGCAGCGC  GAGTCAGTCA  CATCCGCCCT  GCGCTTCAGA  CTAGCCTGCC  AATAGTGACT   2760

ATCACAAGGG  CCGTACTAAG  ATCGAATAAC  AGCTTTCCTA  ACAACATCGC  GTTAACGTGT   2820
```

```
TACTTTCCTC  CAGCTTACAT  TTTGCTATTG  AAGCCATATA  CGATCCCTTC  GATGCGCTCG    2880

GTTTAACTTC  TGCCACGATC  ACCCGTTCAT  CGAAGATTCT  GGGAGTCTGT  CGGTCTTCAT    2940

GCCAGCAAAG  ATCGACTCAA  ATACACACAG  TCAGCAACAT  CTGTTGCTTG  TTACGGATGG    3000

TGCCTATTAT  AATGCATGAA  TAGGGGACCA  AGCAATTCTC  CGCTGTCGGC  GATGTTGAAT    3060

TAAGGAGGGA  TAATATTTGA  TCGAATGACA  AAGGGAAGAA  TTGTGCGACA  CGAGGGAACC    3120

TTATACTTGT  CTACGGCCTA  GCAGCAA                                           3147
```

(2) INFORMATION FOR SEQ ID NO:24:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24: FORMULA 23:

```
Met  Tyr  Gln  Leu  Leu  Ser  Val  Ala  Ser  Val  Pro  Leu  Leu  Ala  Ser  Leu
-19            -15                 -10                           -5

Val  His  Gly  Tyr  Ala  Asp  Pro  Gly  Ala  Cys  Ser  Gly  Val  Cys  Thr  Thr
           -1   +1                  5                      10

His  Asp  Pro  Gly  Leu  Ile  Arg  Arg  Glu  Ser  Asp  Gly  Thr  Tyr  Phe  Leu
     15                  20                           25

Phe  Ser  Thr  Gly  Asn  Lys  Ile  Ser  Tyr  Val  Ser  Ala  Ser  Ser  Ile  Glu
30                       35                      40                           45

Gly  Pro  Trp  Thr  Ser  Val  Gly  Ser  Met  Leu  Pro  Asp  Gly  Ser  Ser  Ile
               50                      55                           60

Asp  Leu  Asp  Gly  Asn  Asp  Asp  Leu  Trp  Ala  Pro  Asp  Val  Ser  Tyr  Val
               65                      70                      75

Asp  Gly  Leu  Tyr  Tyr  Val  Tyr  Tyr  Ala  Val  Ser  Thr  Phe  Gly  Ser  Gln
          80                      85                      90

Asp  Ser  Ala  Ile  Gly  Leu  Ala  Thr  Ser  Glu  Thr  Met  Glu  Tyr  Gly  Ser
     95                 100                      105

Trp  Thr  Asp  His  Gly  Ser  Thr  Gly  Ile  Ala  Ser  Ser  Ser  Ala  Lys  Ile
110                      115                      120                         125

Tyr  Asn  Ala  Ile  Asp  Pro  Asn  Leu  Ile  Tyr  Ala  Asp  Gly  Thr  Tyr  Tyr
               130                      135                          140

Ile  Asn  Phe  Gly  Ser  Phe  Trp  Asp  Asp  Ile  Tyr  Gln  Val  Pro  Met  Lys
               145                      150                     155

Ser  Thr  Pro  Thr  Ala  Ala  Ala  Ser  Ser  Ser  Tyr  Asn  Leu  Ala  Tyr  Asp
          160                      165                     170

Pro  Ser  Gly  Thr  His  Ala  Glu  Glu  Gly  Ser  Tyr  Met  Phe  Gln  Tyr  Gly
     175                      180                     185

Asp  Tyr  Tyr  Tyr  Leu  Phe  Tyr  Ser  Ala  Gly  Ile  Cys  Cys  Gly  Tyr  Asp
190                      195                      200                         205

Thr  Ser  Met  Pro  Ala  Ser  Gly  Glu  Glu  Tyr  His  Ile  Lys  Val  Cys  Arg
               210                      215                          220

Ser  Thr  Ser  Pro  Thr  Gly  Asp  Phe  Val  Asp  Ser  Asp  Gly  Thr  Ala  Cys
               225                      230                     235

Thr  Asp  Gly  Gly  Gly  Thr  Met  Val  Leu  Glu  Ser  His  Gly  Glu  Val  Tyr
          240                      245                     250

Gly  Pro  Gly  Gly  Gln  Gly  Val  Tyr  Asp  Asp  Pro  Asn  Leu  Gly  Pro  Val
     255                      260                     265

Leu  Tyr  Tyr  His  Tyr  Met  Asn  Thr  Thr  Ile  Gly  Tyr  Ala  Asp  Ser  Asp
```

|  | 270 | | | 275 | | | | 280 | | | | | 285 | |
|---|---|---|---|---|---|---|---|---|---|---|---|---|---|---|
| Ala | Gln | Phe | Gly | Trp | Asn | Thr | Ile | Asp | Phe | Ser | Asp | Gly | Trp | Thr | Gly |
| | | | | 290 | | | | | 295 | | | | | 300 | |
| Cys | Ile | Ser | Ile | Leu | Val | Gly | Asp | Gly | Asn | Gly | Ala | Ala | Tyr | Glu | Arg |
| | | | 305 | | | | | 310 | | | | | 315 | | |
| Val | Tyr | Lys | Leu | Tyr | Ile | Gly | Leu | Arg | Leu | | | | | | |
| | | 320 | | | | | 325 | | | | | | | | |